(12) United States Patent
Bres et al.

(10) Patent No.: US 12,404,559 B2
(45) Date of Patent: Sep. 2, 2025

(54) **DETECTING *BABESIA* SPECIES NUCLEIC ACID IN A SAMPLE**

(71) Applicant: Gen-Probe Incorporated, San Diego, CA (US)

(72) Inventors: Vanessa Bres, San Diego, CA (US); Deanna Self, Escondido, CA (US); Jeffrey M. Linnen, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 27 days.

(21) Appl. No.: 18/159,218

(22) Filed: Jan. 25, 2023

(65) Prior Publication Data

US 2023/0227922 A1    Jul. 20, 2023

Related U.S. Application Data

(62) Division of application No. 16/611,806, filed as application No. PCT/US2018/036214 on Jun. 6, 2018, now Pat. No. 11,667,978.

(60) Provisional application No. 62/516,530, filed on Jun. 7, 2017, provisional application No. 62/520,793, filed on Jun. 16, 2017.

(51) Int. Cl.
  *C12Q 1/68*      (2018.01)
  *C07H 21/04*     (2006.01)
  *C12Q 1/6806*    (2018.01)
  *C12Q 1/6893*    (2018.01)

(52) U.S. Cl.
  CPC ......... *C12Q 1/6893* (2013.01); *C12Q 1/6806* (2013.01); *C12Q 2600/16* (2013.01); *C12Q 2600/166* (2013.01)

(58) Field of Classification Search
  None
  See application file for complete search history.

(56) References Cited

U.S. PATENT DOCUMENTS

| | | | |
|---|---|---|---|
| 4,581,333 A | 4/1986 | Kourilsky et al. | |
| 4,683,195 A | 7/1987 | Mullis et al. | |
| 4,683,202 A | 7/1987 | Mullis et al. | |
| 4,786,600 A | 11/1988 | Kramer et al. | |
| 4,800,159 A | 1/1989 | Mullis et al. | |
| 4,868,105 A | 9/1989 | Urdea et al. | |
| 5,118,801 A | 6/1992 | Lizardi et al. | |
| 5,124,246 A | 6/1992 | Urdea et al. | |
| 5,130,238 A | 7/1992 | Malek et al. | |
| 5,283,174 A | 2/1994 | Arnold, Jr. et al. | |
| 5,312,728 A | 5/1994 | Lizardi et al. | |
| 5,378,825 A | 1/1995 | Cook et al. | |
| 5,422,252 A | 6/1995 | Walker et al. | |
| 5,424,413 A | 6/1995 | Hogan et al. | |
| 5,427,930 A | 6/1995 | Birkenmeyer et al. | |
| 5,437,990 A | 8/1995 | Burg et al. | |
| 5,451,506 A | 9/1995 | Shoyab et al. | |
| 5,516,663 A | 5/1996 | Backman et al. | |

(Continued)

FOREIGN PATENT DOCUMENTS

| | | |
|---|---|---|
| CA | 2922689 A1 | 5/2015 |
| CN | 102181556 | 9/2011 |

(Continued)

OTHER PUBLICATIONS

Allawi, et al., Invader Plus Method Detects Herpes Simplex Virus in Cerebrospinal Fluid and Simultaneously Differentiates Types 1 and 2. J. Clin. Microbiol. 44:3443-3447, 2006.

(Continued)

*Primary Examiner* — Jeanine A Goldberg
(74) *Attorney, Agent, or Firm* — Knobbe, Martens, Olson & Bear LLP

(57) ABSTRACT

There is described herein a method for specifically detecting *Babesia* species nucleic acid in a sample, which in one aspect comprises: (1) contacting a sample, said sample suspected of containing *Babesia* species nucleic acid, with at least two oligomers for amplifying a target region of a *Babesia* species target nucleic acid, wherein the at least two amplification oligomers comprise: (a) a first amplification oligomer comprising a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) a second amplification oligomer comprising a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; or (iii) is contained in SEQ ID NO:70 and comprises SEQ ID NO:46, SEQ ID NO:47, SEQ ID NO:48, SEQ ID NO:49, SEQ ID NO:50, or SEQ ID NO:51; (2) performing an in vitro nucleic acid amplification reaction, wherein any *Babesia* target nucleic acid present in said sample is used as a template for generating an amplification product; and (3) detecting the presence or absence of the amplification product, thereby indicating the presence or absence of *Babesia* species target nucleic acid in said sample.

13 Claims, No Drawings
Specification includes a Sequence Listing.

(56) References Cited

U.S. PATENT DOCUMENTS

| | | | |
|---|---|---|---|
| 5,547,842 | A | 8/1996 | Hogan et al. |
| 5,547,861 | A | 8/1996 | Nadeau et al. |
| 5,554,516 | A | 9/1996 | Kacian et al. |
| 5,585,481 | A | 12/1996 | Arnold, Jr. et al. |
| 5,614,402 | A | 3/1997 | Dahlberg et al. |
| 5,648,211 | A | 7/1997 | Fraiser et al. |
| 5,658,737 | A | 8/1997 | Nelson et al. |
| 5,823,174 | A | 10/1998 | Andress |
| 5,846,717 | A | 12/1998 | Brow et al. |
| 5,849,481 | A | 12/1998 | Urdea et al. |
| 5,925,517 | A | 7/1999 | Tyagi et al. |
| 6,150,097 | A | 11/2000 | Tyagi et al. |
| 6,180,340 | B1 | 1/2001 | Nelson |
| 6,350,579 | B1 | 2/2002 | Nelson |
| 6,361,945 | B1 | 3/2002 | Becker et al. |
| 6,534,274 | B2 | 3/2003 | Becker et al. |
| 6,706,471 | B1 | 3/2004 | Brow et al. |
| 6,835,542 | B2 | 12/2004 | Becker et al. |
| 6,849,412 | B2 | 2/2005 | Becker et al. |
| 6,949,367 | B1 | 9/2005 | Dempey et al. |
| 7,374,885 | B2 | 5/2008 | Becker et al. |
| 11,667,978 | B2* | 6/2023 | Bres ............... C12Q 1/6806 435/6.11 |
| 2006/0068417 | A1 | 3/2006 | Becker et al. |
| 2006/0194240 | A1 | 8/2006 | Arnold et al. |
| 2013/0157874 | A1 | 6/2013 | Dowd |
| 2016/0201144 | A1* | 7/2016 | Chelliserry ........ C12Q 1/6806 435/6.11 |

FOREIGN PATENT DOCUMENTS

| | | |
|---|---|---|
| CN | 102230008 | 11/2011 |
| CN | 103103286 | 10/2014 |
| WO | WO 88/01302 A1 | 2/1988 |
| WO | WO 88/10315 A1 | 12/1988 |
| WO | WO 89/002476 A1 | 3/1989 |
| WO | WO 93/13121 A1 | 7/1993 |
| WO | WO 95/03430 A1 | 2/1995 |
| WO | WO 95/32305 A1 | 11/1995 |
| WO | WO 99/60009 A1 | 11/1999 |
| WO | WO 2014/071946 A1 | 5/2014 |
| WO | WO 2014/197607 A1 | 12/2014 |
| WO | WO 2016/064887 A1 | 4/2016 |
| WO | WO 2016/183282 A1 | 11/2016 |

OTHER PUBLICATIONS

Allawi, et al., Modeling of Flap Endonuclease Interactions with DNA Substrate, J. Mol. Biol. (2003) 328, 537-554. doi:10.1016/S0022-2836(03)00351-6.

Berger, et al., Methods in Enzymology, vol. 152, Guide to Molecular Cloning Techniques; pp. 20-24, 33-48, 94-112, 173-180, 215-219, 248-254, 307-329, 343-349, 432-442, 522-538 and 556-562 (Academic Press, Inc., San Diego, Calif., 1987).

Cagnin, et al., Overview of Electrochemical DNA Biosensors: New Approaches to Detect the Expression of Life, Sensors 2009, 9, 3122-3148; doi:10.3390/s90403122.

Daniels, et al., Label-Free Impedance Biosensors: Opportunities and Challenges, Electroanalysis. May 16, 2007; 19(12): 1239-1257.

Drummond, et al., Electrochemical DNA sensors, Nat. Biotechnol. (2003) 21: 1192.

Eis, et al., An invasive cleavage assay for direct quantitation of specific RNAs, Nature Publishing Group, http://biotech.nature.com (Jul. 2001) vol. 19.

Feng, et al, Roles of divalent metal ions in flap endonuclease-substrate interactions, Nat. Struct. Mol. Biol. 11 :450-456, 2004.

Gooding, J. Justin, Electrochemical DNA Hybridization Biosensors, Electroanalysis 14: 1149, 2002.

Katz, et al., Probing Biomolecular Interactions at Conductive and Semiconductive Surfaces by Impedance Spectroscopy: Routes to Impedimetric Immunosensors, DNA-Sensors, and Enzyme Biosensors, Electroanalysis 2003, 15, No. 11.

Kaiser, et al., A Comparison of Eubacterial and Archaeal Structure-specific 5*- Exonucleases*, The Journal of Biological Chemistry, vol. 274, No. 30, Issue of Jul. 23, pp. 21387-21394, 1999.

Levin, et al., Transfusion-transmitted babesiosis: Is it time to screen the blood supply? Curr Opin Hematol (2016) 23(6):573-580.

Lyamichev, et al., Polymorphism identification and quantitative detection of genomic DNA by invasive cleavage of oligonucleotide probes, Nat. Biotechnol.(1999) 17:292-296.

Lyamichev, et al., Structure-Specific Endonucleolytic Cleavage of Nucleic Acids by Eubacterial DNA Polymerases, Science (May 1993) vol. 20, 7.

Ma, et al., RNA Template-dependent 5* Nuclease Activity of Thermus aquaticus and Thermus thermophilus DNA Polymerases*, The Journal of Biological Chemistry (2000) vol. 275, No. 32, Issue of Aug. 11, pp. 24693-24700.

Moritz, et al., Screening for Babesia microti in the U.S.Blood Supply N Engl J Med . (2016) 8, 375(23):2236-2245.

Ryan, et al., Non-PCR-Dependent Detection of the Factor V Leiden Mutation from Genomic DNA Using a Homogeneous Invader Microtiter Plate Assay, Mol. Diagn. (19999) 4: 135-144.

Sharma, et al., The Exonucleolytic and Endonucleolytic Cleavage Activities of Human Exonuclease 1 Are Stimulated by an Interaction with the Carboxyl-terminal Region of the Werner Syndrome Protein* J. Biol. Chem. (2003) vol. 278, No. 26, Issue of Jun. 27, pp. 23487-23496.

Shen, et al., Flap endonuclease homologs in archaebacteria exist as independent proteins, TIBS 23, May 1998.

Vester, et al., LNA (Locked Nucleic Acid): High-Affinity Targeting of Complementary RNA and DNA†, Biochemistry (2004) 43: 13233-41.

Wang, Joseph, Electrochemical nucleic acid biosensors, Anal. Chim. Acta (2002) 469:63.

Examination Report dated Oct. 3, 2024, in corresponding Canadian Application No. 3,054,603.

Blaschitz, et al., Babesia Species Occurring in Austrian Ixodes Ricinus Ticks, Applied and environmental microbiology; 2008: pp. 4841-4846. doi:10.1128/AEM.00035-08.

Bloch, et al. Development of real-time polymerase chain reaction assay for detection and quantitation of Babesia microti infection. Transfusion, 2013, vol. 53, Issue 10.

Cornillot, et al. Sequencing of the smallest *Apicomplexan* genome from the human pathogen Babesia microli, Nucleic Acids Research, 2012, vol. 40, No. 18.

Criado-Fornelio, A., "A review of nucleic-acid-based diagnostic tests for Babesia and Theileria, with emphasis on bovine piroplasms", Italy May 1, 2007 (May 1, 2007), p. 39.

Eshoo, et al., Broad-Range Survey of Tick-Borne Pathogens in Southern Germany Reveals a High Prevalence of Babesia microti and a Diversity of Other Tick-Borne Pathogens Vector-Borne and zoonotic diseases, Vector-Borne and Zoonotic Diseases (2014) vol. 14; No. 8, pp. 584-591.

Teal, et al., A new real-time PCR assay for improved detection of the parasite *Babesia microli*, Journal of Clinical Microbiology (2012) vol. 50, No. 3, pp. 903-908.

Tonnetti, et al., Transfusion-transmitted Babesia microti identified through hemovigilance, Transfusion (2009) vol. 49, pp. 2557-2563.

International Search Report and Written Opinion mailed Aug. 9, 218, in corresponding application No. PCT/US2018/036214.

Examination Report dated Dec. 21, 2020, in corresponding European Application No. 18734394.2.

Examination Report dated Apr. 20, 2021, in corresponding Australian Application No. 2018281196.

* cited by examiner

DETECTING *BABESIA* SPECIES NUCLEIC ACID IN A SAMPLE

CROSS-REFERENCE TO RELATED APPLICATIONS

This application is a divisional of U.S. application Ser. No. 16/611,806, filed Nov. 7, 2019, which is a national stage entry of International Application No. PCT/US2018/036214, filed Jun. 6, 2018, which claims the benefit under 35 U.S.C. § 119(e) of U.S. Provisional Application Nos. 62/516,530, filed Jun. 7, 2017, and 62/520,793, filed Jun. 16, 2017. The entire contents of each of the foregoing applications are incorporated herein by reference in their entirety.

REFERENCE TO SEQUENCE LISTING

The instant application contains a Sequence Listing which has been submitted electronically in XML format and is hereby incorporated by reference in its entirety. Said XML Copy, created on Mar. 30, 2023, is named "GPR_7520 US_Seq_Listing" and is 158,798 bytes in size.

BACKGROUND

Babesiosis is caused by infection of red blood cells by species of protozoan parasites of the genus *Babesia*. The species *Babesia microti* is responsible for most human babesiosis infections reported in the United States. Infections are typically asymptomatic in human individuals but can lead to severe illness or death, especially in elderly or immunosuppressed individuals. The parasite is transmitted to humans by exposure to deer ticks in endemic areas or by blood transfusion (transfusion-transmitted babesiosis (TTB)). Over 100 cases of transfusion-transmitted babesiosis have been reported to the FDA since 1979. Despite being reported as the most unaddressed infectious risk to the United States blood supply, there is still no licensed test for screening for *B. microti* in donated blood (*N Engl J Med.* (2016) 8, 375(23):2236-2245). The threat of TTB has led to a consensus by the Food and Drug Administration (FDA) and the American Association of Blood Banks (AABB) that screening of blood donations for *Babesia* is urgently required for blood safety. Initiation of blood donor screening to prevent TTB should be given high priority (*Curr Opin Hematol.* (2016) 23(6):573-580).

Therefore a specific and sensitive assay for detecting *Babesia* species in a sample is needed.

SUMMARY

In one aspect, there is provided a method for specifically detecting *Babesia* species nucleic acid in a sample, said method comprising: (1) contacting a sample, said sample suspected of containing *Babesia* species nucleic acid, with at least two oligomers for amplifying a target region of a *Babesia* species target nucleic acid, wherein the at least two amplification oligomers comprise: (a) a first amplification oligomer comprising a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) a second amplification oligomer comprising a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; (iii) is contained in SEQ ID NO:70 and comprises SEQ ID NO:46, SEQ ID NO:47, SEQ ID NO:48, SEQ ID NO:49, SEQ ID NO:50, or SEQ ID NO:51, or (iv) comprises or consists of SEQ ID NO:84; (2) performing an in vitro nucleic acid amplification reaction, wherein any *Babesia* target nucleic acid present in said sample is used as a template for generating an amplification product; and (3) detecting the presence or absence of the amplification product, thereby indicating the presence or absence of *Babesia* species target nucleic acid in said sample.

Suitably, the first target-hybridizing sequence comprises or consists of a sequence selected from the group consisting of: SEQ ID NOs:2, and 4 and 6 and 8, suitably, wherein the first target-hybridizing sequence comprises or consists of a sequence selected from the group consisting of: SEQ ID NOs:2, and 4 and 8.

Suitably, the second amplification oligomer comprises or consists of the sequence selected from the group consisting of: SEQ ID NOs:13, 16, 17, 18, 19, 20, 21, 27, 28, 29, 31, 32, 33, 34, 35, 36, 84 and 86.

Suitably, the second amplification oligomer sequence comprises or consists of SEQ ID NO:21 or SEQ ID NO:27 or SEQ ID NO:34 or SEQ ID NO:84 or SEQ ID NO:86.

Suitably, the first amplification oligomer is a promoter primer or promoter provider further comprising a promoter sequence located 5' to the first target-hybridizing sequence. Suitably, the promoter sequence is a T7 promoter sequence. Suitably, the T7 promoter sequence comprises or consists of SEQ ID NO:58.

Suitably, the first amplification oligomer comprises or consists of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the first and second target-hybridizing sequences respectively comprise or consist of the nucleotide sequences of: (a) SEQ ID NO:SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (f) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (l) SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:35; (t) SEQ ID NO:83 and SEQ ID NO:36; (u) SEQ ID NO:83 and SEQ ID NO:84; (v) SEQ ID NO:83 and SEQ ID NO:86.

Suitably, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g)

SEQ ID NO:83 and SEQ ID NO:34; (h) SEQ ID NO:83 and SEQ ID NO:84; (i) SEQ ID NO:83 and SEQ ID NO:86.

Suitably, the method further comprises purifying the target nucleic acid from other components in the sample before step (1).

Suitably, the purifying step comprises contacting the sample with at least one capture probe oligomer comprising a target-hybridizing sequence covalently attached to a sequence or moiety that binds to an immobilized probe, wherein said target-hybridizing sequence (i) is from about 15 to 21 contiguous nucleotides contained in the sequence of SEQ ID NO:78; or (ii) is from about 21 to 30 contiguous nucleotides comprising the sequence of SEQ ID NO:78; or (iii) is the sequence is SEQ ID NO:44. Suitably, the capture probe oligomer sequence comprises or consists of SEQ ID NO:43.

Suitably, the detecting step (3) comprises contacting said in vitro nucleic acid amplification reaction with a detection probe oligomer configured to specifically hybridize to the amplification product under conditions whereby the presence or absence of the amplification product is determined, thereby indicating the presence or absence of *Babesia* species in said sample.

Suitably, the detection probe oligomer comprises a target-hybridizing sequence that is from about 14 to about 40 nucleotides in length and is configured to specifically hybridize to a target sequence comprising or consisting of SEQ ID NO:59, the RNA equivalent of SEQ ID NO:59, the complement of SEQ ID NO:59, the RNA equivalent of the complement of SEQ ID NO:59, or SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence is contained in the sequence of SEQ ID NO:65 and includes at least the sequence of SEQ ID NO:37 or SEQ ID NO:42.

Suitably, the detection probe target-hybridizing sequence is contained in the sequence of SEQ ID NO:41 and includes at least the sequence of SEQ ID NO:38 or SEQ ID NO:39.

Suitably, the detection probe consists of the sequence selected from the group consisting of: SEQ ID NO:37, 38, 39, 41, 42, 91, 92, 94, or 99.

Suitably, the detection probe comprises or consists of a nucleotide sequence selected from the group consisting of SEQ ID NOs:37, 38, 39, 40, 41, 42, 59, 60, 91, 92, 93, 94, 98 and 99.

Suitably, the detection probe oligomer further comprises a 2' methoxy modification on at least one nucleotide residue member of the nucleotide sequence.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (l) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; (u) SEQ ID NO:8 and SEQ ID NO:36 and SEQ ID NO:37 or SEQ ID NO:42; (v) SEQ ID NO:8, and SEQ ID NO:34, 84, or 86, and SEQ ID NO:91, 92, or 93; (v) SEQ ID NO:8, and SEQ ID NO:34, 84, or 86, and SEQ ID NO:37, 38, 39, 40, 41, 42, 59, 60, 91, 92, 93, 94, 98 or 99; or (x) SEQ ID NO:83, and SEQ ID NO:34, 84, or, 86, and SEQ ID NO:91, 92, or 93.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:27 and SEQ ID NO:38; (b) SEQ ID NO:4 and SEQ ID NO:21 and SEQ ID NO:39; (c) SEQ ID NO:8 and SEQ ID NO:21 and SEQ ID NO:37 or SEQ ID NO:39; (d) SEQ ID NO:8 and SEQ ID NO:34 and SEQ ID NO:37, 42, 91, 92 or 93; (e) SEQ ID NO:8 and SEQ ID NO:34, or 84 or 86 and SEQ ID NO:37, 42, 91, 92 or 93; (f) SEQ ID NO:83 and SEQ ID NO:34, 84 or 86 and SEQ ID NO:37, 42, 91, 92 or 93; (g) SEQ ID NO:8 and SEQ ID NO:34, 84 or 86 and SEQ ID NO:37, 42, 91, 92 or 93; (h) SEQ ID NO:83 and SEQ ID NO:34, 84 or 86 and SEQ ID NO:37, 38, 39, 40, 41, 42, 59, 60, 91, 92, 93, 94, 98 or 99; or (i) SEQ ID NO:83 and SEQ ID NO:34, 84 or 86 and SEQ ID NO:37, 42, 91, 92 or 93.

Suitably, the detection probe comprises a label. Suitably, the label is a chemiluminescent label or a fluorescent label. Suitably, the detecting step (3) occurs during the amplifying step (2). Suitably, the detection probe comprises a fluorescent label and a quencher. Suitably, the detection probe is selected from the group consisting of a molecular torch, a molecular beacon, and a TaqMan detection probe. Suitably, the detection probe further comprises a non-target-hybridizing sequence. Suitably, the detection probe is a molecular torch or a molecular beacon.

Suitably, the amplification reaction at step (2) is an isothermal amplification reaction. Suitably, the amplification reaction is a transcription-mediated amplification (TMA) reaction. Suitably, the amplification reaction is a real-time amplification reaction.

Suitably, the sample is a clinical sample. Suitably, the sample is a blood sample. Suitably, the sample is a lysed blood cell sample. Suitably, the lysed blood cell sample is a lysed red blood cell sample.

Suitably, the amplification product has a length of from 180 to 220 contiguous nucleotides and contains SEQ ID NO:65 or the complement thereof.

In a further aspect, there is described a method for specifically detecting *Babesia* species nucleic acid in a sample, said method comprising: (1) contacting a sample, said sample suspected of containing *Babesia* species nucleic acid, with at least two oligomers for amplifying a target region of a *Babesia* species target nucleic acid, wherein two of said at least two amplification oligomers are selected from the group consisting of: (a) a first amplification oligomer and a second amplification oligomer, wherein the first amplification oligomer comprises a first target-hybridizing sequence (i) that is from 15 to 33 contiguous nucleobases in length, is contained in SEQ ID NO:66 and contains SEQ ID NO:56 or SEQ ID NO:57, or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises/consists of SEQ ID NO:8; (v) comprises or consists of SEQ ID NO:83; or (b) a first amplification oligomer and a second amplification oligomer, wherein the second amplification oligomer comprises a second target-hybridizing sequence that is from about 15 to about 33 contiguous nucleotides in length, and (i) is contained in SEQ ID NO:68 and contains SEQ ID NO:52, SEQ ID NO:53 SEQ ID NO:54, SEQ ID NO:55, or SEQ ID NO:85, or (ii) is contained in SEQ ID NO:67 and contains SEQ ID NO:45 or SEQ ID NO:69, or (iii) is contained in SEQ ID NO:70 and contains SEQ ID NO:46, SEQ ID NO:47, SEQ ID NO:48, SEQ ID NO:49, SEQ ID NO:50, or SEQ ID NO:51, or (iv) comprises or consists of SEQ ID NO:84; (2) performing an in vitro nucleic acid amplification reaction, wherein any Babesia target nucleic acid present in said sample is used as a template for generating an amplification product, wherein said amplification product has a length of from 180 to 220 contiguous nucleotides and contains SEQ ID NO:65 or the complement thereof; and (3) detecting the presence or absence of the amplification product, thereby indicating the presence or absence of Babesia species target nucleic acid in said sample.

Suitably, the first target-hybridizing sequence comprises or consists of a sequence selected from the group consisting of: SEQ ID NOs:2, and 4 and 6 and 8, suitably, wherein the first target-hybridizing sequence comprises or consists of a sequence selected from the group consisting of: SEQ ID NOs:2, and 4 and 8.

Suitably, the second amplification oligomer comprises or consists of the sequence selected from the group consisting of: SEQ ID NOs:13, 16, 17, 18, 19, 20, 21, 27, 28, 29, 31, 32, 33, 34, 35, 36, 84, and 86.

Suitably, the second amplification oligomer sequence comprises or consists of SEQ ID NO:21 or SEQ ID NO:27 or SEQ ID NO:34 or SEQ ID NO:84 or SEQ ID NO:86.

Suitably, the first amplification oligomer is a promoter primer or promoter provider further comprising a promoter sequence located 5' to the first target-hybridizing sequence. Suitably, the promoter sequence is a T7 promoter sequence. Suitably, the T7 promoter sequence comprises or consists of SEQ ID NO:58. Suitably, the first amplification oligomer comprises or consists of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the first and second target-hybridizing sequences respectively comprise or consist of the nucleotide sequences of: (a) SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (f) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (l) SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:84; (t) SEQ ID NOs:83 and SEQ ID NO:86.

Suitably, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g) SEQ ID NO:83 and SEQ ID NO:34; (h) SEQ ID NO:83 and SEQ ID NO:84; (i) SEQ ID NO:83 and SEQ ID NO:86.

Suitably, the method further comprises purifying the target nucleic acid from other components in the sample before step (1).

Suitably, the purifying step comprises contacting the sample with at least one capture probe oligomer comprising a target-hybridizing sequence covalently attached to a sequence or moiety that binds to an immobilized probe, wherein said target-hybridizing sequence (i) is from about 15 to 21 contiguous nucleotides contained in the sequence of SEQ ID NO:78; or (ii) is from about 21 to about 30 contiguous nucleotides comprising the sequence of SEQ ID NO:78; or (iii) the sequence consists of SEQ ID NO:44.

Suitably, the capture probe oligomer sequence comprises or consists of SEQ ID NO:43.

Suitably, the detecting step (3) comprises contacting said in vitro nucleic acid amplification reaction with a detection probe oligomer configured to specifically hybridize to the amplification product under conditions whereby the presence or absence of the amplification product is determined, thereby indicating the presence or absence of Babesia species in said sample.

Suitably, the detection probe oligomer comprises a target-hybridizing sequence that is from about 14 to about 40 nucleotides in length and is configured to specifically hybridize to a target sequence comprising or consisting of SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence is contained in the sequence of SEQ ID NO:59 and includes at least the sequence of SEQ ID NO:42, 92, 94, or 99.

Suitably, the detection probe target-hybridizing sequence is contained in the sequence of SEQ ID NO:41 and includes at least the sequence of SEQ ID NO:38 or SEQ ID NO:60.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence containing SEQ ID NO:59 or SEQ ID NO:60.

Suitably, the detection probe oligomer further comprises a nucleotide sequence consisting of SEQ ID NO:37, 38, 39, 42, or 99.

Suitably, the detection probe target-hybridizing sequence consists of the sequence selected from the group consisting of: SEQ ID NOs:37, 38, 39, 40, 41, 42, 59, 60, 91, 92, 93, 94, 98 and 99.

Suitably, the detection probe oligomer further comprises a 2' methoxy modification on at least one nucleotide residue member of the nucleotide sequence.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (l) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; or (u) SEQ ID NO:8 and SEQ ID NO:36 and SEQ ID NO:37 or SEQ ID NO:42; (v) SEQ ID NO:8, and SEQ ID NO:84, and SEQ ID NOs:91, 92 and/or 93; (w) SEQ ID NO:8, and SEQ ID NO:86, and SEQ ID NOs:91, 92 and/or 93; (x) SEQ ID NO:83, and SEQ ID NO:34, and SEQ ID NOs:91, 92 and/or 93; (y) SEQ ID NOs:83, and SEQ ID NO:84, and SEQ ID NOs:91, 92 and/or 93; (z) SEQ ID NOs:83, and SEQ ID NO:86, and SEQ ID NOs:91, 92 and/or 93; or (aa) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:27 and SEQ ID NO:38; (b) SEQ ID NO:4 and SEQ ID NO:21 and SEQ ID NO:39; (c) SEQ ID NO:8 and SEQ ID NO:21 and SEQ ID NO:37 or SEQ ID NO:39; or (d) SEQ ID NO:8 and SEQ ID NO:34 and SEQ ID NO:37 or SEQ ID NO:42; (e) SEQ ID NO:8, and SEQ ID NO:84, and SEQ ID NOs:91, 92 and/or 93; (f) SEQ ID NO:8, and SEQ ID NO:86, and SEQ ID NOs:91, 92 and/or 93; (g) SEQ ID NO:83, and SEQ ID NO:34, and SEQ ID NOs:91, 92 and/or 93; (h) SEQ ID NOs:83, and SEQ ID NO:84, and SEQ ID NOs:91, 92 and/or 93; (i) SEQ ID NOs:83, and SEQ ID NO:86, and SEQ ID NOs:91, 92 and/or 93; or (j) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the detection probe comprises a label. Suitably, the label is a chemiluminescent label or a fluorescent label. Suitably, the detecting step (3) occurs during the amplifying step (2). Suitably, the detection probe comprises a fluorescent label and a quencher. Suitably, the detection probe is selected from the group consisting of a molecular torch, a molecular beacon, and a TaqMan detection probe. Suitably, the detection probe further comprises a non-target-hybridizing sequence. Suitably, the detection probe is a molecular torch or a molecular beacon.

Suitably, the amplification reaction at step (2) is an isothermal amplification reaction. Suitably, the amplification reaction is a transcription-mediated amplification (TMA) reaction. Suitably, the amplification reaction is a real-time amplification reaction.

Suitably, the sample is a clinical sample. Suitably, the sample is a blood sample. Suitably, the sample is a lysed blood cell sample.

Suitably, the lysed blood cell sample is a lysed red blood cell sample.

In a further aspect, there is described a combination of at least two oligomers for determining the presence or absence of *Babesia* in a sample, said oligomer combination comprising first and second amplification oligomers for amplifying a target region of *Babesia* target nucleic acid, wherein (a) the first amplification oligomer comprises a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) the second amplification oligomer comprises a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; or (iii) is contained in SEQ ID NO:70 and comprises SEQ ID NO:46, SEQ ID NO:47, SEQ ID NO:48, SEQ ID NO:49, SEQ ID NO:50, or SEQ ID NO:51; or (iv) comprises or consists of SEQ ID NO:84.

Suitably, the first amplification comprises or consists of the sequence selected from the group consisting of: SEQ ID NOs:2 and 4 and 6 and 8 and 83, suitably, wherein the first amplification comprises or consists of the sequence selected from the group consisting of: SEQ ID NOs:2 and 4 and 8 and 83.

Suitably, the second amplification oligomer comprises or consists of the sequence selected from the group consisting of: SEQ ID NOs:13, 16, 17, 18, 19, 20, 21, 27, 28, 29, 31, 32, 33, 34, 35, 36, 84, and 86.

Suitably, the second amplification oligomer sequence comprises or consists of SEQ ID NO:21 or SEQ ID NO:27 or SEQ ID NO:34 or SEQ ID NO:84 or SEQ ID NO:86.

Suitably, the first amplification oligomer is a promoter primer or promoter provider further comprising a promoter sequence located 5' to the first target-hybridizing sequence. Suitably, the promoter sequence is a T7 promoter sequence. Suitably, the T7 promoter sequence comprises or consists of SEQ ID NO:58.

Suitably, the first amplification oligomer comprises or consists of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the first and second target-hybridizing sequences respectively comprise or consist of the nucleotide sequences of: (a) SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (f) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (l) SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:84; or (t) SEQ ID NO:83 and SEQ ID NO:86.

Suitably, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g) SEQ ID NO:83 and SEQ ID NO:34; (h) SEQ ID NO:83 and SEQ ID NO:84; or (i) SEQ ID NO:83 and SEQ ID NO:86.

Suitably, the combination further comprises at least one capture probe oligomer.

Suitably, the at least one capture probe oligomer comprises a target-hybridizing sequence covalently attached to a sequence or moiety that binds to an immobilized probe, wherein said target-hybridizing sequence (i) is from about 15 to about 21 contiguous nucleotides contained in the sequence of SEQ ID NO:78, or (ii) is about 21 to 30 contiguous nucleotides comprising the sequence of SEQ ID NO:78; or (iii) the sequence consists of SEQ ID NO:44.

Suitably, the capture probe oligomer sequence comprises or consists of SEQ ID NO:43.

Suitably, the combination further comprises a detection probe oligomer.

Suitably, the detection probe oligomer comprises a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence contains the sequence of SEQ ID NO:59 and includes at least the sequence of SEQ ID NO:42, 92, 94, or 99.

Suitably, the detection probe target-hybridizing sequence contains the sequence of SEQ ID NO:60 and includes at least the sequence of SEQ ID NO:38 or SEQ ID NO:39.

Suitably, the detection probe target hybridising sequence consists of the sequence selected from the group consisting of: SEQ ID NO:37, 38, 39, 40, 41, 42, 59, 60, 91, 92, 93, 94, 98 or 99.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence containing SEQ ID NO:59 or SEQ ID NO:60.

Suitably, the detection probe oligomer further comprises a nucleotide sequence consisting of SEQ ID NO:37, 38, 39, 40, 41, 42, 59, 60, 91, 92, 93, 94, 98 or 99.

Suitably, the detection probe oligomer further comprises a 2' methoxy modification on at least one nucleotide residue member of the nucleotide sequence.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (l) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; (u) SEQ ID NO:8 and SEQ ID NO:36 and SEQ ID NO:37 or SEQ ID NO:42; (v) SEQ ID NO:8, and SEQ ID NO:84, and SEQ ID NOs:91, 92 and/or 93; (w) SEQ ID NO:8, and SEQ ID NO:86, and SEQ ID NOs:91, 92 and/or 93; (x) SEQ ID NO:83, and SEQ ID NO:34, and SEQ ID NOs:91, 92 and/or 93; (y) SEQ ID NOs:83, and SEQ ID NO:84, and SEQ ID NOs:91, 92 and/or 93; (z) SEQ ID NOs:83, and SEQ ID NO:86, and SEQ ID NOs:91, 92 and/or 93; or (aa) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the first and second amplification oligomer target-hybridizing sequences and the detection probe oligomer target-hybridizing sequences respectively comprise or consist of the nucleotide sequences of: (a) SEQ ID NO:2 and SEQ ID NO:27 and SEQ ID NO:38; (b) SEQ ID NO:4 and SEQ ID NO:21 and SEQ ID NO:39; (c) SEQ ID NO:8 and SEQ ID NO:21 and SEQ ID NO:37 or SEQ ID NO:39; (d) SEQ ID NO:8 and SEQ ID NO:34 and SEQ ID NO:37 or SEQ ID NO:42; (e) SEQ ID NO:8, and SEQ ID NO:84, and SEQ ID NOs:91, 92 and/or 93; (f) SEQ ID NO:8, and SEQ ID NO:86, and SEQ ID NOs:91, 92 and/or 93; (g) SEQ ID NO:83, and SEQ ID NO:34, and SEQ ID NOs:91, 92 and/or 93; (h) SEQ ID NOs:83, and SEQ ID NO:84, and SEQ ID NOs:91, 92 and/or 93; (i) SEQ ID NOs:83, and SEQ ID NO:86, and SEQ ID NOs:91, 92 and/or 93; or (j) SEQ ID NO:8 or 83, SEQ ID NO:34, 84 or 86, and SEQ ID NO:37, 38, 39, 40, 41, 42, 59, 60, 91, 92, 93, 94, 98 or 99.

Suitably, the detection probe comprises a label. Suitably, the label is a chemiluminescent label or a fluorescent label. Suitably, the detection probe comprises a fluorescent label and a quencher. Suitably, the detection probe is selected from the group consisting of a molecular torch, a molecular beacon, and a TaqMan detection probe. Suitably, the detection probe further comprises a non-target-hybridizing sequence. Suitably, the detection probe is a molecular torch or a molecular beacon.

In a further aspect, there is described a detection probe oligomer comprising a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the RNA equivalent of SEQ ID NO:65, the complement of SEQ ID NO:65, or the RNA equivalent of the complement of SEQ ID NO:65.

Suitably, the detection probe target-hybridizing sequence is contained in the sequence of SEQ ID NO:59 and includes at least the sequence of SEQ ID NO:42, 92, 94 or 99.

Suitably, the detection probe target-hybridizing sequence is contained in the sequence of SEQ ID NO:65 and includes at least the sequence of SEQ ID NO:59 or SEQ ID NO:94.

Suitably, the detection probe target hybridising sequence consists of the sequence selected from the group consisting of: SEQ ID NOs:37, 38, 39, 40, 41, 42, 59, 60, 91, 92, 93, 94, 98 and 99.

Suitably, the detection probe oligomer further comprises a 2' methoxy modification on at least one nucleotide residue member of the nucleotide sequence.

Suitably, the detection probe comprises a label. Suitably, the label is a chemiluminescent label or a fluorescent label. Suitably, the detection probe comprises a fluorescent label and a quencher. Suitably, the detection probe is selected from the group consisting of a molecular torch, a molecular beacon, and a TaqMan detection probe.

Suitably, the detection probe further comprises a non-target-hybridizing sequence.

Suitably, the detection probe is a molecular torch or a molecular beacon.

In a further aspect, there is described a capture probe oligomer for specifically isolating *Babesia* species nucleic acid from a sample, said capture probe oligomer comprising a target-hybridizing sequence covalently attached to a sequence or moiety that binds to an immobilized probe, wherein said target-hybridizing sequence is from about 15 to about 30 contiguous nucleotides contained in the sequence of SEQ ID NO:78.

Suitably, the capture probe oligomer sequence comprises or consists of SEQ ID NO:43.

In a further aspect, there is described a kit comprising the combination of at least two oligomers.

In a further aspect, there is described a reaction mixture comprising the combination of at least two oligomers.

In a further aspect, there is described the use of the combination of at least two oligomers for specifically amplifying *Babesia* species nucleic acid in a sample.

In a further aspect, there is described the use of the detection probe oligomer for specifically detecting *Babesia* species nucleic acid in a sample.

In a further aspect, there is described the use of the capture probe oligomer for specifically capturing *Babesia* species nucleic acid from a sample.

Suitably, *Babesia microti* and/or *Babesia divergens* and/or *Babesia duncani* and/or *Babesia venatorum* are detected.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

"Sample" includes any specimen that may contain, or is suspected of containing, *Babesia* nucleic acid or components thereof, such as nucleic acids or fragments of *Babesia* nucleic acids. The sample may be an isolated sample. Samples include "biological samples" which include any tissue or material derived from a living or dead human that may contain the *Babesia* parasite or components thereof (e.g., a target nucleic acid derived therefrom), including, e.g., blood, peripheral blood and red blood cells. The use of other sample types that may contain the *Babesia* parasite or components thereof (e.g., a target nucleic acid derived therefrom)—such as plasma, serum, lymph node, gastrointestinal tissue, faeces, urine, semen or other body fluids or materials—is also contemplated. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see WO95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; The Biochemistry of the Nucleic Acids 5-36, Adams et al, ed., 11th ed., 1992, *BioTechniques* (2007) 43: 617-24), which include derivatives of purine or pyrimidine bases (e.g., N4-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, 06-methylguanine, 4-thio-pyrimidines, 4-amino-pyrimidines, 4-dimethylhydrazine-pyrimidines, and 04-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Biochemistry (2004) 43: 13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

The term "polynucleotide," as used herein, denotes a nucleic acid chain. Throughout this application, nucleic acids are designated by the 5'-terminus to the 3'-terminus. Standard nucleic acids, e.g., DNA and RNA, are typically synthesized "5'-to-3'," i.e., by the addition of nucleotides to the 3'-terminus of a growing nucleic acid.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "nucleic-acid-based detection assay," as used herein, is an assay for the detection of a target sequence within a target nucleic acid and utilizing one more oligonucleotides that specifically hybridize to the target sequence.

In certain embodiments, a nucleic-acid-based detection assay is an "amplification-based assay," i.e., an assay that utilizes one or more steps for amplifying a nucleic acid target sequence. Various amplification methods for use in detection assays are known in the art, several of which are summarized further herein. For the sake of clarity, an amplification-based assay may include one or more steps that do not amplify a target sequence, such as, for example, steps used in non-amplification-based assay methods (e.g., a hybridization assay or a cleavage-based assay).

In other embodiments, a nucleic-acid-based detection assay is a "non-amplification-based assay," i.e., an assay that does not rely on any step for amplifying a nucleic acid target sequence. For the sake of clarity, a nucleic-acid-based detection assay that includes a reaction for extension of a primer in the absence of any corresponding downstream amplification oligomer (e.g., extension of a primer by a reverse transcriptase to generate an RNA:DNA duplex followed by an RNase digestion of the RNA, resulting in a single-stranded cDNA complementary to an RNA target but without generating copies of the cDNA) is understood to be a non-amplification-based assay.

An exemplary non-amplification-based assay is a "cleavage-based assay," which is an assay that relies on the specific cleavage, by a flap endonuclease, of a linear duplex cleavage structure formed by the specific hybridization of overlapping oligonucleotides to a target nucleic acid. In these assays, a probe oligonucleotide containing a non-target-hybridizing flap region is cleaved in an overlap-dependent manner by the flap endonuclease to release a cleavage product that is then detected. The principles of cleavage-based assays are well-known in the art, and exemplary assays are described in, for example, *Nat. Biotechnol.* (1999) 17:292-296, *Mol. Diagn.* (1999) 4: 135-144, *J. Clin. Microbiol.* (2006) 44:3443-3447, and U.S. Pat. Nos. 5,846,717, 6,706,471 and 5,614,402. Cleavage-based assays include, e.g., the commercially available Invader® assays (Hologic, Inc., Madison, WI).

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

By "isolated" it is meant that a sample containing a target nucleic acid is taken from its natural milieu, but the term does not connote any degree of purification.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR, or a non-amplification-based detection assay such as, for example, a cleavage-based assay). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Babesia*. It is understood that other reasons exist for configuring a target-hybridizing sequence to have less than 100% complementarity to a target nucleic acid.

The term "targets a sequence," as used herein in reference to a region of *Babesia* sp. nucleic acid, refers to a process whereby an oligonucleotide hybridizes to the target sequence in a manner that allows for detection as described herein. In one embodiment, the oligonucleotide is complementary with the targeted *Babesia* sp. nucleic acid sequence and contains no mismatches. In another embodiment, the oligonucleotide is complementary but contains 1, 2, 3, 4, or 5 mismatches with the targeted *Babesia* sp. nucleic acid sequence. Preferably, the oligonucleotide that hybridizes to the target nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an oligonucleotide is designed to have a polynucleotide sequence that could target a sequence of the referenced *Babesia* sp. target region. Such an oligonucleotide is not limited to targeting that sequence only, but is rather useful as a composition, in a kit or in a method for targeting a *Babesia* sp. target nucleic acid. The oligonucleotide is designed to function as a component of an assay for detection of *Babesia* sp. from a sample, and therefore is designed to target *Babesia* sp. in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the oligonucleotide target-hybridizing sequence.

The term "fragment," as used herein in reference to a *Babesia* sp. targeted nucleic acid, refers to a piece of contiguous nucleic acid.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. As a non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide can "substantially correspond to" a specified reference nucleic acid sequence, which means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide—such as a first amplification oligomer as described herein—may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800, 159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211). Preferred embodiments use an amplification method suitable for the amplification of RNA target nucleic acids, such as transcription-mediated amplification (TMA) or NASBA, but it will be apparent to persons of ordinary skill in the art that oligomers disclosed herein may be readily used as primers in other amplification methods.

"Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting HSV target sequences as described herein. Variations of transcription-associated amplification are well-known in the art as previously disclosed in detail (e.g., U.S. Pat. Nos. 4,868, 105; 5,124,246; 5,130,238; 5,437,990; 5,554,516; and 7,374,885; and PCT Pub. Nos. WO 88/01302, WO 88/10315, and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

"Probe," "detection probe," "detection oligonucleotide," and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained.

The term "TaqMan® probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

As used herein, a "label" refers to a moiety or compound joined directly or indirectly to a probe that is detected or leads to a detectable signal. Direct labelling can occur through bonds or interactions that link the label to the probe, including covalent bonds or non-covalent interactions, e.g., hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., Molecular Cloning, A Laboratory Manual, 2nd ed. (Cold Spring Harbor Laboratory Press, Cold Spring Harbor, NY, 1989), Chapter 10; U.S. Pat. Nos. 5,658,737, 5,656,207, 5,547,842, 5,283, 174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

"Capture probe," "capture oligonucleotide," "target capture oligonucleotide," and "capture probe oligomer" are used interchangeably herein to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support (see, e.g., WO 2008/016988). The immobilized probe binding region can be a nucleic acid sequence, referred to as a tail. Tails include a substantially homopolymeric tail of about 10 to 40 nucleotides (e.g., Aio to A40), or of about 14 to 33 nt (e.g., T3A14 to T3A30), that bind to a complementary immobilized sequence attached to the support particle or support matrix. Thus, a non-limiting example of preferred nucleic acid tails can in some embodiments include T0-4A1040 sequences. Another example of a capture oligomer comprises two regions, a target hybridizing sequence and a binding pair member that is not a nucleic acid sequence.

As used herein, an "immobilized oligonucleotide," "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size+ 5%), to which an immobilized probe is joined directly (via covalent linkage, chelation, or ionic interaction), or indirectly (via one or more linkers), where the linkage or interaction between the probe and support is stable during hybridization conditions.

DESCRIPTION

The present disclosure is generally directed to methods and compositions for determining the presence or absence of the protozoan parasite *Babesia* sp. in a sample—such as a blood sample. Suitably, the methods and compositions described herein are able to detect the presence of *Babesia microti* and/or *Babesia divergens* and/or *Babesia duncani* and/or *Babesia venatorum*. In some embodiments, the present disclosure provides methods and compositions for diagnosing Babesiosis in a subject. In other, non-mutually exclusive embodiments, the present disclosure provides methods for the detection of *Babesia* sp. in a sample, where the method includes performing amplification-based detection of a target nucleic from *Babesia* sp. The present disclosure further provides compositions (including reaction mixtures) and kits comprising a combination of oligomers for detecting *Babesia* sp.—including *Babesia microti* and/or *Babesia divergens* and/or *Babesia duncani* and/or *Babesia venatorum*—in a sample. The oligomer combination generally includes at least two amplification oligomers for detecting *Babesia* sp.—including *Babesia microti* and/or *Babesia divergens* and/or *Babesia duncani* and/or *Babesia venatorum*—in a sample, and may further include one or more additional oligomers as described herein for performing amplification-based detection of *Babesia* sp.—including *Babesia microti* and/or *Babesia divergens* and/or *Babesia duncani* and/or *Babesia venatorum*—such as, for example, a capture probe and/or a detection probe.

The methods for diagnosing Babesiosis sp. generally include detecting the presence or absence of *Babesia* sp. in a sample from a subject. The sample may be suspected of being infected with or containing *Babesia* sp. The subject may be suspected of being infected with *Babesia* sp. or having Babesiosis. In particular, an assay is performed for the specific detection in the sample of *Babesia* sp. nucleic acid. Based on the results from the detection assay, a status of either positive or negative is assigned for the *Babesia* sp. The presence or absence of Babesiosis in the subject can be determined based on the *Babesia* sp. status.

While *Babesia* sp. nucleic acid may be detected using any suitable method, it is preferred that these protozoan parasites are detected using a nucleic-acid-based detection assay. Nucleic-acid-based detection assays generally utilize oligonucleotides that specifically hybridize to a target nucleic acid of *Babesia* sp. with minimal cross-reactivity to other nucleic acids suspected of being in a sample. Accordingly, oligonucleotides for nucleic-acid-based detection of *Babesia* sp. will have minimal cross-reactivity to other nucleic acids including, for example, *P. falciparum*.

A positive signal from a nucleic-acid-based detection assay in accordance with the present disclosure is indicative of the presence of one or more of *Babesia microti, Babesia divergens, Babesia duncani* and/or *Babesia venatorum* in a sample.

In some embodiments of a method comprising the use of a nucleic-acid-base detection assay—such as an amplification-based assay—is used to detect *Babesia* sp. Such methods generally include amplifying a target sequence within a target nucleic acid utilizing an in vitro nucleic acid amplification reaction and detecting the amplified product by, for example, specifically hybridizing the amplified product with a nucleic acid detection probe that provides a signal to indicate the presence of a target in the sample. The amplification step includes contacting the sample with two or more amplification oligomers specific for a target sequence in a target nucleic acid to produce an amplified product if the target nucleic acid is present in the sample. Amplification synthesizes additional copies of the target sequence or its complement such as, e.g., by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art (see, e.g., discussion of amplification methods in Definitions section, supra) and are readily used in accordance with the methods of the present disclosure.

For example, some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configure to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

In one aspect, there is provided a method for specifically detecting *Babesia* species nucleic acid in a sample, which comprises the use of at least two amplification oligomers comprising (a) a first amplification oligomer comprising a first target-hybridizing sequence (i) that is from about 15 to about 33 contiguous nucleotides in length, is contained in the sequence of SEQ ID NO:66 and comprises SEQ ID NO:56 or 57; or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises or consists of SEQ ID NO:8; (v) comprises or consists of SEQ ID NO:83 and (b) a second amplification oligomer comprising a second target-hybridizing sequence that is from about 15 to about 33 contiguous nucleotides in length, and (i) is contained in SEQ ID NO:68 and comprises SEQ ID NO:52, SEQ ID NO:53, SEQ ID NO:54, SEQ ID NO:55, or SEQ ID NO:85; or (ii) is contained in SEQ ID NO:67 and comprises SEQ ID NO:45 or SEQ ID NO:52; or (iii) is contained in SEQ ID NO:70 and comprises SEQ ID NO:46, SEQ ID NO:47, SEQ ID NO:48, SEQ ID NO:49, SEQ ID NO:50, or SEQ ID NO:51; or (iv) comprises or consists of SEQ ID NO:84. In certain embodiments comprising an amplification-based detection assay, a combination of at least two amplification oligomers is therefore utilized for the detection of a *Babesia* sp. nucleic acid.

Suitably, the first amplification oligomer comprises or consists of a sequence selected from the group consisting of: SEQ ID NOs:2 and 4 and 6 and 8 and 83, more suitably, wherein the first amplification oligomer comprises or consists of the sequence selected from the group consisting of: SEQ ID NOs:2 and 4 and 8 and 83.

The first amplification oligomer of the combination may be a promoter primer or promoter provider further comprising a promoter sequence located 5' to the first target-hybridizing sequence. Suitably, the promoter sequence is a T7 promoter sequence which optionally comprises or consists of SEQ ID NO:58. According to this embodiment, the first amplification oligomer may comprise or consist of a sequence selected from the group consisting of SEQ ID NOs:1 and 3 and 5 and 7 and 82, suitably, wherein the first amplification oligomer comprises or consists of a sequence selected from the group consisting of SEQ ID NOs:1 and 3 and 7 and 82.

Suitably, the second amplification oligomer comprises or consists of a sequence selected from the group consisting of: SEQ ID NOs:13, 16, 17, 18, 19, 20, 21, 27, 28, 29, 31, 32, 33, 34, 35, 36, 84, and 86. More suitably, the second amplification oligomer sequence comprises or consists of SEQ ID NO:21 or SEQ ID NO:27 or SEQ ID NO:34 or SEQ ID NO:84 or SEQ ID NO:86.

In one embodiment, the first and second target-hybridizing sequences respectively comprise or consist of the nucleotide sequences of: (a) SEQ ID NO:2 or 6 and SEQ ID NO:11; (b) SEQ ID NO:4 or 6 and SEQ ID NO:13; (c) SEQ ID NO:4 and SEQ ID NO:16 or SEQ ID NO:17; (d) SEQ ID NO:4 and SEQ ID NO:18 or SEQ ID NO:19; (e) SEQ ID NO:4 and SEQ ID NO:20; (f) SEQ ID NO:4 or 6 or 8 and SEQ ID NO:21; (g) SEQ ID NO:2 or 4 or 8 and SEQ ID NO:27; (h) SEQ ID NO:4 and SEQ ID NO:28; (i) SEQ ID NO:4 and SEQ ID NO:29; (j) SEQ ID NO:4 and SEQ ID NO:31; (k) SEQ ID NO:8 and SEQ ID NO:32; (l) SEQ ID NO:8 and SEQ ID NO:33; (m) SEQ ID NO:8 and SEQ ID NO:34; (n) SEQ ID NO:8 and SEQ ID NO:35; (o) SEQ ID NO:8 and SEQ ID NO:36; (p) SEQ ID NO:8 and SEQ ID NO:84; (q) SEQ ID NO:8 and SEQ ID NO:86; (r) SEQ ID NO:83 and SEQ ID NO:34; (s) SEQ ID NO:83 and SEQ ID NO:84; or (t) SEQ ID NO:83 and SEQ ID NO:86.

In another embodiment, the first and second target-hybridizing sequences respectively comprise or consist of the nucleotide sequences of: (a) SEQ ID NO:2 and SEQ ID NO:27; (b) SEQ ID NO:4 and SEQ ID NO:21; (c) SEQ ID NO:8 and SEQ ID NO:21; (d) SEQ ID NO:8 and SEQ ID NO:34; (e) SEQ ID NO:8 and SEQ ID NO:84; (f) SEQ ID NO:8 and SEQ ID NO:86; (g) SEQ ID NO:83 and SEQ ID NO:34; (h) SEQ ID NO:83 and SEQ ID NO:84; or (i) SEQ ID NO:83 and SEQ ID NO:86.

In embodiments where the combination further includes one or more detection probe oligomers, the first and second amplification oligomer target-hybridizing sequences and the detection probe oligomer target-hybridizing sequences respectively may comprise or consist of the nucleotide sequences of: (a) SEQ ID NO:2 and SEQ ID NO:11 and SEQ ID NO:39 or SEQ ID NO:37; (b) SEQ ID NO:2 and SEQ ID NO:27 and SEQ ID NO:38 or SEQ ID NO:39; (c) SEQ ID NO:4 and SEQ ID NO:13 and SEQ ID NO:39 or SEQ ID NO:37; (d) SEQ ID NO:4 and SEQ ID NO:16 or SEQ ID NO:17 and SEQ ID NO:39; (e) SEQ ID NO:4 and SEQ ID NO:18 or SEQ ID NO:19 and SEQ ID NO:39 or SEQ ID NO:37; (f) SEQ ID NO:4 and SEQ ID NO:20 and SEQ ID NO:39 or SEQ ID NO:37; (g) SEQ ID NO:4 and SEQ ID NO:21 and SEQ ID NO:39 or SEQ ID NO:37; (h) SEQ ID NO:4 and SEQ ID NO:27 and SEQ ID NO:39 or SEQ ID NO:38; (i) SEQ ID NO:4 and SEQ ID NO:28 and SEQ ID NO:39; (j) SEQ ID NO:4 and SEQ ID NO:29 and SEQ ID NO:39 or SEQ ID NO:37; (k) SEQ ID NO:4 and SEQ ID NO:31 and SEQ ID NO:39; (l) SEQ ID NO:6 and SEQ ID NO:11 and SEQ ID NO:37; (m) SEQ ID NO:6 and SEQ ID NO:13 and SEQ ID NO:37; (n) SEQ ID NO:6 and SEQ ID NO:21 and SEQ ID NO:37; (o) SEQ ID NO:8 and SEQ ID NO:21 and SEQ ID NO:39 or SEQ ID NO:37 or SEQ ID NO:42; (p) SEQ ID NO:8 and SEQ ID NO:27 and SEQ ID NO:39; (q) SEQ ID NO:8 and SEQ ID NO:32 and SEQ ID NO:37 or SEQ ID NO:42; (r) SEQ ID NO:8 and SEQ ID NO:33 and SEQ ID NO:37 or SEQ ID NO:42; (s) SEQ ID NO:8 and SEQ ID NO:34 and SEQ ID NO:37 or SEQ ID NO:42; (t) SEQ ID NO:8 and SEQ ID NO:35 and SEQ ID NO:37 or SEQ ID NO:42; (u) SEQ ID NO:8 and SEQ ID NO:36 and SEQ ID NO:37 or SEQ ID NO:42; (v) SEQ ID NO:8, and SEQ ID NO:84, and SEQ ID NOs:91, 92 and/or 93; (w) SEQ ID NO:8, and SEQ ID NO:86, and SEQ ID NOs:91, 92 and/or 93; (x) SEQ ID NO:83, and SEQ ID NO:34, and SEQ ID NOs:91, 92 and/or 93; (y) SEQ ID NOs:83, and SEQ ID NO:84, and SEQ ID NOs:91, 92 and/or 93; (z) SEQ ID NOs:83, and SEQ ID NO:86, and SEQ ID NOs:91, 92 and/or 93; or (aa) SEQ ID NO:8 or 83, SEQ ID NO:34, 84 or 86, and SEQ ID NO:37, 38, 39, 40, 41, 42, 59, 60, 91, 92, 93, 94, 98 or 99.

In other embodiments where the combination further include one or more detection probe oligomers, the first and second amplification oligomer target-hybridizing sequences and the detection probe oligomer target-hybridizing sequences respectively may comprise or consist of the nucleotide sequences of: (a) SEQ ID NO:2 and SEQ ID NO:27 and SEQ ID NO:38; (b) SEQ ID NO:4 and SEQ ID NO:21 and SEQ ID NO:39; (c) SEQ ID NO:8 and SEQ ID NO:21 and SEQ ID NO:37 or SEQ ID NO:39; (d) SEQ ID NO:8 and SEQ ID NO:34 and SEQ ID NO:37 or SEQ ID NO:42; (e) SEQ ID NO:8, and SEQ ID NO:84, and SEQ ID NOs:91, 92 and/or 93; (f) SEQ ID NO:8, and SEQ ID NO:86, and SEQ ID NOs:91, 92 and/or 93; (g) SEQ ID NO:83, and SEQ ID NO:34, and SEQ ID NOs:91, 92 and/or 93; (h) SEQ ID NOs:83, and SEQ ID NO:84, and SEQ ID NOs:91, 92 and/or 93; (i) SEQ ID NOs:83, and SEQ ID NO:86, and SEQ ID NOs:91, 92 and/or 93; or (j) SEQ ID NO:8 or 83, SEQ ID NO:34, 84 or 86, and SEQ ID NO:37, 38, 39, 40, 41, 42, 59, 60, 91, 92, 93, 94, 98 or 99.

As will be appreciated, the present disclosure contemplates the use of various combinations of first and second amplification oligomers, including: a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:53; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:54; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:55; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:85; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:45; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:46; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:47; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:48; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:49; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:50; a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:51; and a first amplification oligomer comprising a first target-hybridizing sequence (i) that is from about 15 to about 33 contiguous nucleotides in length, is contained in the sequence of SEQ ID NO:66 and comprises SEQ ID NO:56 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising or consisting of SEQ ID NO:84.

Further combinations of first and second amplification oligomers, include: a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:53; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:54; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:55; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length, and is contained in SEQ ID NO:68 and comprises SEQ ID NO:85; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:45; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:67 and comprises SEQ ID NO:52; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:46; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:47; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:48; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:49; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:50; a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising a second target-hybridizing sequence that is from about 15 to about 33 contiguous nucleotides in length and is contained in SEQ ID NO:70 and comprises SEQ ID NO:51; and a first amplification oligomer comprising a first target-hybridizing sequence (i) that is from about 15 to about 33 contiguous nucleotides in length, is contained in the sequence of SEQ ID NO:66 and comprises SEQ ID NO:57 or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101, and a second amplification oligomer comprising or consisting of SEQ ID NO:84.

Further combinations of first and second amplification oligomers, include: a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:52; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:53; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:54; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:55; a first amplification oligomer comprising or consisting of SEQ ID NO:8 or 83 and a second amplification oligomer comprising a second target-hybridizing sequence that is from about 15 to about 33 contiguous nucleotides in length, and is contained in SEQ ID NO:68 and comprises SEQ ID NO:85; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:67 and comprises SEQ ID NO:45; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:67 and comprises SEQ ID NO:52; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:46; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:47; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:48; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:49; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:50; a first amplification oligomer comprising or consisting of SEQ ID NO:8 or 83 and a second amplification oligomer comprising a second target-hybridizing sequence that is from about 15 to about 33 contiguous nucleotides in length and is contained in SEQ ID NO:70 and comprises SEQ ID NO:51; and a first amplification oligomer comprising or consisting of SEQ ID NO:8 or 83 and a second amplification oligomer comprising or consisting of SEQ ID NO:84.

The present disclosure also contemplates the use of other combinations of first and second amplification oligomers, including amplification oligomers in which: the first target-hybridizing sequence comprises or consists of SEQ ID NO:2 and the second target-hybridizing sequence comprises or consists of SEQ ID NO:13; the first target-hybridizing sequence comprises or consists of SEQ ID NO:2 and the second target-hybridizing sequence comprises or consists of SEQ ID NO:16; the first target-hybridizing sequence comprises or consists of SEQ ID NO:2 and the second target-hybridizing sequence comprises or consists of SEQ ID NO:17; the first target-hybridizing sequence comprises or consists of SEQ ID NO:2 and the second target-hybridizing sequence comprises or consists of SEQ ID NO:18; the first target-hybridizing sequence comprises or consists of SEQ ID NO:2 and the second target-hybridizing sequence comprises or consists of SEQ ID NO:19; the first target-hybridizing sequence comprises or consists of SEQ ID NO:2 and the second target-hybridizing sequence comprises or consists of SEQ ID NO:20; the first target-hybridizing sequence comprises or consists of SEQ ID NO:2 and the second target-hybridizing sequence comprises or consists of SEQ ID NO:21; the first target-hybridizing sequence comprises or consists of SEQ ID NO:2 and the second target-hybridizing sequence comprises or consists of SEQ ID NO:27; the first target-hybridizing sequence comprises or consists of SEQ ID NO:2 and the second target-hybridizing sequence comprises or consists of SEQ ID NO:28; the first target-hybridizing sequence comprises or consists of SEQ ID NO:2 and the second target-hybridizing sequence comprises or consists of SEQ ID NO:29; the first target-hybridizing sequence comprises or consists of SEQ ID NO:2 and the second target-hybridizing sequence comprises or consists of SEQ ID NO:31; the first target-hybridizing sequence comprises or consists of SEQ ID NO:2 and the second target-hybridizing sequence comprises or consists of SEQ ID NO:32; the first target-hybridizing sequence comprises or consists of SEQ ID NO:2 and the second target-hybridizing sequence comprises or consists of SEQ ID NO:33; the first target-hybridizing sequence comprises or consists of SEQ ID NO:2 and the second target-hybridizing sequence comprises or consists of SEQ ID NO:34; the first target-hybridizing sequence comprises or consists of SEQ ID NO:2 and the second target-hybridizing sequence comprises or consists of SEQ ID NO:35; and the first target-hybridizing sequence comprises or consists of SEQ ID NO:2 and the second target-hybridizing sequence comprises or consists of SEQ ID NO:36.

The present disclosure also contemplates the use of other combinations of first and second amplification oligomers, including amplification oligomers in which: the first target-hybridizing sequence comprises or consists of SEQ ID NO:4 and the second target-hybridizing sequence comprises or consists of SEQ ID NO:13; the first target-hybridizing sequence comprises or consists of SEQ ID NO:4 and the second target-hybridizing sequence comprises or consists of SEQ ID NO:16; the first target-hybridizing sequence comprises or consists of SEQ ID NO:4 and the second target-hybridizing sequence comprises or consists of SEQ ID NO:17; the first target-hybridizing sequence comprises or consists of SEQ ID NO:4 and the second target-hybridizing sequence comprises or consists of SEQ ID NO:18; the first target-hybridizing sequence comprises or consists of SEQ ID NO:4 and the second target-hybridizing sequence comprises or consists of SEQ ID NO:19; the first target-hybridizing sequence comprises or consists of SEQ ID NO:4 and the second target-hybridizing sequence comprises or consists of SEQ ID NO:20; the first target-hybridizing sequence comprises or consists of SEQ ID NO:4 and the second target-hybridizing sequence comprises or consists of SEQ ID NO:21; the first target-hybridizing sequence comprises or consists of SEQ ID NO:4 and the second target-hybridizing sequence comprises or consists of SEQ ID NO:27; the first target-hybridizing sequence comprises or consists of SEQ ID NO:4 and the second target-hybridizing sequence comprises or consists of SEQ ID NO:28; the first target-hybridizing sequence comprises or consists of SEQ ID NO:4 and the second target-hybridizing sequence comprises or consists of SEQ ID NO:29; the first target-hybridizing sequence comprises or consists of SEQ ID NO:4 and the second target-hybridizing sequence comprises or consists of SEQ ID NO:31; the first target-hybridizing sequence comprises or consists of SEQ ID NO:4 and the second target-hybridizing sequence comprises or consists of SEQ ID NO:32; the first target-hybridizing sequence comprises or consists of SEQ ID NO:4 and the second target-hybridizing sequence comprises or consists of SEQ ID NO:33; the first target-hybridizing sequence comprises or consists of SEQ ID NO:4 and the second target-hybridizing sequence comprises or consists of SEQ ID NO:34; the first target-hybridizing sequence comprises or consists of SEQ ID NO:4 and the second target-hybridizing sequence comprises or consists of SEQ ID NO:35; and the first target-hybridizing sequence comprises or consists of SEQ ID NO:4 and the second target-hybridizing sequence comprises or consists of SEQ ID NO:36.

The present disclosure also contemplates the use of other combinations of first and second amplification oligomers, including amplification oligomers in which: the first target-hybridizing sequence comprises or consists of SEQ ID NO:6 and the second target-hybridizing sequence comprises or consists of SEQ ID NO:13; the first target-hybridizing sequence comprises or consists of SEQ ID NO:6 and the second target-hybridizing sequence comprises or consists of SEQ ID NO:16; the first target-hybridizing sequence comprises or consists of SEQ ID NO:6 and the second target-hybridizing sequence comprises or consists of SEQ ID NO:17; the first target-hybridizing sequence comprises or consists of SEQ ID NO:6 and the second target-hybridizing sequence comprises or consists of SEQ ID NO:18; the first target-hybridizing sequence comprises or consists of SEQ ID NO:6 and the second target-hybridizing sequence comprises or consists of SEQ ID NO:19; the first target-hybridizing sequence comprises or consists of SEQ ID NO:6 and the second target-hybridizing sequence comprises or consists of SEQ ID NO:20; the first target-hybridizing sequence comprises or consists of SEQ ID NO:6 and the second target-hybridizing sequence comprises or consists of SEQ ID NO:21; the first target-hybridizing sequence comprises or consists of SEQ ID NO:6 and the second target-hybridizing sequence comprises or consists of SEQ ID NO:27; the first target-hybridizing sequence comprises or consists of SEQ ID NO:6 and the second target-hybridizing sequence comprises or consists of SEQ ID NO:28; the first target-hybridizing sequence comprises or consists of SEQ ID NO:6 and the second target-hybridizing sequence comprises or consists of SEQ ID NO:29; the first target-hybridizing sequence comprises or consists of SEQ ID NO:6 and the second target-hybridizing sequence comprises or consists of SEQ ID NO:31; the first target-hybridizing sequence comprises or consists of SEQ ID NO:6 and the second target-hybridizing sequence comprises or consists of SEQ ID NO:32; the first target-hybridizing sequence comprises or consists of SEQ ID NO:6 and the second target-hybridizing sequence comprises or consists of SEQ ID NO:33; the first target-hybridizing sequence comprises or consists of SEQ ID NO:6 and the second target-hybridizing sequence comprises or consists of SEQ ID NO:34; the first target-hybridizing sequence comprises or consists of SEQ ID NO:6 and the second target-hybridizing sequence comprises or consists of SEQ ID NO:35; and the first target-hybridizing sequence comprises or consists of SEQ ID NO:6 and the second target-hybridizing sequence comprises or consists of SEQ ID NO:36.

The present disclosure also contemplates the use of other combinations of first and second amplification oligomers, including amplification oligomers in which: the first target-hybridizing sequence comprises or consists of SEQ ID NO:8 and the second target-hybridizing sequence comprises or consists of SEQ ID NO:13; the first target-hybridizing sequence comprises or consists of SEQ ID NO:8 and the second target-hybridizing sequence comprises or consists of SEQ ID NO:16; the first target-hybridizing sequence comprises or consists of SEQ ID NO:8 and the second target-hybridizing sequence comprises or consists of SEQ ID NO:17; the first target-hybridizing sequence comprises or consists of SEQ ID NO:8 and the second target-hybridizing sequence comprises or consists of SEQ ID NO:18; the first target-hybridizing sequence comprises or consists of SEQ ID NO:8 and the second target-hybridizing sequence comprises or consists of SEQ ID NO:19; the first target-hybridizing sequence comprises or consists of SEQ ID NO:8 and the second target-hybridizing sequence comprises or consists of SEQ ID NO:20; the first target-hybridizing sequence comprises or consists of SEQ ID NO:8 and the second target-hybridizing sequence comprises or consists of SEQ ID NO:21; the first target-hybridizing sequence comprises or consists of SEQ ID NO:8 and the second target-hybridizing sequence comprises or consists of SEQ ID NO:27; the first target-hybridizing sequence comprises or consists of SEQ ID NO:8 and the second target-hybridizing sequence comprises or consists of SEQ ID NO:28; the first target-hybridizing sequence comprises or consists of SEQ ID NO:8 and the second target-hybridizing sequence comprises or consists of SEQ ID NO:29; the first target-hybridizing sequence comprises or consists of SEQ ID NO:8 and the second target-hybridizing sequence comprises or consists of SEQ ID NO:31; the first target-hybridizing sequence comprises or consists of SEQ ID NO:8 and the second target-hybridizing sequence comprises or consists of SEQ ID NO:32; the first target-hybridizing sequence comprises or consists of SEQ ID NO:8 and the second target-hybridizing sequence comprises or consists of SEQ ID NO:33; the first target-hybridizing sequence comprises or consists of SEQ ID NO:8 and the second target-hybridizing sequence comprises or consists of SEQ ID NO:34; the first target-hybridizing sequence comprises or consists of SEQ ID NO:8 and the second target-hybridizing sequence comprises or consists of SEQ ID NO:35; the first target-hybridizing sequence comprises or consists of SEQ ID NO:8 and the second target-hybridizing sequence comprises or consists of SEQ ID NO:36; the first target-hybridizing sequence comprises or consists of SEQ ID NO:8 and the second target-hybridizing sequence comprises or consists of SEQ ID NO:84; and the first target-hybridizing sequence comprises or consists of SEQ ID NO:8 and the second target-hybridizing sequence comprises or consists of SEQ ID NO:86.

The present disclosure also contemplates the use of other combinations of first and second amplification oligomers, including amplification oligomers in which: the first target-hybridizing sequence comprises or consists of SEQ ID NO:83 and the second target-hybridizing sequence comprises or consists of SEQ ID NO:13; the first target-hybridizing sequence comprises or consists of SEQ ID NO:83 and the second target-hybridizing sequence comprises or consists of SEQ ID NO:16; the first target-hybridizing sequence comprises or consists of SEQ ID NO:83 and the second target-hybridizing sequence comprises or consists of SEQ ID NO:17; the first target-hybridizing sequence comprises or consists of SEQ ID NO:83 and the second target-hybridizing sequence comprises or consists of SEQ ID NO:18; the first target-hybridizing sequence comprises or consists of SEQ ID NO:83 and the second target-hybridizing sequence comprises or consists of SEQ ID NO:19; the first target-hybridizing sequence comprises or consists of SEQ ID NO:83 and the second target-hybridizing sequence comprises or consists of SEQ ID NO:20; the first target-hybridizing sequence comprises or consists of SEQ ID NO:83 and the second target-hybridizing sequence comprises or consists of SEQ ID NO:21; the first target-hybridizing sequence comprises or consists of SEQ ID NO:83 and the second target-hybridizing sequence comprises or consists of SEQ ID NO:27; the first target-hybridizing sequence comprises or consists of SEQ ID NO:83 and the second target-hybridizing sequence comprises or consists of SEQ ID NO:28; the first target-hybridizing sequence comprises or consists of SEQ ID NO:83 and the second target-hybridizing sequence comprises or consists of SEQ ID NO:29; the first target-hybridizing sequence comprises or consists of SEQ ID NO:83 and the second target-hybridizing sequence comprises or consists of SEQ ID NO:31; the first target-hybridizing sequence comprises or consists of SEQ ID NO:83 and the second target-hybridizing sequence comprises or consists of SEQ ID NO:32; the first target-hybridizing sequence comprises or consists of SEQ ID NO:83 and the second target-hybridizing sequence comprises or consists of SEQ ID NO:33; the first target-hybridizing sequence comprises or consists of SEQ ID NO:83 and the second target-hybridizing sequence comprises or consists of SEQ ID NO:34; the first target-hybridizing sequence comprises or consists of SEQ ID NO:83 and the second target-hybridizing sequence comprises or consists of SEQ ID NO:35; the first target-hybridizing sequence comprises or consists of SEQ ID NO:83 and the second target-hybridizing sequence comprises or consists of SEQ ID NO:36; the first target-hybridizing sequence comprises or consists of SEQ ID NO:83 and the second target-hybridizing sequence comprises or consists of SEQ ID NO:84; and the first target-hybridizing sequence comprises or consists of SEQ ID NO:83 and the second target-hybridizing sequence comprises or consists of SEQ ID NO:86.

The present disclosure also contemplates the use of other combinations of first and second amplification oligomers, wherein the first and second target-hybridizing sequences respectively comprise or consist of the nucleotide sequences of: SEQ ID NO:2 and SEQ ID NO:11; SEQ ID NO:6 and SEQ ID NO:11; SEQ ID NO:4 and SEQ ID NO:13; SEQ ID NO:6 and SEQ ID NO:13; SEQ ID NO:4 and SEQ ID NO:16; SEQ ID NO:4 and SEQ ID NO:17; SEQ ID NO:4 and SEQ ID NO:18; SEQ ID NO:4 and SEQ ID NO:19; SEQ ID NO:4 and SEQ ID NO:20; SEQ ID NO:4 and SEQ ID NO:21; SEQ ID NO:6 and SEQ ID NO:21; SEQ ID NO:8 and SEQ ID NO:21; SEQ ID NO:2 and SEQ ID NO:27; SEQ ID NO:4 and SEQ ID NO:27; SEQ ID NO:8 and SEQ ID NO:27; SEQ ID NO:4 and SEQ ID NO:28; SEQ ID NO:4 and SEQ ID NO:29; SEQ ID NO:4 and SEQ ID NO:31; SEQ ID NO:8 and SEQ ID NO:32; SEQ ID NO:8 and SEQ ID NO:33; SEQ ID NO:8 and SEQ ID NO:34; SEQ ID NO:8 and SEQ ID NO:84; SEQ ID NO:8 and SEQ ID NO:86; SEQ ID NO:8 and SEQ ID NO:35; SEQ ID NO:8 and SEQ ID NO:36; SEQ ID NO:83 and SEQ ID NO:32; SEQ ID NO:83 and SEQ ID NO:33; SEQ ID NO:83 and SEQ ID NO:34; SEQ ID NO:83 and SEQ ID NO:84; SEQ ID NO:83 and SEQ ID NO:86; SEQ ID NO:83 and SEQ ID NO:35; or SEQ ID NO:83 and SEQ ID NO:36.

The present disclosure also contemplates the use of combinations of a first amplification oligomer, a second amplification oligomer and a detection probe in which the first and second amplification oligomer target-hybridizing sequences and the detection probe oligomer target-hybridizing sequences respectively comprise or consist of the nucleotide sequences of: SEQ ID NO:2 and SEQ ID NO:11 and SEQ ID NO:39; SEQ ID NO:2 and SEQ ID NO:11 and SEQ ID NO:37; SEQ ID NO:2 and SEQ ID NO:27 and SEQ ID NO:38; SEQ ID NO:2 and SEQ ID NO:27 and SEQ ID NO:39; SEQ ID NO:4 and SEQ ID NO:13 and SEQ ID NO:39; SEQ ID NO:4 and SEQ ID NO:13 and SEQ ID NO:37; SEQ ID NO:4 and SEQ ID NO:16 and SEQ ID NO:39; SEQ ID NO:4 and SEQ ID NO:17 and SEQ ID NO:39; SEQ ID NO:4 and SEQ ID NO:18 and SEQ ID NO:39; SEQ ID NO:4 and SEQ ID NO:19 and SEQ ID NO:39; SEQ ID NO:4 and SEQ ID NO:18 and SEQ ID NO:37; SEQ ID NO:4 and SEQ ID NO:19 and SEQ ID NO:37; SEQ ID NO:4 and SEQ ID NO:20 and SEQ ID NO:39; SEQ ID NO:4 and SEQ ID NO:20 and SEQ ID NO:37; SEQ ID NO:4 and SEQ ID NO:21 and SEQ ID NO:39; SEQ ID NO:4 and SEQ ID NO:21 and SEQ ID NO:37; SEQ ID NO:4 and SEQ ID NO:27 and SEQ ID NO:39; SEQ ID NO:4 and SEQ ID NO:27 and SEQ ID NO:38; SEQ ID NO:4 and SEQ ID NO:28 and SEQ ID NO:39; SEQ ID NO:4 and SEQ ID NO:29 and SEQ ID NO:39; SEQ ID NO:4 and SEQ ID NO:29 and SEQ ID NO:37; SEQ ID NO:4 and SEQ ID NO:31 and SEQ ID NO:39; SEQ ID NO:6 and SEQ ID NO:11 and SEQ ID NO:37; SEQ ID NO:6 and SEQ ID NO:13 and SEQ ID NO:37; SEQ ID NO:6 and SEQ ID NO:21 and SEQ ID NO:37; SEQ ID NO:8 and SEQ ID NO:21 and SEQ ID NO:39; SEQ ID NO:8 and SEQ ID NO:21 and SEQ ID NO:37; SEQ ID NO:8 and SEQ ID NO:21 and SEQ ID NO:42; SEQ ID NO:8 and SEQ ID NO:27 and SEQ ID NO:39; SEQ ID NO:8 and SEQ ID NO:32 and SEQ ID NO:37; SEQ ID NO:8 and SEQ ID NO:32 and SEQ ID NO:42; SEQ ID NO:8 and SEQ ID NO:33 and SEQ ID NO:37; SEQ ID NO:8 and SEQ ID NO:33 and SEQ ID NO:42; SEQ ID NO:8 and SEQ ID NO:34 and SEQ ID NO:37; SEQ ID NO:8 and SEQ ID NO:34 and SEQ ID NO:42; SEQ ID NO:8 and SEQ ID NO:35 and SEQ ID NO:37; SEQ ID NO:8 and SEQ ID NO:35 and SEQ ID NO:42; SEQ ID NO:8 and SEQ ID NO:36 and SEQ ID NO:37; or SEQ ID NO:8 and SEQ ID NO:36 and SEQ ID NO:42; SEQ ID NO:8, and SEQ ID NO:84, and SEQ ID NOs:91, 92 and/or 93; SEQ ID NO:8, and SEQ ID NO:86, and SEQ ID NOs:91, 92 and/or 93; SEQ ID NO:83, and SEQ ID NO:34, and SEQ ID NOs:91, 92 and/or 93; SEQ ID NOs:83, and SEQ ID NO:84, and SEQ ID NOs:91, 92 and/or 93; SEQ ID NOs:83, and SEQ ID NO:86, and SEQ ID NOs:91, 92 and/or 93; or SEQ ID NO:8 or 83, SEQ ID NO:34, 84 or 86, and SEQ ID NO:37, 38, 39, 40, 41, 42, 59, 60, 91, 92, 93, 94, 98 or 99.

In a further aspect, there is described a method for specifically detecting *Babesia* species nucleic acid in a sample, said method comprising: (1) contacting a sample, said sample suspected of containing *Babesia* species nucleic acid, with at least two oligomers for amplifying a target region of a *Babesia* species target nucleic acid, wherein two of said at least two amplification oligomers are selected from the group consisting of: (a) a first amplification oligomer and a second amplification oligomer, wherein the first amplification oligomer comprises a first target-hybridizing sequence (i) that is from 15 to 33 contiguous nucleobases in length, is contained in SEQ ID NO:66 and contains SEQ ID NO:56 or SEQ ID NO:57, or (ii) that is from about 15 to about 33 contiguous nucleotides in length, is contained in the sequence of SEQ ID NO:96 and comprises SEQ ID NO:101; or (iii) that is from about 15 to about 33 contiguous nucleotides in length, is contained in the sequence of SEQ ID NO:97 and comprises SEQ ID NO:101; (iv) comprises/consists of SEQ ID NO:8 or 83; or (b) a first amplification oligomer and a second amplification oligomer, wherein the second amplification oligomer comprises a second target-hybridizing sequence that is from about 15 to about 33 contiguous nucleotides in length, and is (i) contained in SEQ ID NO:68 and contains SEQ ID NO:52, SEQ ID NO:53 SEQ ID NO:54, SEQ ID NO:55, or SEQ ID NO:85, or (ii) is contained in SEQ ID NO:67 and contains SEQ ID NO:45 or SEQ ID NO:69, or (iii) is contained in SEQ ID NO:70 and contains SEQ ID NO:46, SEQ ID NO:47, SEQ ID NO:48, SEQ ID NO:49, SEQ ID NO:50, or SEQ ID NO:51; or (iv) comprises or consists of SEQ ID NO:84; (2) performing an in vitro nucleic acid amplification reaction, wherein any *Babesia* target nucleic acid present in said sample is used as a template for generating an amplification product, wherein said amplification product has a length of from 180 to 220 contiguous nucleotides and contains SEQ ID NO:65 or the complement thereof; and (3) detecting the presence or absence of the amplification product, thereby indicating the presence or absence of *Babesia* species target nucleic acid in said sample.

In those embodiments in which the amplification product has a length of from 180 to 220 contiguous nucleotides and contains SEQ ID NO:65 or the complement thereof it is also contemplated that the amplification product has a length of from 180 to 210 contiguous nucleotides and contains SEQ ID NO:65 or the complement thereof. It is also contemplated that the amplification product has a length of from 180 to 200 contiguous nucleotides and contains SEQ ID NO:65 or the complement thereof. It is also contemplated that the amplification product has a length of from 180 to 190 contiguous nucleotides and contains SEQ ID NO:65 or the complement thereof. It is also contemplated that the amplification product has a length of from 190 to 220 contiguous nucleotides and contains SEQ ID NO:65 or the complement thereof. It is also contemplated that the amplification product has a length of from 200 to 220 contiguous nucleotides and contains SEQ ID NO:65 or the complement thereof. It is also contemplated that the amplification product has a length of from 210 to 220 contiguous nucleotides and contains SEQ ID NO:65 or the complement thereof.

Further combinations of first and second amplification oligomers therefore also include those in which the first amplification oligomer comprises a first target-hybridizing sequence that is from 15 to 33 contiguous nucleobases in length, is contained in SEQ ID NO:66 and contains SEQ ID NO:56; or comprises a first target-hybridizing sequence that is from 15 to 33 contiguous nucleobases in length, is contained in SEQ ID NO:66 and contains SEQ ID NO:57; or comprises a first target hybridizing sequence that is from 15 to 33 contiguous nucleotides in length, is contained in the sequence of SEQ ID NO:96 and contains SEQ ID NO:101; or comprises a first target-hybridizing sequence from 15 to 33 contiguous nucleotides in length, is contained in the sequence of SEQ ID NO:97 and contains SEQ ID NO:101; or comprises or consists of SEQ ID NO:8.

Further combinations of first and second amplification oligomers therefore also include those in which the second amplification oligomer comprises a second target-hybridizing sequence that is from about 15 to about 33 contiguous nucleotides in length and is contained in SEQ ID NO:68 and contains SEQ ID NO:52, or contains SEQ ID NO:53 or contains SEQ ID NO:54 or contains SEQ ID NO:55 or contains SEQ ID NO:85.

Further combinations of first and second amplification oligomers therefore also include those in which the second amplification oligomer comprises a second target-hybridizing sequence that is from about 15 to about 33 contiguous nucleotides in length and is contained in SEQ ID NO:67 and contains SEQ ID NO:45 or contains SEQ ID NO:69.

Further combinations of first and second amplification oligomers therefore also include those in which the second amplification oligomer comprises a second target-hybridizing sequence that is from about 15 to about 33 contiguous nucleotides in length and is contained in SEQ ID NO:70 and contains SEQ ID NO:46 or contains SEQ ID NO:47 or contains SEQ ID NO:48 or contains SEQ ID NO:49 or contains SEQ ID NO:50 or contains SEQ ID NO:51.

Further combinations of first and second amplification oligomers therefore also include those in which the second amplification oligomer comprises a second target-hybridizing sequence that is from about 15 to about 33 contiguous nucleotides in length and contains SEQ ID NO:84.

In some embodiments, combinations of certain first and second amplification oligomers are preferred.

One preferred combination is a first amplification oligomer comprising a first target-hybridizing sequence that is from 15 to 33 contiguous nucleobases in length, is contained in SEQ ID NO:66 and comprises SEQ ID NO:56 or SEQ ID NO:57 and a second amplification oligomer comprising a second target-hybridizing sequence that is contained in SEQ ID NO:67 and comprises SEQ ID NO:45. A more preferred combination is a first amplification oligomer comprising or consisting of the sequence set forth in SEQ ID NO:1 or comprising or consisting of the target-hybridizing sequence set forth in SEQ ID NO:2 and a second amplification oligomer comprising or consisting of the target-hybridizing sequence set forth in SEQ ID NO:27. According to this embodiment, these combinations of first and second amplification oligomers can be used in combination with a detection probe, suitably, a detection probe in which the target hybridising sequence comprises or consists of the sequence set forth in SEQ ID NO:38.

Another preferred combination is a first amplification oligomer comprising a first target-hybridizing sequence that is from 15 to 33 contiguous nucleobases in length, is contained in the sequence of SEQ ID NO:66 and comprises SEQ ID NO:56 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:3 or the target-hybridising sequence set forth in SEQ ID NO:4 and a second amplification oligomer comprising or consisting of the target-hybridising sequence set forth in SEQ ID NO:21. According to this embodiment, these combinations of first and second amplification oligomers can be used in combination with a detection probe, suitably, a detection probe in which the target hybridising sequence comprises or consists of the sequence set forth in SEQ ID NO:39.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence that is contained in SEQ ID NO:68 and comprises SEQ ID NO:52, SEQ ID NO:53, SEQ ID NO:54, SEQ ID NO:55, or SEQ ID NO:85. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35, 36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35, 36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence comprising or consisting of SEQ ID NO:84. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35, 36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridising sequence that is from 15 to 33 contiguous nucleobases in length, is contained in the sequence of SEQ ID NO:97 and comprises SEQ ID NO:101 and a second amplification oligomer comprising a second target-hybridizing sequence that is contained in SEQ ID NO:68 and comprises SEQ ID NO:52, SEQ ID NO:53, SEQ ID NO:54, SEQ ID NO:55, or SEQ ID NO:85. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35, 36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridising sequence that is from 15 to 33 contiguous nucleobases in length, is contained in the sequence of SEQ ID NO:97 and comprises SEQ ID NO:101 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35, 36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridising sequence that is from 15 to 33 contiguous nucleobases in length, is contained in the sequence of SEQ ID NO:97 and comprises SEQ ID NO:101 and a second amplification oligomer comprising a second target-hybridizing sequence comprising or consisting of SEQ ID NO:84. A more preferred combination is a first amplification oligomer comprising or consisting of the sequence set forth in SEQ ID NO:7 or 82 or the target-hybridising sequence set forth in SEQ ID NO:8 or 83 and a second amplification oligomer comprising or consisting of the target-hybridising sequence set forth in SEQ ID NO:13, 16, 17, 18, 19, 20, 21, 27, 28, 29, 31, 32, 33, 34, 35, 36, 84, or 86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer in which the target-hybridizing sequence comprises or consists of SEQ ID NO:8 or SEQ ID NO:83 and a second amplification oligomer comprising a second target-hybridizing sequence that is contained in SEQ ID NO:70 and comprises SEQ ID NO:49 or SEQ ID NO:50, or SEQ ID NO:51. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:21. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer in which the target-hybridizing sequence comprises or consists of SEQ ID NO:8 or SEQ ID NO:83 and a second amplification oligomer comprising a second target-hybridizing sequence that is contained in SEQ ID NO:70 and comprises SEQ ID NO:46 or SEQ ID NO:47 or SEQ ID NO:48 or SEQ ID NO:49 or SEQ ID NO:50 or SEQ ID NO:51. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:34 or SEQ ID NO:84 or SEQ ID NO:86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:96 and comprises SEQ ID NO:101 and a second amplification oligomer comprising a second target-hybridizing sequence that is from about 15 to about 33 contiguous nucleotides in length, and is contained in SEQ ID NO:68 and comprises SEQ ID NO:85. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:34 or SEQ ID NO:84 or SEQ ID NO:86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Another preferred combination is a first amplification oligomer comprising a first target-hybridizing sequence that is from 15 to 33 contiguous nucleobases in length, is contained in the sequence of SEQ ID NO:97 and comprises SEQ ID NO:101 and a second amplification oligomer comprising a second target-hybridizing sequence that is from about 15 to about 33 contiguous nucleotides in length, and is contained in SEQ ID NO:68 and comprises SEQ ID NO:85. A more preferred combination is a first amplification oligomer comprising or consisting of the sequence set forth in SEQ ID NO:7 or SEQ ID NO:8 or SEQ ID NO:82 or SEQ ID NO:83 and a second amplification oligomer comprising or consisting of the sequence set forth in SEQ ID NO:34 or SEQ ID NO:84 or SEQ ID NO:86. According to this embodiment, these combinations of first and second amplification oligomers can be used in combination with a detection probe, suitably, a detection probe in which the target hybridising sequence comprises or consists of the sequence set forth in SEQ ID NO:37, 38, 39, 40, 41, 42, 59, 60, 91, 92, 93, 94, 98 or 99.

Detection of the amplified products may be accomplished by a variety of methods to detect a signal specifically associated with the amplified target sequence. The nucleic acids may be associated with a surface that results in a physical change, such as a detectable electrical change Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample.

Detection probes (where labelled) that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified sequences may be unlabeled and detected indirectly (e.g., by binding of another binding partner to a moiety on the probe) or may be labeled with a variety of detectable labels. In some embodiments of the method for diagnosing BV, such as in certain embodiments using transcription-mediated amplification (TMA), the detection probe is a linear chemiluminescently labeled probe such as, e.g., a linear acridinium ester (AE) labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174).

In embodiments that detect the amplified product near or at the end of the amplification step, a linear detection probe may be used to provide a signal to indicate hybridization of the probe to the amplified product. One example of such detection uses a luminescentally labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1).

In certain embodiments comprising an amplification-based detection assay targeting Babesia sp., the method utilizes one or more detection probes that specifically hybridizes to a Babesia sp. amplification product. In particular variations, a Babesia sp.-specific detection probe oligomer comprises a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence contains the sequence of SEQ ID NO:59 and includes at least the sequence of SEQ ID NO:37, 42, or 99.

Suitably, the detection probe target-hybridizing sequence is contained in the sequence of SEQ ID NO:65 and includes at least the sequence of SEQ ID NO:59, 94, or 99.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence comprising or consisting of SEQ ID NO:59, 94, or 99.

Suitably, the detection probe target hybridising sequence consists of the sequence selected from the group consisting of: SEQ ID NOs:37, 38, 39, 40, 41, 42, 59, 60, 91, 92, 93, 94, 98 or 99.

Suitably, the detection probe oligomer further comprises a 2' methoxy modification on at least one nucleotide residue member of the nucleotide sequence.

In some embodiments of a method comprising the use of a nucleic-acid-base detection assay, a non-amplification-based assay is used to detect Babesia sp. In some such embodiments, the non-amplification-based assay is a hybridization assay comprising the hybridization of a specific detection probe to a target nucleic acid. Methods for conducting polynucleotide hybridization assays have been well developed in the art. Hybridization assay procedures and conditions will vary depending on the application and are selected in accordance with the general binding methods known, including those referred to in, e.g., Maniatis et al, Molecular Cloning: A Laboratory Manual (3rd ed. Cold Spring Harbor, N.Y., 2002), and Berger and Kimmel, Methods in Enzymology, Vol. 152, Guide to Molecular Cloning Techniques (Academic Press, Inc., San Diego, Calif., 1987). Generally, the probe and sample are mixed under conditions that will permit specific nucleic acid hybridization, and specific hybridization of the probe to its respective target is then detected. Nucleic acid hybridization is adaptable to a variety of assay formats. One suitable format is the sandwich assay format, which is particularly adaptable to hybridization under non-denaturing conditions. A primary component of a sandwich-type assay is a solid support, which has adsorbed to it or covalently coupled to it immobilized nucleic acid probe that is unlabeled and complementary to one portion of the DNA sequence. Target nucleic acid is hybridized to the immobilized probe, and a second, labeled detection probe—which is complementary to a second and different region of the same DNA strand to which the immobilized, unlabeled nucleic acid probe is hybridized—is hybridized to the [target nucleic acid]:[immobilized probe] duplex to detect the target nucleic acid. Another exemplary format utilizes electrochemical detection of target nucleic acids hybridized to unlabeled detection probes immobilized on a suitable electrode surface as a signal transducer. See, e.g., Drummond et al., Nat. Biotechnol. 21: 1192, 2003; Gooding, Electroanalysis 14: 1149, 2002; Wang, Anal. Chim Acta 469:63, 2002; Cagnin et al., Sensors 9:3122, 2009; Katz and Willner, Electroanalysis 15:913, 2003; Daniels and Pourmand, Electroanalysis 19: 1239, 2007.

In certain embodiments comprising a hybridization assay, a detection probe is utilized for the detection of a *Babesia* sp. In such embodiments, a detection probe oligomer for detecting *Babesia* sp. comprises a target-hybridizing sequence that is from about 14 to about 40 nucleotides in length and is configured to specifically hybridize to a target sequence contained in SEQ ID NO:59, the RNA equivalent of SEQ ID NO:59, the complement of SEQ ID NO:59, the RNA equivalent of the complement of SEQ ID NO:59, SEQ ID NO:65, the DNA equivalent of SEQ ID NO:65, the complement of SEQ ID NO:65, or the DNA equivalent of the complement of SEQ ID NO:65.

Suitably, the detection probe target-hybridizing sequence is contained in the sequence of SEQ ID NO:59 and includes at least the sequence of SEQ ID NO:42, 92, 94, or 99.

Suitably, the detection probe target-hybridizing sequence contains the sequence of SEQ ID NO:59 and includes at least the sequence of SEQ ID NO:37, 42, or 99.

Suitably, the detection probe target-hybridizing sequence is contained in the sequence of SEQ ID NO:65 and includes at least the sequence of SEQ ID NO:59, 94 or 99.

Suitably, the detection probe oligomer comprises a nucleotide sequence that is from 16 to 25 contiguous nucleotides in length and specifically hybridizes to SEQ ID NO:65, or the DNA equivalent thereof; or specifically hybridizes to the complement of SEQ ID NO:65, or the DNA equivalent thereof.

Suitably, the detection probe oligomer sequence further comprises a nucleotide sequence containing SEQ ID NO:59, 94, or 99.

Suitably, the detection probe target hybridising sequence consists of the sequence selected from the group consisting of: SEQ ID NO:37, 38, 39, 40, 41, 42, 59, 60, 91, 92, 93, 94, 98 or 99.

Suitably, the detection probe oligomer further comprises a 2' methoxy modification on at least one nucleotide residue member of the nucleotide sequence.

In some embodiments, a non-amplification-based assay for detection of *Babesia* sp. is a cleavage-based assay, in which a probe oligonucleotide containing a non-target-hybridizing flap region is cleaved in an overlap-dependent manner by a flap endonuclease to release a cleavage product that is then detected. Exemplary cleavage-based assay reagents are described in, e.g., Lyamichev et al. (Nat. Biotechnol. 17:292-296, 1999), Ryan et al. (Mol. Diagn. 4: 135-144, 1999), and Allawi et al. (J. Clin. Microbiol. 44:3443-3447, 2006).

Appropriate conditions for flap endonuclease reactions are either known or can be readily determined using methods known in the art (see, e.g., Kaiser et al, J. Biol. Chem. 274:2138-721394, 1999). Exemplary flap endonucleases that may be used in the method include *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus fiiriosus* FEN-1, *Methanobacterium thermoautotrophicum* FEN-1, *Thermus thermophilus* FEN-1, CLEAVASE® (Hologic, Inc., Madison, WI), *S. cerevisiae* RTH1, *S. cerevisiae* RAD27, *Schizosaccharomyces pombe* rad2, bacteriophage T5 5'-3' exonuclease, *Pyrococcus horikoshii* FEN-1, human endonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of flap endonucleases can be found in, for example, Lyamichev et al., Science 260:778-783, 1993; Eis et al, Nat. Biotechnol. 19:673-676, 2001; Shen et al, Trends in Bio. Sci. 23: 171-173, 1998; Kaiser et al, J. Biol. Chem. 274:21387-21394, 1999; Ma et al, J. Biol. Chem. 275:24693-24700, 2000; Allawi et al, J. Mol. Biol. 328:537-554, 2003; Sharma et al, J. Biol. Chem. 278:23487-23496, 2003; and Feng et al, Nat. Struct. Mol. Biol. 11:450-456, 2004.

In certain variations, a cleavage-based assay detects an RNA target nucleic acid of *Babesia* sp., and the cleavage-based assay utilizes a flap endonuclease that is capable of cleaving and RNA:DNA linear duplex structure. In some alternative embodiments, a cleavage-based assay detects a DNA target nucleic acid of *Babesia* sp., and the cleavage-based assay utilizes a flap endonuclease that is capable of cleaving and DNA:DNA linear duplex structure. Exemplary flap endonucleases capable of cleaving RNA:DNA duplexes include polymerase-deficient 5' nucleases of the genus *Thermus* as well as certain CLEAVASE® enzymes (Hologic, Inc., Madison, WI) such as, for example, CLEAVASE® BN (BstX-Notl deletion of Taq polymerase, see U.S. Pat. No. 5,614,402), CLEAVASE® II ("AG" mutant of full length Taq polymerase, see U.S. Pat. No. 5,614,402), CLEAVASE® VII (synthesis-deficient mutation of full length *Thermus thermophilus* polymerase), CLEAVASE® IX (polymerase deficient mutant of the Tth DNA polymerase), and CLEAVASE® XII (polymerase deficient chimeric polymerase constructed from fragments of taq DNA polymerase and Tth DNA polymerase). Exemplary flap endonucleases capable of cleaving DNA:DNA duplexes include the flap endonucleases indicated above, as well as CLEAVASE® 2.0 (*Archaeoglobus fulgidus* FEN-1), CLEAVASE® 2.1 (*Archaeoglobus fulgidus* FEN-1 with 6 histidines on the C-terminus), CLEAVASE® 3.0 (*Archaeoglobus veneficus* FEN-1), and CLEAVASE® 3.1 (*Archaeoglobus veneficus* FEN-1 with 6 histidines on the C-terminus).

In some embodiments, a cleavage-based assay detects an RNA target nucleic acid of *Babesia* sp., and the assay includes a step for synthesizing a DNA complement of an RNA target region, which cDNA strand is then hybridized to overlapping first and second probe oligonucleotides to form a linear duplex cleavage structure for cleavage by the flap endonuclease. Reaction conditions for synthesizing cDNA from an RNA template, using an RNA-dependent DNA polymerase (reverse transcriptase), are well-known in the art.

In certain embodiments utilizing a nucleic-acid-based detection assay, the method further includes purifying the *Babesia* sp. target nucleic acid from other components in the sample. Such purification may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Babesia* sp. nucleic acid and other sample components.

In some embodiments, a target nucleic acid of *Babesia* sp. is separated from other sample components by hybridizing the target nucleic acid to a capture probe oligomer. The capture probe oligomer comprises a target-hybridizing sequence configured to specifically or non-specifically hybridize to a target nucleic acid so as to form a [target nucleic acid]:[capture probe] complex that is separated from other sample components. Capture probes comprising target-hybridizing sequences suitable for non-specific capture of target nucleic acids are described in, e.g., WO 2008/016988. In some specific variations comprising target-hybridizing sequence(s) configured to specifically hybridize to a *Babesia* sp. target nucleic acid, a *Babesia*-specific capture probe comprises a target-hybridizing sequence that (i) is from about 15 to about 21 contiguous nucleotides contained in the sequence of SEQ ID NO:78, or (ii) is about 21 to 30 contiguous nucleotides comprising the sequence of SEQ ID NO:78; or (iii) the sequence consists of SEQ ID NO:44. In a preferred variation, the capture probe binds the [target nucleic acid]:[capture probe] complex to an immobilized probe to form a [target nucleic acid]:[capture probe]:[immobilized probe] complex that is separated from the sample and, optionally, washed to remove non-target sample components (see, e.g., U.S. Pat. Nos. 6,110,678; 6,280,952; and 6,534,273). In such variations, the capture probe oligomer further comprises a sequence or moiety that binds the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to target nucleic acid but that specifically hybridizes to a sequence on the immobilized probe, thereby serving as the moiety allowing the target nucleic acid to be separated from other sample components, such as previously described in, e.g., U.S. Pat. No. 6,110,678. Any sequence may be used in a tail region, which is generally about 5 to 50 nt long, and preferred embodiments include a substantially homopolymeric tail of about 10 to 40 nt (e.g., A10 to A40), more preferably about 14 to 33 nt (e.g., A14 to A30 or T3A14 to T3A30), that bind to a complementary immobilized sequence (e.g., poly-T) attached to a solid support, e.g., a matrix or particle. In some such embodiments comprising target-hybridizing sequence(s) configured to specifically hybridize to *Babesia* sp. target nucleic acid, a *Babesia*-specific capture probe comprises or consists of a the nucleotide sequence of SEQ ID NO:43.

Target capture typically occurs in a solution phase mixture that contains one or more capture probe oligomers that hybridize to the target nucleic acid under hybridizing conditions, usually at a temperature higher than the Tm of the [tail sequence] [immobilized probe sequence] duplex. For embodiments comprising a capture probe tail, the [target nucleic acid]:[capture probe] complex is captured by adjusting the hybridization conditions so that the capture probe tail hybridizes to the immobilized probe, and the entire complex on the solid support is then separated from other sample components. The support with the attached [immobilized probe]:[capture probe]:[target nucleic acid] may be washed one or more times to further remove other sample components. Preferred embodiments use a particulate solid support, such as paramagnetic beads, so that particles with the attached [target nucleic acid]:[capture probe]:[immobilized probe] complex may be suspended in a washing solution and retrieved from the washing solution, preferably by using magnetic attraction. In embodiments of the method comprising the use of an amplification-based detection assay, to limit the number of handling steps, a target nucleic acid may be amplified by simply mixing the target nucleic acid in the complex on the support with amplification oligomers and proceeding with amplification steps.

In some embodiments of a method for diagnosing Babesiosis, where detection of *Babesia* sp. indicates Babesiosis in a subject, the method further includes treating Babesiosis in the subject. Treatment regimens for Babesiosis are generally known in the art and include, for example, administration of anti-parasitic medications or red blood cell exchange transfusion as an adjunct therapy. In certain variations, the subject has not been previously diagnosed with Babesiosis. In other embodiments, the subject has been previously diagnosed with Babesiosis and is undergoing treatment for Babesiosis at the time a diagnostic method of the present disclosure is performed. Such variations are particularly useful for monitoring treatment of Babesiosis in a subject. For example, if the method indicates that Babesiosis is still present in the subject, then the subject may continue treatment. In some embodiments, the same treatment regime (i.e., the same treatment that the subject is undergoing at the time the present diagnostic method is performed) is re-administered to the subject. Alternatively, the continued presence of Babesiosis in the subject undergoing treatment may indicate that a change in the ongoing treatment is needed, and a different treatment regime (e.g., a different medication, or an increased dosage and/or frequency of a drug) is administered to the subject.

In accordance with the present disclosure, detecting the presence or absence of *Babesia* sp. may be performed separately (e.g., in a separate reaction vessel), or performed together with another assay as a multiplex reaction system. Accordingly, in some embodiments, a method as described herein (e.g., a method for diagnosing Babesiosis) utilizes a multiplex reaction, where the reaction mix contains reagents for assaying multiple (e.g., at least two, three, four, or more) different target sequences in parallel. In these cases, a reaction mix may contain multiple different target-specific oligonucleotides for performing the detection assay. For example, in a method utilizing an amplification-based detection assay, a multiplex reaction may contain multiple sets (e.g., multiple pairs) of amplification oligomers (for example, multiple pairs of PCR primers or multiple pairs of TMA amplification oligomers (e.g., for TMA, multiple pairs of promoter primer and non-promoter primer, or multiple pairs of promoter provider and non-promoter primer)). In other embodiments utilizing a cleavage-based detection assay, a multiplex reaction may contain multiple probe oligonucleotides having different flaps, multiple different overlapping probe oligonucleotides, and multiple different FRET cassettes for detecting the different flaps, once they are cleaved.

The oligomer combination described herein may be in the form of a reaction mixture or a kit comprising the oligomers. The reaction mixture or kit may further include a number of optional components such as, for example, capture probe nucleic acids or arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a Babesia sp. target nucleic acid may or may not be present. A kit comprising an oligomer combination for amplification of Babesia sp. may also include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). For an oligomer combination (e.g., reaction mixture or kit) that includes a detection probe together with an amplification oligomer combination targeting a common target nucleic acid, selection of amplification oligomers and detection probe oligomers are linked by a common target region (i.e., the combination will include a probe that binds to a sequence amplifiable by the amplification oligomer combination).

The compositions, methods, reaction mixtures, systems, kits and the like for detection of Babesia nucleic acids are further illustrated by the following non-limiting examples.

EXAMPLES

"Sample Transport Solution" generally refers to a solution formulated to preserve a sample, and in some instances formulated to at least partially lyse one or more cell types in a sample. One exemplary sample transport solution comprises 15 mM sodium phosphate monobasic, 15 mM sodium phosphate dibasic, 1 mM EDTA, 1 mM EGTA, and 110 mM lithium lauryl sulfate (LLS), at pH 6.7. Another exemplary sample transport solution comprises an aqueous solution of 100 mM TRIS, 30 mM magnesium chloride, and 6% (v/v) LLS, at pH 7.5. A further exemplary sample transport solution comprises an aqueous solution of 14 mM sodium bicarbonate, 250 mM ammonium chloride, 5% (v/v) LLS, and 0.1 mM EDTA, at a pH of 7.4. Other formulations of sample transport solutions may function equally well.

"Target Capture Reagent" generally refers to a solution containing a number of components that facilitate capture of a nucleic acid from a solution. One exemplary Target Capture Reagent comprises 250 mM HEPES, 310 mM lithium hydroxide, 1.88 M lithium chloride, 100 mM EDTA, at pH 6.4, and 250 µg/ml of magnetic particles (1 micron SERA-MAG^MG-CM particles, GE Healthcare Lifesciences) with $dT_{14}$ oligomers covalently bound thereto. Another exemplary Target Capture Reagent comprises 790 mM HEPES, 453 mM lithium hydroxide, 10% w/v LLS, 230 mM Succinic Acid, 0.03% w/v Foam Ban MS-575, and 0.0125% w/v of magnetic particles (1 micron SERA-MAG^TM MG-CM particles, GE Healthcare Lifesciences) with $dT_{14}$ oligomers covalently bound. Other formulations of Target Capture Reagent may function equally as well.

"Wash Solution" generally refers to a solution containing 10 mM HEPES, 150 mM sodium chloride, 6.5 mM sodium hydroxide, 1 mM EDTA, 0.3% (v/v) ethanol, 0.02% (w/v) methyl paraben, 0.01% (w/v) propyl paraben, and 0.1% (w/v) sodium lauryl sulfate, at pH 7.5.

"Probe Reagent" generally refers to a solution containing one or more labeled detection probes. One exemplary Probe Reagent is a solution made up of from about 75 to about 100 mM lithium succinate, 2% (w/v) LLS, 15 mM mercaptoethanesulfonate, 1.2 M lithium chloride, 20 mM EDTA, and 3% (v/v) ethanol, at pH 4.7. Another exemplary Probe Reagent is a solution made up of from about 75 to about 100 mM succinic acid, 3.5% (w/v) LLS, 75 mM lithium hydroxide, 15 mM aldrithiol-2, 1.0 M lithium chloride, 1 mM EDTA, and 3.0% (v/v) ethanol, at pH 4.1-4.3. Other formulations may perform equally as well.

"Amplification Reagent" generally refers to a concentrated mixture of reaction components to facilitate amplification reactions. An Amplification Reagent will comprise a number of different reagents at various concentrations depending on factors such as for example amplification type (PCR, TMA, etc.), target nucleic acids (GC content), and the like. One exemplary Amplification Reagent comprises 47.6 mM Na-HEPES, 12.5 mM N-acetyl-L-cysteine, 2.5% TRITON™ X-100, 54.8 mM KCl, 23 mM MgCl2, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM Na2EDTA, 5% v/v glycerol, 2.9% trehalose, 0.225% ethanol, 0.075% methylparaben, 0.015% propylparaben, and 0.002% Phenol Red, at pH 7.5-7.6. Another exemplary Amplification Reagent comprises 19.1 mM Trizma Base, 7.5 mM Trizma Hydrochloride, 23.3 mM KCl, 21.5 mM MgCl2, 1 mM of each dNTP (dATP, dCTP, dGTP, dTTP), 6.5 mM rATP, 4.0 mM rCTP, 4.0 mM UTP, 6.5 mM rGTP, 3.33% v/v glycerol, 0.05 mM Zinc Acetate, 6 ppm Pro Clin 300 preservative, at pH 8.25-8.45. Other formulations of amplification reagent may function equally well. Primers may be added to the amplification reagent or added to amplification reactions separate from the amplification reagent. Enzymes in an amplification reagent can include one or more of Moloney Murine Leukemia Virus Reverse Transcriptase (MMLV-RT) and bacteriophage T7 RNA polymerase for which units are functionally defined as: 1 U of MMLV-RT incorporates 1 nmol of dTTP in 10 min at 37 C using 200-400 micromolar oligo dT-primed poly(A) as template, and 1 U of T7 RNA polymerase incorporates 1 nmol of ATP into RNA in 1 hr at 37 C using a DNA template containing a T7 promoter.

"Hybridization Reagent" generally refers to a solution made up of reagents having concentrations in the range of about: 75-100 mM succinic acid, 2%-3.5% (w/v) LLS, 75-100 mM lithium hydroxide, 14-16 mM aldrithiol-2, 1.0-1.2 M lithium chloride, 20-1000 mM EDTA, and 2.0-4.0% (v/v) ethanol, at pH 4-5 Other formulations for a Hybridization Reagent may function equally well.

"Selection Reagent" generally refers to a solution containing 600 mM boric acid, 182.5 mM sodium hydroxide, 1% (v/v) octoxynol (TRITON® X-100), at pH 8.5.

"Detection Reagents" include "Detect Reagent I," which generally refers to a solution containing 1 mM nitric acid and 32 mM hydrogen peroxide, and "Detect Reagent II," which generally refers to a solution of 1.5 M sodium hydroxide.

Example 1: Initial Oligo Screening

Objective:
Non-T7 and T7 primers and probes were screened using the manual Procleix Enhanced Semi-automated System (eSAS) for transcription mediated amplification (TMA) and hybridization protection assays (HPA) in order to identify primer-probe combinations with the ability to amplify and specifically detect specifically species of *Babesia*—including *B. microti*, *B. divergens*, *B. duncani* and *B. venatorum*. The assay does not discriminate between these *Babesia* species. Reactive results indicate that a sample is positive for *Babesia*.

Materials Methods:

Initial primer screening was performed using TMA on the manual Procleix system using in-vitro transcripts (IVT) for *Babesia microti* (SEQ ID NO:61), *Babesia divergens* (SEQ ID NO:62), and *Babesia duncani* (SEQ ID NO:63). Reactions for this testing began at the amplification step. An assay rack consisted of 10 rows of Ten-tube units (TTUs). 75 microliters of Amplification Reagent and 10 picomoles each of one T7 promoter provider oligonucleotide from Tables 1-3 and one non-T7 primer oligonucleotide from Tables 1-3 were added to the appropriate tubes on the rack such that each combination of amplification oligomers were tested with two replicates each of *Plasmodium falciparum* IVT (SEQ ID NO:64) at 10,000 copies per reaction and *B. divergens*, *B. duncani*, and *B. microti* IVT at 15 copies per reaction. *P. falciparum* was included in initial screening as a cross reactivity specimen due to the conserved regions between *Babesia* and *Plasmodium*. It is necessary to determine that amplification and detection systems are specific to *Babesia*. To achieve the target copies per reaction, 10 μL of *P. falciparum* IVT at 1e6 c/mL diluted in a buffer was spiked into the appropriate tubes, and 10 μL of *Babesia* species IVT at 1,500 c/mL diluted in a buffer were spiked into the appropriate tubes. Various combinations of Primers were tested. This set-up allows for 10 primer combinations to be tested per rack. Once the primer combinations and IVTs were spiked, 200 μL of oil was added to each tube and then the rack was covered with sealing cards and vortexed for a minimum of 20 seconds.

The rack was then incubated in a water bath at 60±1° C. for 10±1 minutes followed by incubation in a 41.5±1° C. water bath for between 9 and 20 minutes. While the rack remained in the water bath, the sealing cards were removed and 25 μL of commercially available Procleix Ultrio Plus enzyme reagent (Grifols Diagnostics Solutions, Inc.) was added to each reaction tube and then covered again with sealing cards. The rack was gently shaken to mix and then covered again with sealing cards and incubated for another 60±5 minutes in the 41.5±1° C. water bath.

After incubation completed, the rack was transferred to the hybridization protection assay (HPA) area where the sealing cards were removed. 100 μL of Probe reagent consisting of 1 acridinium-ester (AE) labeled probe (Tables 1-3) added at a total desired concentration of 5e6 Relative Light Units (RLU) per reaction to a Hybridization Reagent. Probe reagent was then added to the appropriate reaction tubes. The tubes were covered with sealing cards and the rack was vortexed for a minimum of 20 seconds after which the rack was incubated in a water bath at 61±2° C. for 15±1 minutes.

The rack was removed from the water bath, the sealing cards removed, and 250 μL of commercially available Procleix Ultrio Plus selection reagent (Grifols Diagnostics Solutions, Inc.) was added to each tube. The tubes were covered with sealing cards and vortexed for a minimum of 20 seconds and then returned to the 61±2° C. water bath and incubated for 10±1 minutes. After incubation the rack was allowed to cool in a 23±4° C. water bath for a minimum of 10 minutes.

For detection the TTUs are removed from the rack and loaded on to the automated Leader instrument for subsequent light off using commercially available Procleix Auto Detect 1 and 2 reagents (Grifols Diagnostics Solutions, Inc.) and the results were exported for analysis of the signal in Relative Light Units (RLU).

Primers screened in Group 1a and Group 1b (Table 1) were each of SEQ ID NO:3 and SEQ ID NO:5 promoter provider oligomers paired with each of SEQ ID NOs:12 to 16, 18 and 19 to 21 using both detection probe SEQ ID NO:37 and 39. Each rack used system SEQ ID NO:1, 11 and 37 as a control.

TABLE 1

Primers screened in Group 1a and Group 1b.

| SEQ ID NO | Sequence 5'-3' |
|---|---|
| 1 | aatttaatacgactcactatagggagattcacctctga cagttaaatacgaa |
| 3 | aatttaatacgactcactatagggagaacagttaaata cgaatgcccccaa |
| 5 | aatttaatacgactcactatagggagattcacctctga cagttaaatac |
| 12 | actacagcatggaataatga |
| 11 | cttgaatactacagcatgga |
| 13 | cttgaatactacagcatggaataa |
| 14 | acttcagcatggaataatga |
| 15 | cttgaatacttcagcatgga |
| 16 | actncagcatggaataatga (n is inosine in this example) |
| 18 | cttgaatactncagcatgga (n is inosine in this example) |
| 20 | actttgagaaaactagagtg |
| 21 | agaaaactagagtgtttcaa |
| 39 | aguaaugguuaauaggagca |
| 37 | ugaaguaggacuuuggucu |

Primers Screened in Group 2 (Table 2) were SEQ ID NO:3 promoter provider paired with each of SEQ ID NOs: 22-31, 75 and 76 primers using SEQ ID NO:39 detection probe. Each rack used system SEQ ID NO:3, SEQ ID NO:21 and SEQ ID NO:39 as a control.

TABLE 2

Primers screened in Group 2.

| SEQ ID NO: | Sequence 5'-3' |
|---|---|
| 3 | aatttaatacgactcactatagggagaa cagttaaatacgaatgcccccaa |
| 21 | agaaaactagagtgtttcaa |
| 24 | ggttctattttgttggtt |
| 25 | tggttctattttgttgg |
| 23 | aggactttggttctattttg |
| 75 | gaagtaggactttggttctattt |

TABLE 2-continued

Primers screened in Group 2.

| SEQ ID NO: | Sequence 5'-3' |
|---|---|
| 76 | atgaagtaggactttggttct |
| 22 | ataatgaagtaggactttgg |
| 26 | ggaataatgaagtaggacttt |
| 27 | atggaataatgaagtaggac |
| 28 | atggaataatgaagtagg |
| 29 | gcatggaataatgaagtag |
| 30 | tacagcatggaataatgaag |
| 31 | tactacagcatggaataatg |
| 39 | aguaaugguuaauaggagca |

Primers screened in Group 3 (Table 3) were SEQ ID NO:1 promoter provider paired with each of SEQ ID NO:21, 27 and 29 primers and SEQ ID NO:38, 40 and 41 detection probes; SEQ ID NO:3 promoter provider paired with each of SEQ ID NO:21, 27 and 29 primers and SEQ ID NO:38 and 40 detection probes; and each of SEQ ID NO:3, 7 and 9 promoter provider paired with SEQ ID NO:21 primer and SEQ ID NO:39 detection probe.

TABLE 3

Primers screened in Group 3.

| SEQ ID NO: | Sequence 5'-3' |
|---|---|
| 3 | aatttaatacgactcactatagggagaacagtaaatacgaatgcccccaa |
| 1 | aatttaatacgactcactatagggagattcactctgacagttaaatacgaa |

TABLE 3-continued

Primers screened in Group 3.

| SEQ ID NO: | Sequence 5'-3' |
|---|---|
| 7 | aatttaatacgactcactatagggagagctttcgcagtagttcgtctttaacaaatc |
| 9 | aatttaatacgactcactatagggagactttcgcagtagttcgtctttaac |
| 21 | agaaaactagagtgtttcaa |
| 27 | atggaataatgaagtaggac |
| 29 | gcatggaataatgaagtag |
| 39 | aguaaugguuaauaggagca |
| 38 | uaaugguuaauaggagcaguug |
| 40 | ggacuuugguucuauuuuguugg |
| 41 | aaugguuaauaggagcaguuggggg |

Results:

Ideal candidates from screening were expected to be reactive for *Babesia* species IVTs (*B. microti, B. divergens* and *B. duncani*) with analyte signals consistently at 1,000,000 RLU or higher for all replicates and negative for *P. falciparum* IVT and negative samples with analyte signals below 10,000 RLU. Some candidates with RLUs near 1,000,000 RLU for *Babesia* and below 30,000 RLU for *P. falciparum* and negatives were also given consideration.

For the primers and detection probes screened in Group 1a, not all primer-probe combinations consistently amplified and detected all species and some combinations resulted in high analyte signals for negative specimens (*P. falciparum* and Negative). Analyte RLU results for this group are listed in Table 4. Preferred candidates in this group were SEQ ID NO:3 promoter provider paired with SEQ ID NO:13, 20 or 21 primers and using SEQ ID NO:37 detection probe; and SEQ ID NO:3 promoter provider paired with SEQ ID NO:21 primer and SEQ ID NO:39 detection probe.

TABLE 4

Analyte RLU Results for Group 1a.

| | | SEQ ID NO: 1 | | SEQ ID NO: 3 | | | |
|---|---|---|---|---|---|---|---|
| | | SEQ ID NO: 11 | | SEQ ID NO: 12 | | SEQ ID NO: 11 | |
| | | A | B | C | D | E | F |
| 10 | SEQ ID NO: 39 | 1,362 | 1,558 | 7,937 | 4,149 | 1,858 | 2,602 |
| 9 | | 1,751 | 1,944 | 217,421 | 2,083,520 | 624,278 | 1,234,110 |
| 8 | | 1,868,814 | 2,073,045 | 1,910,998 | 2,237,157 | 1,158,006 | 2,142,969 |
| 7 | | 2,296,815 | 2,273,471 | 2,348,718 | 2,365,590 | 2,259,692 | 2,374,484 |
| 6 | | 5,122 | 3,273 | 4,390 | 5,389 | 4,890 | 3,165 |
| 5 | SEQ ID NO: 37 | 15,427 | 2,286 | 13,870 | 6,363 | 123,550 | 4,161 |
| 4 | | 8,560 | 739,538 | 1,276,471 | 1,699,429 | 1,883,483 | 1,948,712 |
| 3 | | 1,915,070 | 1,982,035 | 2,030,041 | 2,073,715 | 1,847,501 | 2,010,877 |
| 2 | | 1,556,779 | 2,027,292 | 2,080,918 | 2,033,082 | 1,935,354 | 2,117,207 |
| 1 | | 2,750 | 3,797 | 2,020 | 160,345 | 4,308 | 10,144 |

| | | SEQ ID NO: 3 | | | | |
|---|---|---|---|---|---|---|
| | | SEQ ID NO: 13 | | SEQ ID NO: 14 | | |
| | | G | H | I | J | |
| 10 | SEQ ID NO: 39 | 2,379 | 1,923 | 3,206 | 3,223 | P. fal 10K c/rxn |
| 9 | | 1,512,725 | 1,924,925 | 2,028,160 | 1,717,151 | B. div IVT 15 c/rxn |
| 8 | | 1,262,860 | 2,023,796 | 957,114 | 180,559 | B. dun IVT 15 c/rxn |

TABLE 4-continued

Analyte RLU Results for Group 1a.

| | | | | | | |
|---|---|---|---|---|---|---|
| 7 | | 2,310,437 | 2,287,714 | 2,363,103 | 2,306,377 | B. mic IVT 15 c/rxn |
| 6 | | 3,087 | 4,362 | 3,815 | 2,678 | Neg |
| 5 | SEQ ID | 5,645 | 2,157 | 21,188 | 10,899 | P. fal 10K c/rxn |
| 4 | NO: 37 | 1,753,900 | 1,907,723 | 1,838,478 | 1,913,729 | B. div IVT 15 c/rxn |
| 3 | | 1,929,009 | 1,972,774 | 2,050,677 | 1,981,200 | B. dun IVT 15 c/rxn |
| 2 | | 2,092,557 | 2,077,799 | 1,985,182 | 1,993,369 | B. mic IVT 15 c/rxn |
| 1 | | 1,727 | 2,368 | 2,807 | 5,288 | Neg |

| | | SEQ ID NO: 3 | | | | |
|---|---|---|---|---|---|---|
| | | SEQ ID NO: 15 | | SEQ ID NO: 16 | | SEQ ID NO: 18 |
| | | A | B | C | D | E | F |
| 10 | SEQ ID | 3,873 | 2,436 | 5,785 | 2,743 | 2,406 | 1,968 |
| 9 | NO: 39 | 1,918,232 | 1,880,797 | 1,368,977 | 2,094,325 | 1,486,108 | 2,119,826 |
| 8 | | 1,602,380 | 1,776,094 | 2,135,880 | 2,225,590 | 2,031,084 | 2,095,064 |
| 7 | | 375,283 | 981,890 | 2,375,662 | 2,447,002 | 2,298,733 | 2,218,629 |
| 6 | | 5,902 | 6,937 | 7,033 | 7,979 | 2,758 | 3,564 |
| 5 | SEQ ID | 7,609 | 150,048 | 314,165 | 25,323 | 1,726,513 | 1,674 |
| 4 | NO: 37 | 1,942,612 | 1,891,974 | 1,684,635 | 1,968,192 | 1,669,451 | 1,881,606 |
| 3 | | 1,966,629 | 1,993,188 | 2,063,195 | 2,071,412 | 1,901,864 | 1,960,251 |
| 2 | | 829,468 | 1,477,651 | 2,146,350 | 2,147,242 | 2,049,500 | 2,063,691 |
| 1 | | 1,553 | 4,723 | 190,368 | 12,971 | 1,949 | 1,627 |

| | | SEQ ID NO: 3 | | | |
|---|---|---|---|---|---|
| | | SEQ ID NO: 20 | | SEQ ID NO: 21 | |
| | | G | H | I | J | |
| 10 | SEQ ID | 1,535 | 2,439 | 2,493 | 2,249 | P. fal 10K c/rxn |
| 9 | NO: 39 | 1,912,598 | 882,449 | 1,936,565 | 2,170,010 | B. div IVT 15 c/rxn |
| 8 | | 1,893,023 | 1,800,511 | 2,240,797 | 2,087,446 | B. dun IVT 15 c/rxn |
| 7 | | 2,463,996 | 2,234,843 | 2,323,282 | 2,352,415 | B. mic IVT 15 c/rxn |
| 6 | | 2,246 | 1,866 | 2,602 | 1,792 | Neg |
| 5 | SEQ ID | 1,777 | 1,730 | 1,460 | 5,274 | P. fal 10K c/rxn |
| 4 | NO: 37 | 1,842,523 | 1,892,595 | 1,944,571 | 1,882,381 | B. div IVT 15 c/rxn |
| 3 | | 1,996,707 | 1,995,486 | 2,032,943 | 1,995,159 | B. dun IVT 15 c/rxn |
| 2 | | 2,057,722 | 2,091,173 | 2,110,461 | 2,140,647 | B. mic IVT 15 c/rxn |
| 1 | | 7,879 | 1,642 | 1,779 | 1,602 | Neg |

For the primers and detection probes screened in Group 1b, not all primer-probe combinations consistently amplified and detected all species and some combinations resulted in high analyte signals for *P. falciparum*. Analyte RLU results for this group are listed in Table 5. Preferred candidates in this group were SEQ ID NO:5 promoter provider paired with SEQ ID NO:11 or 13 primers and using the SEQ ID NO:37 detection probe.

TABLE 5

Analyte RLU Results for Group 1b.

| | | SEQ ID NO: 1 | | SEQ ID NO: 5 | | | |
|---|---|---|---|---|---|---|---|
| | | SEQ ID NO: 11 | | SEQ ID NO: 12 | | SEQ ID NO: 11 | |
| | | A | B | C | D | E | F |
| 10 | SEQ ID | 2,370 | 2,021 | 491 | 561 | 1,219 | 1,549 |
| 9 | NO: 39 | 2,606,527 | 2,273,506 | 1,343 | 180,755 | 668,964 | 645,097 |
| 8 | | 2,329,021 | 2,341,992 | 93,675 | 141,525 | 661,755 | 230,617 |
| 7 | | 2,586,212 | 2,656,633 | 2,513,992 | 2,519,282 | 2,398,111 | 2,468,394 |
| 6 | | 2,786 | 2,875 | 946 | 546 | 1,278 | 990 |
| 5 | SEQ ID | 1,086 | 1,296 | 994 | 848 | 1,488 | 805 |
| 4 | NO: 37 | 1,862,765 | 1,798,372 | 392,887 | 965 | 1,378,157 | 1,340,279 |
| 3 | | 1,948,808 | 1,873,185 | 609,730 | 1,553,691 | 1,684,907 | 1,618,765 |
| 2 | | 2,019,896 | 1,956,929 | 1,610,113 | 1,432,157 | 1,866,395 | 1,912,090 |
| 1 | | 1,670 | 878 | 965 | 2,036 | 772 | 1,582 |

TABLE 5-continued

Analyte RLU Results for Group 1b.

| | | SEQ ID NO: 5 | | | | |
|---|---|---|---|---|---|---|
| | | SEQ ID NO: 13 | | SEQ ID NO: 14 | | |
| | | G | H | I | J | |
| 10 | SEQ ID | 4,246 | 3,048 | 1,726 | 2,454 | P. fal 10K c/rxn |
| 9 | NO: 39 | 618,531 | 600,583 | 145,539 | 3,298 | B. div IVT 15 c/rxn |
| 8 | | 439,103 | 421,977 | 7,295 | 48,670 | B. dun IVT 15 c/rxn |
| 7 | | 4,661 | 2,419,801 | 43,673 | 16,001 | B. mic IVT 15 c/rxn |
| 6 | | 3,573 | 3,852 | 1,243 | 3,789 | Neg |
| 5 | SEQ ID | 1,538 | 2,040 | 636,577 | 1,472 | P. fal 10K c/rxn |
| 4 | NO: 37 | 1,313,625 | 1,403,578 | 41,232 | 1,144,411 | B. div IVT 15 c/rxn |
| 3 | | 1,464,595 | 1,660,711 | 379,047 | 252,130 | B. dun IVT 15 c/rxn |
| 2 | | 1,827,977 | 1,878,981 | 543,761 | 1,896,462 | B. mic IVT 15 c/rxn |
| 1 | | 2,724 | 1,371 | 1,544 | 1,320 | Neg |

| | | SEQ ID NO: 1 | | SEQ ID NO: 5 | | | |
|---|---|---|---|---|---|---|---|
| | | SEQ ID NO: 15 | | SEQ ID NO: 16 | | SEQ ID NO: 18 | |
| | | A | B | C | D | E | F |
| 10 | SEQ ID | 6,408 | 5,690 | 1,278 | 1,722 | 1,724 | 2,646 |
| 9 | NO: 39 | 144,774 | 478,638 | 207,863 | 4,342 | 167,329 | 1,078,348 |
| 8 | | 197,399 | 17,034 | 260,958 | 607,257 | 172,231 | 934,843 |
| 7 | | 40,088 | 28,810 | 2,472,660 | 2,440,145 | 2,404,314 | 2,487,783 |
| 6 | | 1,795 | 2,431 | 1,561 | 911 | 1,192 | 3,614 |
| 5 | SEQ ID | 1,197,623 | 1,474 | 939 | 1,303 | 958 | 1,949 |
| 4 | NO: 37 | 1,471,176 | 1,396,263 | 1,493,545 | 137,001 | 1,553,344 | 1,509,390 |
| 3 | | 1,765,530 | 1,753,318 | 1,950,334 | 1,982,086 | 1,758,977 | 1,690,431 |
| 2 | | 805,769 | 424,446 | 2,039,764 | 1,998,885 | 1,941,034 | 1,985,950 |
| 1 | | 1,631 | 1,963 | 1,292 | 1,149 | 1,233 | 38,660 |

| | | SEQ ID NO: 5 | | | | |
|---|---|---|---|---|---|---|
| | | SEQ ID NO: 20 | | SEQ ID NO: 21 | | |
| | | G | H | I | J | |
| 10 | SEQ ID | 1,419 | 1,582 | 703 | 3,712 | P. fal 10K c/rxn |
| 9 | NO: 39 | 401,756 | 346,658 | 98,181 | 219,007 | B. div IVT 15 c/rxn |
| 8 | | 220,859 | 657,682 | 137,758 | 124,133 | B. dun IVT 15 c/rxn |
| 7 | | 2,416,779 | 2,391,258 | 91,104 | 2,492,731 | B. mic IVT 15 c/rxn |
| 6 | | 2,345 | 2,848 | 631 | 659 | Neg |
| 5 | SEQ ID | 1,492 | 193,967 | 984 | 1,949 | P. fal 10K c/rxn |
| 4 | NO: 37 | 520,765 | 929,879 | 756,537 | 1,462,395 | B. div IVT 15 c/rxn |
| 3 | | 1,647,079 | 1,357,270 | 334,747 | 1,183,608 | B. dun IVT 15 c/rxn |
| 2 | | 2,043,012 | 95,200 | 1,937,688 | 1,875,971 | B. mic IVT 15 c/rxn |
| 1 | | 956 | 1,542 | 1,262 | 2,454 | Neg |

For the primers and detection probes screened in Group 2, not all primer-probe combinations consistently amplified and detected all species and some combinations resulted in high analyte signals for *P. falciparum*. Analyte RLU results for this group are listed in Table 6. Preferred candidates in this group were SEQ ID NO:3 promoter provider paired with SEQ ID NO:27, SEQ ID NO:28 or SEQ ID NO:29 primers and SEQ ID NO:39 detection probe.

TABLE 6

Analyte RLU Results for Group 2.

| | Control | | | | | |
|---|---|---|---|---|---|---|
| | SEQ ID NO: 3 | | | | | |
| | SEQ ID NO: 39 | | | | | |
| | A | B | C | D | E | F |
| | SEQ ID NO: 21 | | | SEQ ID NO: 24 | | |
| 10 | 5,538 | 2,060 | 3,451 | 912 | 1,957 | 732 |
| 9 | 2,777,487 | 1,462,676 | 2,411,623 | 42,352 | 261,061 | 36,259 |
| 8 | 2,090,779 | 2,104,742 | 1,619,218 | 344,375 | 87,780 | 46,539 |
| 7 | 2,422,490 | 2,421,930 | 1,995,715 | 392,494 | 1,060,155 | 2,468,927 |
| 6 | 4,111 | 1,487 | 1,423 | 616 | 698 | 994 |
| | SEQ ID NO: 23 | | | SEQ ID NO: 75 | | |
| 5 | 913 | 886 | 1,458 | 979 | 613 | 618 |

TABLE 6-continued

Analyte RLU Results for Group 2.

| | | | | | | |
|---|---|---|---|---|---|---|
| 4 | 722,789 | 19,023 | 52,416 | 13,234 | 1,273,210 | 130,514 |
| 3 | 1,099 | 1,330 | 667 | 5,314 | 2,137 | 1,401 |
| 2 | 2,228,374 | 1,820,781 | 2,162,670 | 1,959,300 | 2,524,372 | 1,916,040 |
| 1 | 1,198 | 608 | 878 | 556 | 532 | 1,244 |

SEQ ID NO: 3
SEQ ID NO: 39

| | G | H | I | J | | |
|---|---|---|---|---|---|---|
| | SEQ ID NO: 25 | | | SEQ ID NO: 31 | | |
| 10 | 839 | 344 | 1,230 | 3,330 | P. fal 10K c/rxn | |
| 9 | 35,686 | 7,687 | 5,156 | 1,589,735 | B. div IVT 15 c/rxn | |
| 8 | 16,068 | 22,627 | 110,271 | 1,642,035 | B. dun IVT 15 c/rxn | |
| 7 | 473,546 | 1,621,876 | 1,933,138 | 2,150,212 | B. mic IVT 15 c/rxn | |
| 6 | 667 | 484 | 508 | 6,630 | Neg | |
| | SEQ ID NO: 76 | | | SEQ ID NO: 31 | | |
| 5 | 931 | 6,188 | 1,313 | 2,697 | P. fal 10K c/rxn | |
| 4 | 901,920 | 816,015 | 1,059,461 | 2,138,285 | B. div IVT 15 c/rxn | |
| 3 | 350,464 | 95,471 | 40,369 | 2,468,230 | B. dun IVT 15 c/rxn | |
| 2 | 1,887,684 | 1,511,500 | 2,263,008 | 389,108 | B. mic IVT 15 c/rxn | |
| 1 | 525 | 1,912 | 903 | 11,272 | Neg | |

SEQ ID NO: 3
SEQ ID NO: 39

| | A | B | C | D | E | F |
|---|---|---|---|---|---|---|
| | SEQ ID NO: 22 | | | SEQ ID NO: 26 | | |
| 10 | 924 | 972 | 8,531 | 5,715 | 1,627 | 1,017 |
| 9 | 87,406 | 60,599 | 71,115 | 778,850 | 371,058 | 574,028 |
| 8 | 3,156 | 3,152 | 5,092 | 150,582 | 154,380 | 75,725 |
| 7 | 2,201,409 | 2,091,981 | 2,098,983 | 2,181,859 | 2,111,286 | 2,220,157 |
| 6 | 1,263 | 1,258 | 1,013 | 3,675 | 1,411 | 1,513 |
| | SEQ ID NO: 28 | | | SEQ ID NO: 29 | | |
| 5 | 9,482 | 1,7459 | 1,830 | 3,932 | 4,278 | 3,258 |
| 4 | 1,169,497 | 1,283,384 | 1,523,739 | 2,167,497 | 2,112,640 | 2,151,586 |
| 3 | 1,118,901 | 584,074 | 1,104,469 | 1,847,271 | 1,481,735 | 2,000,601 |
| 2 | 2,291,400 | 2,263,798 | 2,225,197 | 2,338,122 | 2,318,877 | 2,287,637 |
| 1 | 5,439 | 3,796 | 1,551 | 3,578 | 8,224 | 4,044 |

SEQ ID NO: 3
SEQ ID NO: 39

| | G | H | I | J | | |
|---|---|---|---|---|---|---|
| | SEQ ID NO: 27 | | | SEQ ID NO: 31 | | |
| 10 | 3,853 | 3,043 | 3,064 | 5,868 | P. fal 10K c/rxn | |
| 9 | 2,101,084 | 1,994,330 | 1,804,057 | 2,086,334 | B. div IVT 15 c/rxn | |
| 8 | 1,697,144 | 1,487,220 | 1,493,662 | 1,951,476 | B. dun IVT 15 c/rxn | |
| 7 | 2,376,261 | 2,312,253 | 2,351,514 | 2,288,840 | B. mic IVT 15 c/rxn | |
| 6 | 2,573 | 7,310 | 5,289 | 6,093 | Neg | |
| | SEQ ID NO: 30 | | | SEQ ID NO: 31 | | |
| 5 | 7,941 | 10,249 | 397,486 | 2,514 | P. fal 10K c/rxn | |
| 4 | 2,205,990 | 88,246 | 2,231,170 | 2,099,814 | B. div IVT 15 c/rxn | |
| 3 | 2,143,050 | 2,113,739 | 2,037,798 | 1,730,715 | B. dun IVT 15 c/rxn | |
| 2 | 2,307,754 | 2,272,338 | 2,206,558 | 2,230,915 | B. mic IVT 15 c/rxn | |
| 1 | 14,896 | 2,781 | 1,362 | 1,916 | Neg | |

Analyte RLU results for the primers and detection probes screened in Group 3 are listed in Table 7. Primers paired with detection probes SEQ ID NO:40 and SEQ ID NO:41 yielded high analyte signals for *P. falciparum*, negative samples and *Babesia* positive samples indicating poor design of the probe. Thus, SEQ ID NO:40 and SEQ ID NO:41 and were not included in additional examples. Combinations of SEQ ID NO:3 promoter provider with detection probe SEQ ID NO:38 (regardless of the primer used in this example) yielded high analyte signal in negative samples indicating a probable primer-probe interaction, and thus these oligomers were not included in additional examples. Candidates considered for use with additional detection probes were SEQ ID NO:1 promoter provider with SEQ ID NO:27 or 29 primers and SEQ ID NO:38 detection probe. For new T7 promoter provider screened in this group, SEQ ID NO:3 and 7 paired with SEQ ID NO:21 primer and SEQ ID NO:39 detection probe were considered. SEQ ID NO:9 promoter provider, SEQ ID NO:21 primer and SEQ ID NO:39 detection probe showed no amplification and detection of *Babesia* targets.

TABLE 7

Analyte RLU Results For Group 3

| | SEQ ID NO: 38 SEQ ID NO: 1 | | | SEQ ID NO: 41 SEQ ID NO: 1 | | | Blank | | | | |
|---|---|---|---|---|---|---|---|---|---|---|---|
| | SEQ ID NO: 21 | SEQ ID NO: 27 | SEQ ID NO: 29 | SEQ ID NO: 21 | SEQ ID NO: 27 | SEQ ID NO: 29 | | | | | |
| | A | B | C | D | E | F | G | H | I | J | |
| 10 | 1,183 | 4,868 | 2,229 | 1,999,003 | 1,973,790 | 1,943,078 | 8 | 8 | 9 | 8 | P.fal 10K c/rxn |
| 9 | 273,967 | 2,140,180 | 896,930 | 3,319,370 | 2,458,639 | 1,891,471 | 9 | 9 | 8 | 8 | B.div IVT 15 c/rxn |
| 8 | 2,569,264 | 2,530,890 | 2,494,566 | 3,175,342 | 2,598,410 | 2,129,032 | 8 | 7 | 5 | 8 | B.dun IVT 15 c/rxn |
| 7 | 2,481,447 | 2,349,620 | 2,600,164 | 3,769,511 | 2,880,852 | 2,707,608 | 9 | 7 | 8 | 24 | B.mic IVT 15 c/rxn |
| 6 | 1,792 | 2,291 | 4,106 | 1,373,994 | 2,056,230 | 2,277,790 | 9 | 5 | 9 | 8 | Neg |
| 5 | 2,503 | 12,777 | 8,428 | 2,386,352 | 1,947,735 | 2,160,802 | 10 | 7 | 7 | 10 | P.fal 10K c/rxn |
| 4 | 2,177,455 | 2,061,853 | 1,646,064 | 3,297,211 | 2,150,824 | 2,802,834 | 9 | 7 | 7 | 7 | B.div IVT 15 c/rxn |
| 3 | 2,508,586 | 2,634,974 | 2,567,929 | 3,430,103 | 2,765,117 | 3,556,389 | 8 | 6 | 9 | 8 | B.dun IVT 15 c/rxn |
| 2 | 2,601,774 | 2,583,708 | 2,551,550 | 3,333,080 | 3,719,802 | 3,344,092 | 8 | 8 | 9 | 9 | B.mic IVT 15 c/rxn |
| 1 | 835 | 2,079 | 2,581 | 1,960,393 | 2,096,053 | 2,145,235 | 7 | 5 | 9 | 10 | Neg |

| | | SEQ ID NO: 3 | | | | | | | | | |
|---|---|---|---|---|---|---|---|---|---|---|---|
| | | SEQ ID NO: 15 | | SEQ ID NO: 16 | | SEQ ID NO: 18 | | SEQ ID NO: 20 | | SEQ ID NO: 21 | |
| | | A | B | C | D | E | F | G | H | I | J | |
| 10 | SEQ ID NO: 39 | 3,873 | 2,436 | 5,785 | 2,743 | 2,406 | 1,968 | 1,535 | 2,439 | 2,493 | 2,249 | P.fal 10K c/rxn |
| 9 | | 1,918,232 | 1,880,797 | 1,368,977 | 2,094,325 | 1,486,108 | 2,119,826 | 1,912,598 | 882,449 | 1,936,565 | 2,170,010 | B.div IVT 15 c/rxn |
| 8 | | 1,602,380 | 1,776,094 | 2,135,880 | 2,225,590 | 2,031,084 | 2,095,064 | 1,893,023 | 1,800,511 | 2,240,797 | 2,087,446 | B.dun IVT 15 c/rxn |
| 7 | | 375,283 | 981,890 | 2,375,662 | 2,447,002 | 2,298,733 | 2,218,629 | 2,463,996 | 2,234,843 | 2,323,282 | 2,352,415 | B.mic IVT 15 c/rxn |
| 6 | | 5,902 | 6,937 | 7,033 | 7,979 | 2,758 | 3,564 | 2,246 | 1,866 | 2,602 | 1,792 | Neg |
| 5 | SEQ ID NO: 37 | 7,609 | 150,048 | 314,165 | 25,323 | 1,726,513 | 1,674 | 1,777 | 1,730 | 1,460 | 5,274 | P.fal 10K c/rxn |
| 4 | | 1,942,612 | 1,891,974 | 1,684,635 | 1,968,192 | 1,669,451 | 1,881,606 | 1,842,528 | 1,892,595 | 1,944,571 | 1,882,381 | B.div IVT 15 c/rxn |
| 3 | | 1,966,629 | 1,993,188 | 2,063,195 | 2,071,412 | 1,901,864 | 1,960,251 | 1,996,707 | 1,995,486 | 2,032,943 | 1,995,159 | B.dun IVT 15 c/rxn |
| 2 | | 829,468 | 1,477,651 | 2,146,350 | 2,147,242 | 2,049,500 | 2,063,691 | 2,057,722 | 2,091,173 | 2,110,461 | 2,140,647 | B.mic IVT 15 c/rxn |
| 1 | | 1,553 | 4,723 | 190,368 | 12,971 | 1,949 | 1,627 | 7,879 | 1,642 | 1,779 | 1,602 | Neg |

CONCLUSIONS

The results of this initial screening demonstrated that not all primers and probes reliably amplify and detect all *Babesia* species. Some candidates were not specific to *Babesia*, showing some amplification of *P. falciparum*, while other candidates demonstrated false positives, false negatives and/or primer-probe interactions. Initial screening of amplification and detection systems identified several candidates that show sensitive and specific detection of *B. microti, B. divergens* and *B. duncani*. These candidates do not cross react with *P. falciparum* further demonstrating specificity of the systems. The sensitive and specific combinations from this example were considered for further sensitivity and specificity evaluation.

Example 2: Secondary Oligo Screening for the *Babesia* Assay

Objective

Candidate amplification combinations identified in Example 1 for the *Babesia* Assay using the manual Procleix Enhanced Semi-automated System (eSAS) were screened on the fully automated Procleix Panther System to determine the best candidates in terms of specificity and sensitivity using *Babesia* Species in-vitro transcripts (IVT).

Materials and Methods

Candidate amplification systems were tested on the automated Procleix Panther system (Grifols Diagnostics Solutions, Inc.). Combinations of amplification and detection oligomers tested are listed in Table 8. Sequences for each oligo are listed in Table 9. A total of 8 conditions were screened. Conditions screened were tested against 45 replicates of a negative panel and 6 replicates each of diluted *Babesia* in-vitro transcripts (IVT) for *B. microti, B. divergens* and *B. duncani* (SEQ ID NOs:61, 62, & 63, respectively) at 30 c/ml. An assay calibrator comprising a *B. microti* IVT panel at 500 c/mL was included to determine the analyte cutoff for the run. The assay software uses the analyte cutoff to determine if samples are reactive or non-reactive. Samples with a signal to cutoff ratio of >1 are considered reactive, while those <1 are non-reactive. Assay Reagents used included the following: a Target Capture Reagent (TCR) comprising of a single Target Capture Oligo (TCO) added at a concentration of 5 pmoles per reaction; an Amplification Reagent comprising one T7 promoter provider and one non-T7 primer each added at a concentration of 10 pmoles per reaction; a Probe reagent consisting of 1 acridinium-ester (AE) labeled probe added at a total concentration of 5e6 Relative Light Units (RLU) per reaction to a solution of; Enzyme Reagent; and Selection Reagent.

A second round of oligo screening was performed to follow up on candidate systems identified in Example 1. Conditions tested in this group are listed in Table 10. Sequences for each oligo are listed in Table 11. A total of 6 additional conditions were screened. Conditions screened were tested against 8 replicates of a negative sample and 7 replicates of diluted *Babesia* in-vitro transcripts (IVT) for each of *B. microti, B. divergens* and *B. duncani* at 100, 30, and 10 c/ml. A cross reactivity panel consisting of 8 replicates *P. falciparum* IVT at 1e6 c/mL was also tested to determine if the system is specific to *Babesia* in the presence of *Plasmodium*. An assay calibrator made from a *B. microti* IVT panel at 500 c/mL.

TABLE 8

Conditions 1-8 Tested on the Panther System

| Condition # | Target Capture Oligo | T7 Primer | Non-T7 Primer | Probe |
|---|---|---|---|---|
| 1 | SEQ ID NO: 43 | SEQ ID NO: 1 | SEQ ID NO: 11 | SEQ ID NO: 37 |
| 2 | SEQ ID NO: 43 | SEQ ID NO: 1 | SEQ ID NO: 27 | SEQ ID NO: 39 |
| 3 | SEQ ID NO: 43 | SEQ ID NO: 1 | SEQ ID NO: 27 | SEQ ID NO: 38 |
| 4 | SEQ ID NO: 43 | SEQ ID NO: 1 | SEQ ID NO: 13 | SEQ ID NO: 37 |
| 5 | SEQ ID NO: 43 | SEQ ID NO: 3 | SEQ ID NO: 21 | SEQ ID NO: 37 |
| 6 | SEQ ID NO: 43 | SEQ ID NO: 7 | SEQ ID NO: 21 | SEQ ID NO: 37 |
| 7 | SEQ ID NO: 43 | SEQ ID NO: 7 | SEQ ID NO: 27 | SEQ ID NO: 39 |
| 8 | SEQ ID NO: 43 | SEQ ID NO: 5 | SEQ ID NO: 21 | SEQ ID NO: 37 |

TABLE 9

Sequences for Oligos listed in Table 8.

| Reagent | Short Name | Sequence 5'-3' |
|---|---|---|
| TCR | SEQ ID NO: 43 | uaggccaauacccuaccgucc tttaaaaaaaaaaaaaaaaaa aaaaaaaaaaaa |
| Amplification | SEQ ID NO: 1 | aatttaatacgactcactata gggagattcacctctgacagt taaatacgaa |
| | SEQ ID NO: 3 | aatttaatacgactcactata gggagaacagttaaatacgaa tgcccccaa |
| | SEQ ID NO: 5 | aatttaatacgactcactata gggagattcacctctgacagt taaatac |
| | SEQ ID NO: 7 | aatttaatacgactcactata gggagagctttcgcagtagtt cgtctttaacaaatc |
| | SEQ ID NO: 13 | cttgaatactacagcatggaa taa |
| | SEQ ID NO: 21 | agaaaactagagtgtttcaa |
| | SEQ ID NO: 27 | atggaataatgaagtaggac |
| Probe | SEQ ID NO: 37 | ugaaguaggacuuugguucu |
| | SEQ ID NO: 38 | uaaugguuaauaggagcagu ug |
| | SEQ ID NO: 39 | aguaaugguuaauaggagca |

TABLE 10

Conditions 9-14 tested on the Panther System

| Condition | Target Capture Oligo | T7 Primer | Non T7 Primer | Probe |
|---|---|---|---|---|
| 9 | SEQ ID NO: 43 | SEQ ID NO: 7 | SEQ ID NO: 21 | SEQ ID NOs: 37 + 42 |
| 10 | SEQ ID NO: 43 | SEQ ID NO: 7 | SEQ ID NO: 32 | SEQ ID NOs: 37 + 42 |
| 11 | SEQ ID NO: 43 | SEQ ID NO: 7 | SEQ ID NO: 33 | SEQ ID NOs: 37 + 42 |
| 12 | SEQ ID NO: 43 | SEQ ID NO: 7 | SEQ ID NO: 34 | SEQ ID NOs: 37 + 42 |
| 13 | SEQ ID NO: 43 | SEQ ID NO: 7 | SEQ ID NO: 35 | SEQ ID NOs: 37 + 42 |
| 14 | SEQ ID NO: 43 | SEQ ID NO: 7 | SEQ ID NO: 36 | SEQ ID NOs: 37 + 42 |

TABLE 11

Sequences for Oligos listed in Table 10.

| Reagent | Short Name | Sequence 5'-3' |
|---|---|---|
| TCR | SEQ ID NO: 43 | uaggccaauacccuaccgucc tttaaaaaaaaaaaaaaaaa aaaaaaaaaaa |
| Amplification | SEQ ID NO: 7 | aatttaatacgactcactata gggagagcttttcgcagtagtt cgtctttaacaaatc |
|  | SEQ ID NO: 21 | agaaaactagagtgtttcaa |
|  | SEQ ID NO: 32 | agaaaactagagtgtttca |
|  | SEQ ID NO: 33 | agaaaattagagtgtttcaa |
|  | SEQ ID NO: 34 | gagaaaactagagtgtttcaa |
|  | SEQ ID NO: 35 | gagaaaattagagtgtttcaa |
|  | SEQ ID NO: 36 | tgagaaaactagagtgtttc |
| Probe | SEQ ID NO: 37 | ugaaguaggacuuugguucu |
|  | SEQ ID NO: 42 | aguaggacuuugguucu |

Results:

An analyte signal cutoff of 100,000 RLU was used to determine reactivity for specimens screened for Conditions 1-8 in Table 12. Samples above this cutoff were considered reactive. Conditions 1 and 4 yielded a false positive rate in negative specimens of 22% and 13% respectively indicating a primer interaction with the probe. Condition 7 was unable to detect *B. divergens* and *B. duncani* IVT at 30 c/mL at 100% reactivity. Due to the high rate of false positives seen in this example using the SEQ ID NO:1 promoter provider, additional screening was performed on alternative candidates.

TABLE 12

Results for Conditions 1-8

| Condition # | Sample Description | Valid | Reactive | % Reactive | Average Analyte RLU | StdDev Analyte RLU |
|---|---|---|---|---|---|---|
| 1 | *B. microti* Calibrator | 3 | 3 | 100 | 2,895,211 | 95,178 |
|  | Negative Buffer | 45 | 10 | 22 | 83,538 | 169,164 |
|  | *B. microti* 30 c/mL | 6 | 6 | 100 | 2,785,208 | 192,438 |
|  | *B. duncani* 30 c/mL | 6 | 6 | 100 | 2,704,843 | 52,325 |
|  | *B. divergens* 30 c/mL | 5 | 5 | 100 | 2,679,799 | 131,010 |
| 2 | *B. microti* Calibrator | 3 | 3 | 100 | 2,164,104 | 85,510 |
|  | Negative Buffer | 45 | 0 | 0 | 1,419 | 881 |
|  | *B. microti* 30 c/mL | 5 | 5 | 100 | 2,184,976 | 107,021 |
|  | *B. duncani* 30 c/mL | 5 | 5 | 100 | 1,842,832 | 79,094 |
|  | *B. divergens* 30 c/mL | 5 | 5 | 100 | 1,710,700 | 484,713 |
| 3 | *B. microti* Calibrator | 3 | 3 | 100 | 5,202,778 | 356,597 |
|  | Negative Buffer | 45 | 0 | 0% | 5,048 | 2,938 |
|  | *B. microti* 30 c/mL | 6 | 6 | 100 | 5,282,576 | 336,909 |
|  | *B. duncani* 30 c/mL | 6 | 6 | 100 | 4,987,308 | 396,702 |
|  | *B. divergens* 30 c/mL | 6 | 6 | 100 | 4,898,995 | 261,124 |
| 4 | *B. microti* Calibrator | 3 | 3 | 100 | 2,847,426 | 127,963 |
|  | Negative Buffer | 45 | 6 | 13 | 62,163 | 212,258 |
|  | *B. microti* 30 c/mL | 6 | 6 | 100 | 2,920,118 | 186,525 |
|  | *B. duncani* 30 c/mL | 6 | 6 | 100 | 2,637,399 | 213,549 |
|  | *B. divergens* 30 c/mL | 6 | 6 | 100 | 2,555,922 | 322,889 |
| 5 | *B. microti* Calibrator | 3 | 3 | 100 | 2,614,010 | 43,029 |
|  | Negative Buffer | 45 | 0 | 0 | 1,064 | 604 |
|  | *B. microti* 30 c/mL | 6 | 6 | 100 | 2,562,482 | 60,848 |
|  | *B. duncani* 30 c/mL | 6 | 6 | 100 | 2,317,458 | 47,231 |
|  | *B. divergens* 30 c/mL | 6 | 6 | 100 | 2,329,932 | 33,382 |
| 6 | *B. microti* Calibrator | 3 | 3 | 100 | 2,849,900 | 59,411 |
|  | Negative Buffer | 45 | 0 | 0 | 1,007 | 548 |
|  | *B. microti* 30 c/mL | 6 | 6 | 100 | 2,779,409 | 77,390 |
|  | *B. duncani* 30 c/mL | 6 | 6 | 100 | 2,472,381 | 110,379 |
|  | *B. divergens* 30 c/mL | 6 | 6 | 100 | 2,608,790 | 176,482 |
| 7 | *B. microti* Calibrator | 3 | 3 | 100 | 5,706,224 | 96,503 |
|  | Negative Buffer | 45 | 0 | 0 | 3,062 | 1,006 |

TABLE 12-continued

Results for Conditions 1-8

| Condition # | Sample Description | Valid | Reactive | % Reactive | Average Analyte RLU | StdDev Analyte RLU |
|---|---|---|---|---|---|---|
| | B. microti 30 c/mL | 6 | 6 | 100 | 5,513,204 | 219,801 |
| | B. duncani 30 c/mL | 6 | 2 | 33 | 124,483 | 155,936 |
| | B. divergens 30 c/mL | 6 | 3 | 50 | 301,854 | 494,564 |
| 8 | B. microti Calibrator | 3 | 3 | 100 | 2,963,935 | 70,693 |
| | Negative Buffer | 45 | 0 | 0 | 932 | 645 |
| | B. microti 30 c/mL | 6 | 6 | 100 | 2,977,421 | 189,225 |
| | B. duncani 30 c/mL | 6 | 6 | 100 | 2,678,642 | 179,586 |
| | B. divergens 30 c/mL | 6 | 6 | 100 | 2,517,233 | 223,392 |

In the previous round of screening, several candidates showed good sensitivity and specificity for *Babesia* species IVT. Condition 6 had good sensitivity and specificity with strong analyte signal for the *Babesia* IVT specimens tested and low analyte signal for negative specimens. Additional screening was performed on the Panther system using the SEQ ID NO:7 promoter provider paired with a number of non-T7 primers to determine the performance of these oligomer combinations. Condition 12 had the best performance of the conditions screened in this round. Condition 12 had best performance in terms of percent reactivity for all levels tested for all *Babesia* species IVTs and strongest RLU signal for all levels. Condition 12 also had the lowest analyte signal for negative specimens.

TABLE 13

Results for Conditions 9-14.

| Condition # | Sample Description | Level | Valid | Reactive | % Reactive | Average Analyte RLU | StdDev Analyte RLU |
|---|---|---|---|---|---|---|---|
| 9 | Negative Calibrator | 0 | 3 | 0 | 0 | 3,064 | 2,870 |
| | B. microti Calibrator | 500 c/mL | 3 | 3 | 100 | 2,634,036 | 20,467 |
| | B. microti IVT | 100 c/mL | 7 | 7 | 100 | 1,782,835 | 124,480 |
| | | 30 c/mL | 7 | 6 | 86 | 1,478,196 | 136,864 |
| | | 10 c/mL | 7 | 5 | 71 | 1,504,124 | 110,673 |
| | B. duncani IVT | 100 c/mL | 7 | 7 | 100 | 1,615,981 | 207,184 |
| | | 30 c/mL | 7 | 7 | 100 | 1,046,502 | 282,167 |
| | | 10 c/mL | 7 | 6 | 86 | 817,242 | 310,430 |
| | B. divergens IVT | 100 c/mL | 7 | 7 | 100 | 1,107,329 | 280,864 |
| | | 30 c/mL | 7 | 7 | 100 | 780,602 | 285,167 |
| | | 10 c/mL | 7 | 3 | 43 | 312,826 | 199,281 |
| | Negative IC Buffer | 0 | 8 | 0 | 0 | 921 | 1,069 |
| | P. falciparum IVT | 1.00e6 c/mL | 8 | 0 | 0 | 1,546 | 1,944 |
| 10 | Negative Calibrator | 0 | 3 | 0 | 0 | 2,083 | 1,176 |
| | B. microti Calibrator | 500 c/mL | 3 | 3 | 100 | 2,612,367 | 134,872 |
| | B. microti IVT | 100 c/mL | 7 | 7 | 100 | 1,841,300 | 261,033 |
| | | 30 c/mL | 7 | 6 | 86 | 1,329,659 | 395,229 |
| | | 10 c/mL | 7 | 4 | 57 | 708,829 | 275,561 |
| | B. duncani IVT | 100 c/mL | 7 | 7 | 100 | 1,475,991 | 196,296 |
| | | 30 c/mL | 7 | 7 | 100 | 717,189 | 386,202 |
| | | 10 c/mL | 7 | 4 | 57 | 471,736 | 348,996 |
| | B. divergens IVT | 100 c/mL | 7 | 7 | 100 | 910,674 | 330,110 |
| | | 30 c/mL | 7 | 6 | 86 | 565,166 | 200,817 |
| | | 10 c/mL | 7 | 3 | 43 | 158,352 | 37,831 |
| | Negative IC Buffer | 0 | 8 | 0 | 0 | 2,802 | 2,381 |
| | P. falciparum IVT | 1.00e6 c/mL | 8 | 0 | 0 | 3,459 | 3,274 |
| 11 | Negative Calibrator | 0 | 3 | 0 | 0 | 1,687 | 1,471 |
| | B. microti Calibrator | 500 c/mL | 3 | 3 | 100 | 2,476,171 | 150,100 |
| | B. microti IVT | 100 c/mL | 7 | 7 | 100 | 1,887,931 | 90,174 |
| | | 30 c/mL | 7 | 7 | 100 | 1,042,715 | 590,288 |
| | | 10 c/mL | 7 | 2 | 29 | 961,097 | 598,572 |
| | B. duncani IVT | 100 c/mL | 7 | 7 | 100 | 1,402,621 | 146,419 |
| | | 30 c/mL | 7 | 7 | 100 | 580,415 | 252,668 |
| | | 10 c/mL | 7 | 4 | 57 | 252,969 | 139,120 |
| | B. divergens IVT | 100 c/mL | 7 | 7 | 100 | 903,456 | 261,139 |
| | | 30 c/mL | 7 | 7 | 100 | 484,118 | 271,417 |
| | | 10 c/mL | 7 | 6 | 86 | 283,109 | 129,194 |
| | Negative IC Buffer | 0 | 8 | 0 | 0 | 2,334 | 1,997 |
| | P. falciparum IVT | 1.00e6 c/mL | 8 | 0 | 0 | 2,035 | 1,681 |

TABLE 13-continued

Results for Conditions 9-14.

| Condition # | Sample Description | Level | Valid | Reactive | % Reactive | Average Analyte RLU | StdDev Analyte RLU |
|---|---|---|---|---|---|---|---|
| 12 | Negative Calibrator | 0 | 3 | 0 | 0 | 370 | 640 |
|  | B. microti Calibrator | 500 c/mL | 3 | 3 | 100 | 2,742,289 | 194,078 |
|  | B. microti IVT | 100 c/mL | 7 | 7 | 100 | 2,092,032 | 386,586 |
|  |  | 30 c/mL | 7 | 7 | 100 | 1,568,851 | 376,918 |
|  |  | 10 c/mL | 7 | 5 | 71 | 1,334,103 | 542,119 |
|  | B. duncani IVT | 100 c/mL | 7 | 7 | 100 | 1,867,880 | 208,460 |
|  |  | 30 c/mL | 7 | 7 | 100 | 1,264,832 | 533,439 |
|  |  | 10 c/mL | 7 | 7 | 100 | 881,072 | 287,187 |
|  | B. divergens IVT | 100 c/mL | 7 | 7 | 100 | 1,456,923 | 228,759 |
|  |  | 30 c/mL | 7 | 7 | 100 | 1,013,056 | 162,035 |
|  |  | 10 c/mL | 7 | 6 | 86 | 941,635 | 247,989 |
|  | Negative IC Buffer | 0 | 8 | 0 | 0 | 391 | 944 |
|  | P. falciparum IVT | 1.00e6 c/mL | 8 | 0 | 0 | 479 | 744 |
| 13 | Negative Calibrator | 0 | 3 | 0 | 0 | 18 | 31 |
|  | B. microti Calibrator | 500 c/mL | 3 | 3 | 100 | 2,618,344 | 183,612 |
|  | B. microti IVT | 100 c/mL | 7 | 7 | 100 | 1,689,812 | 234,944 |
|  |  | 30 c/mL | 7 | 7 | 100 | 1,295,755 | 316,505 |
|  |  | 10 c/mL | 7 | 5 | 71 | 494,319 | 480,634 |
|  | B. duncani IVT | 100 c/mL | 7 | 5 | 71 | 644,015 | 376,799 |
|  |  | 30 c/mL | 7 | 7 | 100 | 1,026,959 | 141,543 |
|  |  | 10 c/mL | 7 | 7 | 100 | 1,808,125 | 209,910 |
|  | B. divergens IVT | 100 c/mL | 7 | 7 | 100 | 1,129,487 | 153,036 |
|  |  | 30 c/mL | 7 | 7 | 100 | 670,066 | 221,406 |
|  |  | 10 c/mL | 7 | 6 | 86 | 270,616 | 143,462 |
|  | Negative IC Buffer | 0 | 8 | 0 | 0 | 400 | 644 |
|  | P. falciparum IVT | 1.00e6 c/mL | 8 | 0 | 0 | 1,237 | 1,803 |
| 14 | Negative Calibrator | 0 | 3 | 0 | 0 | 673 | 843 |
|  | B. microti Calibrator | 500 c/mL | 3 | 3 | 100 | 2,656,960 | 89,493 |
|  | B. microti IVT | 100 c/mL | 7 | 7 | 100 | 2,364,847 | 143,184 |
|  |  | 30 c/mL | 7 | 6 | 86 | 2,051,745 | 116,278 |
|  |  | 10 c/mL | 7 | 5 | 71 | 1,450,039 | 626,015 |
|  | B. duncani IVT | 100 c/mL | 7 | 4 | 57 | 1,136,704 | 353,951 |
|  |  | 30 c/mL | 7 | 7 | 100 | 1,839,238 | 336,415 |
|  |  | 10 c/mL | 7 | 7 | 100 | 2,315,286 | 141,813 |
|  | B. divergens IVT | 100 c/mL | 7 | 7 | 100 | 1,650,341 | 270,259 |
|  |  | 30 c/mL | 7 | 7 | 100 | 1,068,065 | 468,460 |
|  |  | 10 c/mL | 7 | 3 | 43 | 1,459,374 | 758,660 |
|  | Negative IC Buffer | 0 | 8 | 0 | 0 | 574 | 689 |
|  | P. falciparum IVT | 1.00e6 c/mL | 8 | 0 | 0 | 941 | 1,394 |

CONCLUSIONS

Several candidate systems identified on the manual eSAS system yielded good specificity and sensitivity with *Babesia* species IVTs for the *Babesia* Assay during secondary screening on the fully automated Panther system. Others combinations showed poor sensitivity (Condition 7) or specificity (Condition 1 and 4) and were not advanced to additional screening. A second round of screening on the Panther system identified a new system (Condition 12) with sensitivity in lower dilutions of *Babesia* species IVTs superior to other conditions tested and good specificity for the *Babesia* assay.

Example 3: Clinical Sample Screening

Objective

Candidate amplification systems previously identified for the *Babesia* Assay on the manual Procleix Enhanced Semi-automated System (eSAS) were screened on the fully automated Procleix Panther System to determine the best candidates in terms of specificity and sensitivity using a *Babesia* clinical sample. Primers screened in this example are the same as Example 2. This experiment served as an additional test to determine the best performing candidates.

Materials and Methods

Candidate amplification systems were tested on the automated Procleix Panther system. Combinations tested are listed in Table 14. Sequences for each oligo are listed in Table 15. A total of 8 conditions were screened. Conditions screened were tested using 9 replicates each of a lysed negative whole blood and diluted *Babesia*-infected clinical sample. The *Babesia* clinical sample consisted of a PCR Positive *Babesia*-infected human red blood cell (RBC) sample. The sample was received with an estimated parasite per mL value. Based upon the estimated parasite per mL value, the clinical sample was diluted in normal negative human whole blood to an estimated 30, 10, and 3 parasites per mL. The diluted *Babesia*-infected whole blood was lysed at a 1 to 6 ratio or 0.8 mL of whole blood in 4.8 mL of lysis solution Aptima Urine Transport Medium (commercially available). The negative panel was lysed according to the same procedure. Assay Reagents used included the following: a Target Capture Reagent (TCR) comprising of a single Target Capture Oligo (TCO) added at a concentration of 5 pmoles per reaction; an Amplification Reagent comprising one T7 promoter provider and one non-T7 primer each added at a concentration of 10 pmoles per reaction; a Probe reagent consisting of 1 acridinium-ester (AE) labeled probe added at a total concentration of 5e6 Relative Light Units (RLU) per reaction to a solution of; Enzyme Reagent; and Selection Reagent.

Conditions tested in this group are listed in Table 16. Sequences for each oligo are listed in Table 17. A total of 6 additional conditions were screened. Conditions were tested using 5 replicates of each of a *Babesia*-negative whole blood sample and a diluted *Babesia*-infected whole blood clinical sample. Prior to testing the negative and positive samples, the parasite concentration of the *Babesia*-infected clinical sample was estimated by using a calibration curve. The calibration curve was generated using lysates from serial dilutions of a known standard (a quantified *Babesia*-positive whole blood specimen). The clinical samples and the serial dilutions of the known standard were tested using a real-time assay. The Ttimes from each of the dilutions of the known standard were plotted against the parasites/mL to generate an equation. The equation was then used to convert Ttime to parasites/mL when the clinical sample was run using the same assay. The clinical sample was then diluted in normal negative human whole blood to an estimated 30 and 10 parasites per mL. The diluted clinical sample was lysed at a ratio of 1 mL whole blood to 3 mL lysis buffer. An assay calibrator comprising a *B. microti* IVT panel at 500 c/mL was also used. Similar to the screening described in the above examples, a single TCO was added to TCR at 5 pmoles per reaction, One T7 promoter provider and one non-T7 primer were added to Amplification Reagent at 10 pmoles per reaction each. The Probe reagent in this round of screening consisted of SEQ ID NO:37 detection probe oligomer at 2.5e6 RLU per reaction and SEQ ID NO:42 detection probe oligomer at 5e6 RLU per reaction.

TABLE 14

Conditions 1-8 Tested on Panther

| Condition # | Target Capture Oligo | T7 Primer | Non-T7 Primer | Probe |
|---|---|---|---|---|
| 1 | SEQ ID NO: 43 | SEQ ID NO: 1 | SEQ ID NO: 11 | SEQ ID NO: 37 |
| 2 | SEQ ID NO: 43 | SEQ ID NO: 1 | SEQ ID NO: 27 | SEQ ID NO: 39 |
| 3 | SEQ ID NO: 43 | SEQ ID NO: 1 | SEQ ID NO: 27 | SEQ ID NO: 38 |
| 4 | SEQ ID NO: 43 | SEQ ID NO: 1 | SEQ ID NO: 13 | SEQ ID NO: 37 |
| 5 | SEQ ID NO: 43 | SEQ ID NO: 3 | SEQ ID NO: 21 | SEQ ID NO: 37 |
| 6 | SEQ ID NO: 43 | SEQ ID NO: 7 | SEQ ID NO: 21 | SEQ ID NO: 37 |
| 7 | SEQ ID NO: 43 | SEQ ID NO: 7 | SEQ ID NO: 27 | SEQ ID NO: 39 |
| 8 | SEQ ID NO: 43 | SEQ ID NO: 5 | SEQ ID NO: 21 | SEQ ID NO: 37 |

TABLE 15

Sequences for Oligos listed in Table 14.

| Reagent | Short name | Sequence 5'-3' |
|---|---|---|
| TCR | SEQ ID NO: 43 | uaggccaauacccuaccgu cctttaaaaaaaaaaaaa aaaaaaaaaaaaaaaa |
| Amplification | SEQ ID NO: 1 | aatttaatacgactcacta tagggagattcacctctga cagttaaatacgaa |
|  | SEQ ID NO: 3 | aatttaatacgactcacta tagggagaacagttaaata cgaatgcccccaa |
|  | SEQ ID NO: 5 | aatttaatacgactcacta tagggagattcacctctga cagttaaatac |
|  | SEQ ID NO: 7 | aatttaatacgactcacta tagggagagctttcgcagt agttcgtctttaacaaatc |
|  | SEQ ID NO: 13 | cttgaatactacagcatgg aataa |
|  | SEQ ID NO: 21 | agaaaactagagtgtttcaa |
|  | SEQ ID NO: 27 | atggaataatgaagtaggac |
| Probe | SEQ ID NO: 37 | ugaaguaggacuuugguucu |
|  | SEQ ID NO: 38 | uaaugguuaauaggagcagu ug |
|  | SEQ ID NO: 39 | aguaaugguuaauaggagca |

TABLE 16

Conditions 9-14 tested on Panther

| Condition # | Target Capture Oligo | T7 Primer | Non-T7 Primer | Probe |
|---|---|---|---|---|
| 9 | SEQ ID NO: 43 | SEQ ID NO: 7 | SEQ ID NO: 21 | SEQ ID NOs: 37 + 42 |
| 10 | SEQ ID NO: 43 | SEQ ID NO: 7 | SEQ ID NO: 32 | SEQ ID NOs: 37 + 42 |
| 11 | SEQ ID NO: 43 | SEQ ID NO: 7 | SEQ ID NO: 33 | SEQ ID NOs: 37 + 42 |

TABLE 16-continued

Conditions 9-14 tested on Panther

| Condition # | Target Capture Oligo | T7 Primer | Non-T7 Primer | Probe |
|---|---|---|---|---|
| 12 | SEQ ID NO: 43 | SEQ ID NO: 7 | SEQ ID NO: 34 | SEQ ID NOs: 37 + 42 |
| 13 | SEQ ID NO: 43 | SEQ ID NO: 7 | SEQ ID NO: 35 | SEQ ID NOs: 37 + 42 |
| 14 | SEQ ID NO: 43 | SEQ ID NO: 7 | SEQ ID NO: 36 | SEQ ID NOs: 37 + 42 |

TABLE 17

Sequences for Oligos listed in Table 16.

| Reagent | SEQ ID NO: | Sequence 5'-3' |
|---|---|---|
| TCR | SEQ ID NO: 43 | uaggccaauacccuaccgu ccttta aaaaaaaaaaaa aaaaaaaaaaaaaaa |
| Amplification | SEQ ID NO: 7 | aatttaatacgactcacta tagggagagcttt cgcagt agttcgtctttaacaaatc |
|  | SEQ ID NO: 21 | agaaaactagagtgtttcaa |
|  | SEQ ID NO: 32 | agaaaactagagtgtttca |
|  | SEQ ID NO: 33 | agaaaattagagtgtttcaa |
|  | SEQ ID NO: 34 | gagaaaactagagtgtttcaa |
|  | SEQ ID NO: 35 | gagaaaattagagtgtttcaa |
|  | SEQ ID NO: 36 | tgagaaaactagagtgtttc |
| Probe | SEQ ID NO: 37 | ugaaguaggacuuugguucu |
|  | SEQ ID NO: 42 | aguaggacuuugguucu |

Results:

An analyte signal cutoff of 100,000 RLU was used to determine reactivity for specimens screened for Conditions 1-8 in Table 18. Samples above this cutoff were considered reactive. Conditions 1 and 4 yielded a false positive in lysed negative whole blood specimens at a rate of 11% and 33%, respectively. Conditions 2, 5 and 8 detected *Babesia* at less than 100% in lysed *Babesia*-infected clinical samples at 10 and 3 parasites per mL. Due to the high rate of false positives with SEQ ID NO:1 promoter provider and the high number of lower performing candidates, additional screening was performed to identify alternative candidates.

TABLE 18

Average Analyte Results for Conditions 1-9 testing lysed Clinical Sample Dilutions on the Panther System.

| Condition # | Sample Description | Valid | Reactive | % Reactive | Average Analyte RLU | StdDev Analyte RLU |
|---|---|---|---|---|---|---|
| 1 | *B. microti* Calibrator | 3 | 3 | 100% | 2,895,211 | 95,178 |
|  | *Babesia* ARC 0 p/mL | 9 | 1 | 11% | 43,072 | 111,361 |
|  | *Babesia* ARC 3 p/mL | 9 | 9 | 100% | 2,881,463 | 51,926 |
|  | *Babesia* ARC 10 p/mL | 9 | 9 | 100% | 2,947,197 | 42,332 |
|  | *Babesia* ARC 30 p/mL | 9 | 9 | 100% | 2,921,132 | 65,204 |
| 2 | *B. microti* Calibrator | 3 | 3 | 100% | 2,164,104 | 85,510 |
|  | *Babesia* ARC 0 p/mL | 9 | 0 | 0% | 655 | 63 |
|  | *Babesia* ARC 3 p/mL | 9 | 6 | 67% | 1,263,656 | 996,750 |
|  | *Babesia* ARC 10 p/mL | 9 | 9 | 100% | 2,134,186 | 27,346 |
|  | *Babesia* ARC 30 p/mL | 9 | 9 | 100% | 2,167,935 | 51,972 |
| 3 | *B. microti* Calibrator | 3 | 3 | 100% | 5,202,778 | 356,597 |
|  | *Babesia* ARC 0 p/mL | 9 | 0 | 0% | 1,460 | 140 |
|  | *Babesia* ARC 3 p/mL | 9 | 9 | 100% | 5,018,781 | 930,364 |
|  | *Babesia* ARC 10 p/mL | 9 | 9 | 100% | 5,282,309 | 286,096 |
|  | *Babesia* ARC 30 p/mL | 9 | 9 | 100% | 5,347,545 | 183,066 |
| 4 | *B. microti* Calibrator | 3 | 3 | 100% | 2,847,426 | 127,963 |
|  | *Babesia* ARC 0 p/mL | 9 | 3 | 33% | 248,507 | 581,559 |
|  | *Babesia* ARC 3 p/mL | 9 | 9 | 100% | 2,970,739 | 88,830 |
|  | *Babesia* ARC 10 p/mL | 9 | 9 | 100% | 3,007,234 | 76,308 |
|  | *Babesia* ARC 30 p/mL | 9 | 9 | 100% | 3,034,392 | 82,795 |
| 5 | *B. microti* Calibrator | 3 | 3 | 100% | 2,614,010 | 43,029 |
|  | *Babesia* ARC 0 p/mL | 9 | 0 | 0% | 1,103 | 519 |
|  | *Babesia* ARC 3 p/mL | 9 | 7 | 78% | 1,714,505 | 1,012,100 |
|  | *Babesia* ARC 10 p/mL | 9 | 6 | 67% | 1,372,599 | 1,250,728 |
|  | *Babesia* ARC 30 p/mL | 9 | 9 | 100% | 2,455,769 | 54,600 |
| 6 | *B. microti* Calibrator | 3 | 3 | 100% | 2,849,900 | 59,411 |
|  | *Babesia* ARC 0 p/mL | 9 | 0 | 0% | 765 | 72 |
|  | *Babesia* ARC 3 p/mL | 9 | 9 | 100% | 2,784,938 | 77,517 |
|  | *Babesia* ARC 10 p/mL | 9 | 9 | 100% | 2,741,662 | 63,328 |
|  | *Babesia* ARC 30 p/mL | 9 | 9 | 100% | 2,734,625 | 46,780 |
| 7 | *B. microti* Calibrator | 3 | 3 | 100% | 5,706,224 | 96,503 |
|  | *Babesia* ARC 0 p/mL | 9 | 0 | 0% | 3,383 | 1,376 |
|  | *Babesia* ARC 3 p/mL | 9 | 9 | 100% | 5,192,042 | 511,510 |
|  | *Babesia* ARC 10 p/mL | 9 | 9 | 100% | 5,240,227 | 135,033 |

TABLE 18-continued

Average Analyte Results for Conditions 1-9 testing lysed Clinical Sample Dilutions on the Panther System.

| Condition # | Sample Description | Valid | Reactive | % Reactive | Average Analyte RLU | StdDev Analyte RLU |
|---|---|---|---|---|---|---|
|  | *Babesia* ARC 30 p/mL | 9 | 9 | 100% | 5,425,945 | 228,652 |
| 8 | *B. microti* Calibrator | 3 | 3 | 100% | 2,963,935 | 70,693 |
|  | *Babesia* ARC 0 p/mL | 9 | 0 | 0% | 1,163 | 596 |
|  | *Babesia* ARC 3 p/mL | 9 | 5 | 56% | 1,708,479 | 1,623,206 |
|  | *Babesia* ARC 10 p/mL | 9 | 9 | 100% | 3,060,059 | 187,482 |
|  | *Babesia* ARC 30 p/mL | 9 | 9 | 100% | 3,112,370 | 83,507 |

In the previous round of screening, only a few candidates showed good sensitivity and specificity for lysed *Babesia*-infected clinical samples. Condition 6 had good specificity and sensitivity detecting the lysed clinical sample down to 3 parasites per mL at 100% reactivity and with strong analyte signal for the positive specimens tested and low analyte signal for negative specimens. Additional screening was performed on the Panther system using SEQ ID NO:7 promoter provider paired with a number of additional non-T7 primers. Conditions in this round of screening were again tested using lysed dilutions of a clinical sample. All conditions except Condition 11 detected the 30 and 10 p/mL lysates at 100% reactivity. None of conditions yielded any false positives in negative specimens.

sample in this example, Conditions 3 and 6 were the best candidates in terms of specificity and sensitivity. Condition 12 had the best performance of the conditions screened in Conditions 9-14. Condition 12 had best performance in terms of percent reactivity for all levels tested and consistent RLU signal for all levels tested for *Babesia* species IVTs and lysed clinical sample dilutions on the Panther system. Additionally, Condition 12 had the lowest analyte signal for negative specimens.

From the foregoing, it will be appreciated that, although specific embodiments have been described herein for purposes of illustration, various modifications may be made without deviating from the spirit and scope of this explicit

TABLE 19

Average Analyte Results for Conditions 9-14 testing lysed Wadsworth Center (WC) sample dilutions on Panther.

| Condition # | Sample Description | Level | Valid | Reactive | % Reactive | Average Analyte RLU | StdDev Analyte RLU |
|---|---|---|---|---|---|---|---|
| 9 | Negative Calibrator | 0 | 3 | 0 | 0 | 3,064 | 2,870 |
|  | *B. microti* Calibrator | 500 c/mL | 3 | 3 | 100 | 2,634,036 | 20,467 |
|  | *Babesia* WC | 30 p/mL | 5 | 5 | 100 | 2,335,851 | 100,942 |
|  |  | 10 p/mL | 5 | 5 | 100 | 1,970,484 | 170,746 |
|  | Negative | 0 | 5 | 0 | 0 | 1,229 | 1,061 |
| 10 | Negative Calibrator | 0 | 3 | 0 | 0 | 2,083 | 1,176 |
|  | *B. microti* Calibrator | 500 c/mL | 3 | 3 | 100 | 2,612,367 | 134,872 |
|  | *Babesia* WC | 30 p/mL | 5 | 5 | 100 | 1,700,198 | 40,527 |
|  |  | 10 p/mL | 5 | 5 | 100 | 1,639,511 | 112,124 |
|  | Negative | 0 | 5 | 0 | 0 | 879 | 899 |
| 11 | Negative Calibrator | 0 | 3 | 0 | 0 | 1,687 | 1,471 |
|  | *B. microti* Calibrator | 500 c/mL | 3 | 3 | 100 | 2,476,171 | 150,100 |
|  | *Babesia* WC | 30 p/mL | 5 | 5 | 100 | 2,083,998 | 176,018 |
|  |  | 10 p/mL | 5 | 3 | 60 | 833,006 | 790,769 |
|  | Negative | 0 | 5 | 0 | 0 | 2,237 | 1,256 |
| 12 | Negative Calibrator | 0 | 3 | 0 | 0 | 370 | 640 |
|  | *B. microti* Calibrator | 500 c/mL | 3 | 3 | 100 | 2,742,289 | 194,078 |
|  | *Babesia* WC | 30 p/mL | 5 | 5 | 100 | 2,220,041 | 241,385 |
|  |  | 10 p/mL | 5 | 5 | 100 | 2,098,119 | 175,399 |
|  | Negative | 0 | 5 | 0 | 0 | 970 | 648 |
| 13 | Negative Calibrator | 0 | 3 | 0 | 0 | 18 | 31 |
|  | *B. microti* Calibrator | 500 c/mL | 3 | 3 | 100 | 2,618,344 | 183,612 |
|  | *Babesia* WC | 30 p/mL | 5 | 5 | 100 | 1,861,428 | 170,146 |
|  |  | 10 p/mL | 5 | 5 | 100 | 2,032,573 | 300,759 |
|  | Negative | 0 | 5 | 0 | 0 | 405 | 871 |
| 14 | Negative Calibrator | 0 | 3 | 0 | 0 | 673 | 843 |
|  | *B. microti* Calibrator | 500 c/mL | 3 | 3 | 100 | 2,656,960 | 89,493 |
|  | *Babesia* WC | 30 p/mL | 5 | 5 | 100 | 2,523,855 | 87,845 |
|  |  | 10 p/mL | 5 | 5 | 100 | 2,376,263 | 191,838 |
|  | Negative | 0 | 5 | 0 | 0 | 2,381 | 4,735 |

CONCLUSION

Considering results for secondary screening with *Babesia* species IVTs in Example 2 and screening with clinical disclosure. Accordingly, the invention is not limited by the explicit disclosure. All publications, patents, and patent applications cited herein are hereby incorporated by reference in their entireties for all purposes.

Example 4: *Babesia* IVTs and *Babesia* Positive Whole Blood Sample Screening

Objective

Candidate amplification systems were screened on the Procleix Panther System to determine the oligo candidates in terms of specificity and sensitivity using IVTs and a contrived *Babesia* clinical sample.

Materials and Methods

Candidate amplification systems were tested on the automated Procleix Panther system. Combinations tested are listed in Table 20. Sequences for each oligo are listed in Table 21. A total of 8 conditions were screened. Conditions were screened using 16 replicates of panel members consisting of in-vitro transcript diluted in buffer for *B. microti*, *B. divergens*, *B. duncani*, and *B. venatorum* (SEQ ID NOs: 61, 62, 63, & 100) at either 30 c/mL or 10 c/mL. Conditions were also screened against 12 replicates each of a contrived clinical sample. The contrived clinical sample comprised a mixture of *Babesia*-negative human whole blood and *Babesia microti*-infected hamster whole blood (acquired from the American Red Cross (ARC)). In short, *Babesia microti* infected hamster blood having a predetermined parasitemia value was diluted with *Babesia*-negative human whole blood to yield an estimated 4 parasites/mL (p/mL) of an infected blood mixture. The infected blood mixture was then lysed at a 1 to 3 ratio (here using 0.9 mL of whole blood in 2.7 mL of an aqueous solution of 100 mM TRIS, 30 mM magnesium chloride, and 6% (v/v) LLS, at pH 7.5). The lysed infected blood mixture is referred to herein as a hamster blood lysate. In some test conditions hamster blood lysate was further diluted in negative lysate to a level equating to 0.01 parasites/mL. A negative lysate was prepared according to the same procedure. An assay positive calibrator consisted of a *B. microti* in-vitro transcript (IVT) (SEQ ID NO:61) panel at 500 c/mL. Negative calibrator and negative buffered specimens contained only buffer. Assay Reagents used consisted of: Target Capture Reagent (TCR) comprising of a single Target Capture Oligo (TCO) added at a concentration of approximately 5 pmoles per reaction; Amplification Reagent comprising of T7 and NT7 primers added at a concentration of approximately 5 pmoles each per reaction; Probe reagent consisting of acridinium-ester (AE) labeled probes added at a total concentration of approximately 1e6 Relative Light Units (RLU) per reaction. Commercially available Procleix Ultrio Plus Enzyme and Selection reagents were used.

TABLE 20

Conditions 1-8 Tested on Panther

| Condition # | Oligo Combination |
|---|---|
| 1 | SEQ ID NO: 89, SEQ ID NO: 7, SEQ ID NO: 82, SEQ ID NO: 84, SEQ ID NO: 34, SEQ ID NO: 86, SEQ ID NO: 91, SEQ ID NO: 42, SEQ ID NO: 98 |
| 2 | SEQ ID NO: 87, SEQ ID NO: 7, SEQ ID NO: 82, SEQ ID NO: 84, SEQ ID NO: 34, SEQ ID NO: 86, SEQ ID NO: 91, SEQ ID NO: 42, SEQ ID NO: 98 |
| 3 | SEQ ID NO: 43, SEQ ID NO: 87, SEQ ID NO: 89, SEQ ID NO: 82, SEQ ID NO: 84, SEQ ID NO: 34, SEQ ID NO: 86, SEQ ID NO: 91, SEQ ID NO: 42, SEQ ID NO: 98 |
| 4 | SEQ ID NO: 43, SEQ ID NO: 87, SEQ ID NO: 89, SEQ ID NO: 7, SEQ ID NO: 82, SEQ ID NO: 84, SEQ ID NO: 91, SEQ ID NO: 42, SEQ ID NO: 98 |
| 5 | SEQ ID NO: 43, SEQ ID NO: 87, SEQ ID NO: 89, SEQ ID NO: 7, SEQ ID NO: 82, SEQ ID NO: 86, SEQ ID NO: 91, SEQ ID NO: 42, SEQ ID NO: 98 |
| 6 | SEQ ID NO: 43, SEQ ID NO: 87, SEQ ID NO: 89, SEQ ID NO: 7, SEQ ID NO: 82, SEQ ID NO: 84, SEQ ID NO: 34, SEQ ID NO: 86, SEQ ID NO: 91 |
| 7 | SEQ ID NO: 43, SEQ ID NO: 87, SEQ ID NO: 89, SEQ ID NO: 7, SEQ ID NO: 82, SEQ ID NO: 84, SEQ ID NO: 34, SEQ ID NO: 86, SEQ ID NO: 92 |
| 8 | SEQ ID NO: 43, SEQ ID NO: 87, SEQ ID NO: 89, SEQ ID NO: 7, SEQ ID NO: 82, SEQ ID NO: 84, SEQ ID NO: 34, SEQ ID NO: 86, SEQ ID NO: 93 |

TABLE 21

Sequences for Oligos listed in Table 20.

| Seq # | Reagent | Class | Sequence (5'-3') |
|---|---|---|---|
| SEQ ID NO: 43 | TCR | Capture Oligo | uaggccaauacccuaccguccuuuaaaaaaaaaaaaaaaaaaaaaaaaaaaa |
| SEQ ID NO: 87 | | Capture Oligo | aaagacuuugauuucucucaagguuuaaaaaaaaaaaaaaaaaaaaaaaaaaaaaa |
| SEQ ID NO: 89 | | Capture Oligo | caagaaagagcuaucaaucugucaauccuuuaaaaaaaaaaaaaaaaaaaaaaaaaaaaaa |
| SEQ ID NO: 7 | Amplification | T7 Primer | aatttaatacgactcactatagggagagctttcgcagtagttcgtctttaacaaatc |
| SEQ ID NO: 82 | | T7 Primer | aatttaatacgactcactatagggagaggcaaatgctttcgcagtagttigtctttaaca |
| SEQ ID NO: 84 | | Non-T7 primer | gcggtaattccagctccaatag |
| SEQ ID NO: 34 | | Non-T7 primer | gagaaaactagagtgtttcaa |
| SEQ ID NO: 86 | | Non-T7 primer | cttgaatacticagca |
| SEQ ID NO: 91 | Probe | Probe | aguaggacuuugguuct |
| SEQ ID NO: 92 | | Probe | aguaggacuuugguuc |

TABLE 21-continued

Sequences for Oligos listed in Table 20.

| Seq # | Reagent | Class | Sequence (5'-3') |
|---|---|---|---|
| SEQ ID NO: 93 | | Probe | aguaggacuauugguuc |
| SEQ ID NO: 42 | | Probe | aguaggacuuugguucu |
| SEQ ID NO: 98 | | Probe | aguaggacuauugguucu |

Results:

An analyte signal cutoff calculated was calculated using negative and positive calibrators and the Panther Software. Test results yielding a signal to cutoff ratio of greater than or equal to 1.0 were considered reactive. All conditions tested detected *B. microti*, *B. divergens*, *B. duncani* and *B. venatorum* as well as the hamster blood lysate panel members to some degree (Table 22). All conditions detected all species at 100% reactivity at the 30c/mL level except Condition 5 in which 15 out of 16 replicates were detected. For conditions 1-5 all hamster blood lysate panels at 4 p/mL were 100% reactive except Condition 2 in which 8 out of 12 replicates were detected. For Conditions 6-8, which tested hamster blood lysates at 0.01 p/mL, results show 14/16, 15/16, and 14/16 positive. There were no false positive in negative reactions.

TABLE 22

Average Analyte Results for Conditions 1-8 testing.

| Condition # | Sample Description | c/mL | Valid | Reactive | % Reactive | Analyte RLUs | SD Analyte RLUs | Analyte S/CO | SD Analyte S/CO |
|---|---|---|---|---|---|---|---|---|---|
| 1 | Negative Calibrator | 0 | 3 | 0 | 0.0 | 0 | 0 | 0.00 | 0.00 |
| | Positive Calibrator | 500 | 3 | 3 | 100.0 | 1,310,257 | 45,626 | 33.33 | 1.16 |
| | B. microti | 30 c/mL | 16 | 16 | 100.0 | 691,469 | 302,377 | 17.59 | 7.69 |
| | | 10 c/mL | 16 | 15 | 93.8 | 648,137 | 282,342 | 16.49 | 7.18 |
| | B. duncani | 30 c/mL | 16 | 16 | 100.0 | 1,100,887 | 309,481 | 28.01 | 7.87 |
| | | 10 c/mL | 16 | 16 | 100.0 | 973,540 | 246,634 | 24.77 | 6.27 |
| | B. divergens | 30 c/mL | 16 | 16 | 100.0 | 1,099,778 | 294,789 | 27.98 | 7.50 |
| | | 10 c/mL | 16 | 16 | 100.0 | 959,134 | 335,825 | 24.40 | 8.54 |
| | B. venatorum | 30 c/mL | 16 | 16 | 100.0 | 1,052,533 | 280,903 | 26.78 | 7.15 |
| | | 10 c/mL | 16 | 16 | 100.0 | 902,987 | 309,501 | 22.97 | 7.87 |
| | Negative Buffer | 0 c/mL | 16 | 0 | 0.0 | 0 | 0 | 0.00 | 0.00 |
| | Hamster Blood Lysate | 4 | 12 | 12 | 100.0 | 1,307,118 | 28,853 | 33.25 | 0.73 |
| | Hamster Blood Lysate | 0 | 12 | 0 | 0.0 | 4 | 15 | 0.00 | 0.00 |
| 2 | Negative Calibrator | 0 | 3 | 0 | 0.0 | 14 | 24 | 0.00 | 0.00 |
| | Positive Calibrator | 500 | 3 | 3 | 100.0 | 1,360,358 | 88,289 | 33.32 | 2.16 |
| | B. microti | 30 c/mL | 16 | 16 | 100.0 | 990,774 | 405,235 | 24.27 | 9.93 |
| | | 10 c/mL | 16 | 13 | 81.3 | 674,210 | 358,804 | 16.52 | 8.79 |
| | B. duncani | 30 c/mL | 16 | 16 | 100.0 | 1,261,270 | 234,066 | 30.90 | 5.73 |
| | | 10 c/mL | 16 | 16 | 100.0 | 1,010,323 | 412,156 | 24.75 | 10.10 |
| | B. divergens | 30 c/mL | 16 | 16 | 100.0 | 1,136,882 | 281,770 | 27.85 | 6.90 |
| | | 10 c/mL | 16 | 16 | 100.0 | 1,138,086 | 288,726 | 27.88 | 7.07 |
| | B. venatorum | 30 c/mL | 16 | 16 | 100.0 | 1,095,242 | 357,885 | 26.83 | 8.77 |
| | | 10 c/mL | 16 | 16 | 100.0 | 979,611 | 405,233 | 24.00 | 9.93 |
| | Negative Buffer | 0 c/mL | 16 | 0 | 0.0 | 0 | 0 | 0.00 | 0.00 |
| | Hamster Blood Lysate | 4 | 12 | 8 | 66.7 | 1,148,331 | 589,637 | 28.13 | 14.44 |
| | Hamster Blood Lysate | 0 | 12 | 0 | 0.0 | 220 | 763 | 0.01 | 0.02 |
| 3 | Negative Calibrator | 0 | 3 | 0 | 0.0 | 0 | 0 | 0.00 | 0.00 |
| | Positive Calibrator | 500 | 3 | 3 | 100.0 | 1,247,077 | 16,587 | 33.33 | 0.44 |
| | B. microti | 30 c/mL | 16 | 16 | 100.0 | 996,284 | 147,903 | 26.63 | 3.95 |
| | | 10 c/mL | 16 | 14 | 87.5 | 733,412 | 225,774 | 19.60 | 6.03 |
| | B. duncani | 30 c/mL | 16 | 16 | 100.0 | 1,154,290 | 46,421 | 30.85 | 1.24 |
| | | 10 c/mL | 16 | 16 | 100.0 | 1,051,223 | 93,259 | 28.10 | 2.49 |
| | B. divergens | 30 c/mL | 16 | 16 | 100.0 | 1,160,454 | 42,968 | 31.02 | 1.15 |
| | | 10 c/mL | 16 | 16 | 100.0 | 1,067,057 | 104,387 | 28.52 | 2.79 |
| | B. venatorum | 30 c/mL | 16 | 16 | 100.0 | 1,120,866 | 52,999 | 29.96 | 1.42 |
| | | 10 c/mL | 16 | 16 | 100.0 | 988,682 | 127,271 | 26.43 | 3.40 |
| | Negative Buffer | 0 c/mL | 16 | 0 | 0.0 | 0 | 0 | 0.00 | 0.00 |
| | Hamster Blood | 4 | 12 | 12 | 100.0 | 1,153,646 | 24,699 | 30.84 | 0.66 |

TABLE 22-continued

Average Analyte Results for Conditions 1-8 testing.

| Condition # | Sample Description | c/mL | Valid | Reactive | % Reactive | Analyte RLUs | SD Analyte RLUs | Analyte S/CO | SD Analyte S/CO |
|---|---|---|---|---|---|---|---|---|---|
| | Lysate | | | | | | | | |
| | Hamster Blood Lysate | 0 | 12 | 0 | 0.0 | 0 | 0 | 0.00 | 0.00 |
| 4 | Negative Calibrator | 0 | 3 | 0 | 0.0 | 0 | 0 | 0.00 | 0.00 |
| | Positive Calibrator | 500 | 3 | 3 | 100.0 | 689,988 | 39,272 | 33.33 | 1.90 |
| | B. microti | 30 c/mL | 16 | 16 | 100.0 | 236,235 | 167,806 | 11.41 | 8.11 |
| | | 10 c/mL | 16 | 11 | 68.8 | 142,663 | 122,889 | 6.89 | 5.94 |
| | B. duncani | 30 c/mL | 16 | 16 | 100.0 | 331,217 | 55,106 | 16.00 | 2.66 |
| | | 10 c/mL | 16 | 16 | 100.0 | 174,519 | 88,419 | 8.43 | 4.27 |
| | B. divergens | 30 c/mL | 16 | 16 | 100.0 | 589,500 | 20,005 | 28.48 | 0.97 |
| | | 10 c/mL | 16 | 16 | 100.0 | 482,888 | 106,825 | 23.33 | 5.16 |
| | B. venatorum | 30 c/mL | 16 | 16 | 100.0 | 560,636 | 66,993 | 27.09 | 3.24 |
| | | 10 c/mL | 16 | 16 | 100.0 | 406,685 | 129,080 | 19.65 | 6.24 |
| | Negative Buffer | 0 c/mL | 16 | 0 | 0.0 | 0 | 0 | 0.00 | 0.00 |
| | Hamster Blood Lysate | 4 | 12 | 12 | 100.0 | 870,137 | 62,684 | 42.04 | 3.03 |
| | Hamster Blood Lysate | 0 | 12 | 0 | 0.0 | 0 | 0 | 0.00 | 0.00 |
| 5 | Negative Calibrator | 0 | 3 | 0 | 0.0 | 0 | 0 | 0.00 | 0.00 |
| | Positive Calibrator | 500 | 3 | 3 | 100.0 | 1,041,315 | 125,263 | 33.33 | 4.01 |
| | B. microti | 30 c/mL | 16 | 15 | 93.8 | 306,912 | 218,362 | 9.82 | 6.99 |
| | | 10 c/mL | 16 | 11 | 68.8 | 243,155 | 159,289 | 7.78 | 5.10 |
| | B. duncani | 30 c/mL | 16 | 16 | 100.0 | 748,753 | 281,035 | 23.97 | 9.00 |
| | | 10 c/mL | 16 | 16 | 100.0 | 751,922 | 286,380 | 24.07 | 9.17 |
| | B. divergens | 30 c/mL | 16 | 16 | 100.0 | 807,915 | 258,741 | 25.86 | 8.28 |
| | | 10 c/mL | 16 | 16 | 100.0 | 643,482 | 256,352 | 20.60 | 8.21 |
| | B. venatorum | 30 c/mL | 16 | 16 | 100.0 | 792,659 | 264,484 | 25.37 | 8.47 |
| | | 10 c/mL | 16 | 16 | 100.0 | 747,633 | 243,096 | 23.93 | 7.78 |
| | Negative Buffer | 0 c/mL | 16 | 0 | 0.0 | 0 | 0 | 0.00 | 0.00 |
| | Hamster Blood Lysate | 4 | 12 | 12 | 100.0 | 1,410,648 | 33,678 | 45.16 | 1.08 |
| | Hamster Blood Lysate | 0 | 12 | 0 | 0.0 | 84 | 210 | 0.00 | 0.01 |
| 6 | Negative Calibrator | 0 c/mL | 3 | 0 | 0.0 | 0 | 0 | 0.00 | 0.00 |
| | Positive Calibrator | 500 c/mL | 3 | 3 | 100.0 | 524,314 | 5,119 | 33.33 | 0.33 |
| | B. microti | 30 c/mL | 16 | 16 | 100.0 | 507,560 | 25,719 | 32.26 | 1.64 |
| | B. divergens | 30 c/mL | 16 | 16 | 100.0 | 471,886 | 64,616 | 30.00 | 4.11 |
| | B. duncani | 30 c/mL | 16 | 16 | 100.0 | 502,786 | 46,565 | 31.96 | 2.96 |
| | B. venatorum | 30 c/mL | 16 | 16 | 100.0 | 495,758 | 19,503 | 31.51 | 1.24 |
| | Hamster Blood Lysate | 0.01 p/mL | 16 | 14 | 87.5 | 337,759 | 102,178 | 24.48 | 7.41 |
| | Negative Buffer | 0 c/mL | 16 | 0 | 0.0 | 145 | 387 | 0.00 | 0.00 |
| 7 | Negative Calibrator | 0 c/mL | 3 | 0 | 0.0 | 254 | 439 | 0.01 | 0.02 |
| | Positive Calibrator | 500 c/mL | 3 | 3 | 100.0 | 668,273 | 11,200 | 32.91 | 0.55 |
| | B. microti | 30 c/mL | 16 | 16 | 100.0 | 654,530 | 36,463 | 32.24 | 1.80 |
| | B. divergens | 30 c/mL | 16 | 16 | 100.0 | 652,634 | 44,688 | 32.14 | 2.20 |
| | B. duncani | 30 c/mL | 16 | 16 | 100.0 | 628,767 | 49,861 | 30.97 | 2.46 |
| | B. venatorum | 30 c/mL | 16 | 16 | 100.0 | 620,345 | 63,099 | 30.55 | 3.11 |
| | Hamster Blood Lysate | 0.01 p/mL | 16 | 15 | 93.8 | 397,026 | 182,905 | 23.35 | 10.76 |
| | Negative Buffer | 0 c/mL | 16 | 0 | 0.0 | 91 | 151 | 0.00 | 0.00 |
| 8 | Negative Calibrator | 0 | 3 | 0 | 0.0 | 280 | 486 | 0.02 | 0.03 |
| | Positive Calibrator | 500 c/mL | 3 | 3 | 100.0 | 521,485 | 14,518 | 32.74 | 0.91 |
| | B. microti | 30 c/mL | 16 | 16 | 100.0 | 460,267 | 52,434 | 28.90 | 3.29 |
| | B. divergens | 30 c/mL | 16 | 16 | 100.0 | 423,530 | 61,700 | 26.59 | 3.87 |

TABLE 22-continued

Average Analyte Results for Conditions 1-8 testing.

| Condition # | Sample Description | c/mL | Valid | Reactive | % Reactive | Analyte RLUs | SD Analyte RLUs | Analyte S/CO | SD Analyte S/CO |
|---|---|---|---|---|---|---|---|---|---|
| | B. duncani | 30 c/mL | 16 | 16 | 100.0 | 428,292 | 43,574 | 26.89 | 2.74 |
| | B. venatorum | 30 c/mL | 16 | 16 | 100.0 | 415,273 | 64,983 | 26.07 | 4.08 |
| | Hamster Blood Lysate | 0.01 p/mL | 16 | 14 | 87.5 | 198,996 | 127,811 | 13.96 | 8.97 |
| | Negative Buffer | 0 c/mL | 16 | 0 | 0.0 | 817 | 885 | 0.00 | 0.00 |

CONCLUSION

Oligo combinations tested herein exemplify specific and sensitive capture, amplification, and detection of *Babesia* species including *B. microti, B. divergens, B. duncani,* and *B. ventorum* and demonstrated detection of *Babesia microti* parasite in whole blood.

| SEQ ID NO. | Sequence (5' to 3') | Comments |
|---|---|---|
| 1 | aatttaatacgactcactatagggagattcacctctgacagttaaatacgaa | T7 promoter primer |
| 2 | ttcacctctgacagttaaatacgaa | SEQ ID NO: 1 without promoter sequence |
| 3 | aatttaatacgactcactatagggagaacagttaaatacgaatgccccaa | T7 promoter primer |
| 4 | acagttaaatacgaatgccccaa | SEQ ID NO: 3 without promoter sequence |
| 5 | aatttaatacgactcactatagggagattcacctctgacagttaaatac | T7 promoter primer |
| 6 | ttcacctctgacagttaaatac | SEQ ID NO: 5 without promoter sequence |
| 7 | aatttaatacgactcactatagggagagctttcgcagtagttcgtcatttaacaaatc | T7 promoter primer |
| 8 | gctttcgcagtagttcgtctttaacaaatc | SEQ ID NO: 7 without promoter sequence |
| 9 | aatttaatacgactcactatagggagactttcgcagtagttcgtctttaac | T7 promoter primer |
| 10 | ctttcgcagtagttcgtctttaac | SEQ ID NO: 9 without promoter sequence |
| 11 | cttgaatactacagcatgga | Non-T7 primer |
| 12 | actacagcatggaataatga | Non-T7 primer |
| 13 | cttgaatactacagcatggaataa | Non-T7 primer |
| 14 | acttcagcatggaataatga | Non-T7 primer |
| 15 | cttgaatacttcagcatgga | Non-T7 primer |
| 16 | actncagcatggaataatga | Non-T7 primer, wherein "n" means a or g or c or t/u, or unknown, or other (WIPO Standard ST.25 (1998), Appendix 2, Table 1) |

-continued

| SEQ ID NO. | Sequence (5' to 3') | Comments |
|---|---|---|
| 17 | actwcagcatggaataatga | Non-T7 primer |
| 18 | cttgaatactncagcatgga | Non-T7 primer, wherein "n" means a or g or c or t/u, or unknown, or other (WIPO Standard ST.25 (1998), Appendix 2, Table 1) |
| 19 | cttgaatactwcagcatgga | Non-T7 primer |
| 20 | actttgagaaaactagagtg | Non-T7 primer |
| 21 | agaaaactagagtgtttcaa | Non-T7 primer |
| 22 | ataatgaagtaggactttgg | Non-T7 primer |
| 23 | aggactttggttctatttg | Non-T7 primer |
| 24 | ggttctattttgttggtt | Non-T7 primer |
| 25 | tggttctattttgttgg | Non-T7 primer |
| 26 | ggaataatgaagtaggacttt | Non-T7 primer |
| 27 | atggaataatgaagtaggac | Non-T7 primer |
| 28 | atggaataatgaagtagg | Non-T7 primer |
| 29 | gcatggaataatgaagtag | Non-T7 primer |
| 30 | tacagcatggaataatgaag | Non-T7 primer |
| 31 | tactacagcatggaataatg | Non-T7 primer |
| 32 | agaaaactagagtgtttca | Non-T7 primer |
| 33 | agaaaattagagtgtttcaa | Non-T7 primer |
| 34 | gagaaaactagagtgtttcaa | Non-T7 primer |
| 35 | gagaaaattagagtgtttcaa | Non-T7 primer |
| 36 | tgagaaaactagagtgtttc | Non-T7 primer |
| 37 | ugaaguaggacuuugguucu | Probe |
| 38 | uaaugguuaauaggagcaguug | Probe |
| 39 | aguaaugguuaauaggagca | Probe |
| 40 | ggacuuugguucuauuuuguugg | Probe |
| 41 | aaugguuaauaggagcaguuggggg | Probe |
| 42 | aguaggacuuugguucu | Probe |
| 43 | uaggccaauacccuaccguccuuuaaaaaaaaaaaaaaaaaaaaaaaaaaaaaa | Target capture |
| 44 | uaggccaauacccuaccgucc | SEQ ID NO: 43, without capture tail sequence |
| 45 | atggaataatgaagtag | Same sequence in SEQ ID NOs: 27, 28, 29 and 31 |
| 46 | agaaaactagagtg | Same sequence in SEQ ID NOs: 20, 21, 32, 34 and 36 |
| 47 | agaaaattagagtg | Same sequence in SEQ ID NOs: 33 and 35. |

-continued

| SEQ ID NO. | Sequence (5' to 3') | Comments |
|---|---|---|
| 48 | agaaaaytagagtg | Substitutes y for c in SEQ ID NO: 46 and y for t in SEQ ID NO: 47, wherein "y" means c or t/u (WIPO Standard ST.25 (1998), Appendix 2, Table 1) |
| 49 | agaaaactagagtgtttc | Same sequence in SEQ ID NOs: 19, 20, 21, 32, 34 and 36. |
| 50 | agaaaattagagtgtttc | Same sequence in SEQ ID NOs: 33 and 35. |
| 51 | agaaaaytagagtgtttc | Substitutes y for c in SEQ ID NO: 49) and y for t in SEQ ID NO: 50, wherein "y" means c or t/u (WIPO Standard ST.25 (1998), Appendix 2, Table 1) |
| 52 | tactacagcatggaataa | Same sequence in SEQ ID NO: 13 and 31. |
| 53 | actncagcatgga | Residue "n" means a or g or c or t/u, or unknown, or other (WIPO Standard ST.25 (1998), Appendix 2, Table 1), and "other preferably means "i" or inosine |
| 54 | actwcagcatgga | |
| 55 | actacagcatgga | Same sequence as SEQ ID NO: 54, except that "n" is "a". |
| 56 | gtatttaactgt | Same sequence in SEQ ID NOs: 1, 3 and 5. |
| 57 | Gtatttaactgtcagaggtgaa | Same sequence in SEQ ID NOs: 1 and 5. |
| 58 | aatttaatacgactcactatagggaga | T7 promoter |
| 59 | aguaggacuuugguucu | Same sequence in SEQ ID NO: 42. |
| 60 | uaaugguuaauaggagca | Same sequence in SEQ ID NOs: 38 and 39. |
| 61 | gggcgaauuggguaccgggccccccucgaggucgacgcuuaguauaagcuuuua uacagcgaaacugcgaauggcucauuaaaacaguuauaguuuauuugauguucgu uuuacauggauaaccguggualuucuagggcuaaauacaugcucgaggcgcguuu cgcguggcguuuauuagacuuuaaccaacccuucggguaaucggugauucauaau aaauuagcgaaucgcauggcuuugccggcgauguaucauucaaguuucugaccua ucagcuuuggacgguagggauuggccuaccggggcgacgacgggugacggggaa uuggggulucgauuccggagagggagccugagaaacggcuaccacaucuaaggaag gcagcaggcgcgcaaauuacccaauccugacacaggaggulaguagugacaagaaauaa | B. microti IVT Sequence |

| SEQ ID NO. | Sequence (5' to 3') | Comments |
|---|---|---|
| | caauacagggcuuaaagucuuguaauuggaaugaugggaaucuaaacccuuccca gaguaucaauuggagggcaagucuggugccagcagccgcgguaauuccagcucca auagcguauauuaaaguuguugcaguuaagaagcucguaguugaauuucugccuu gucauuaaucucgcuuccgagcguuuuuuauugacuuggcaucuucuggauuu ggugccuucggguacuauuuccaggauuuacuuugagaaaacuagagguguuuca aacaggcauucgccuugaauacuacagcauggaauaaugaaguaggacuuuggu cuauuuuguuggguuaauugagccagaguaaugguuaauaggagcaguuggggca uucguauuuaacugucagagggugaaauucuuagauuuguuaaagacgaacuacug cgaaagcauuugccaaggaugguuucauuaaucaagaacgaaaguuaggggaucg aagacgaucagauaccgucguaguccuaaccauaaacuaugccgacuagagauugg aggucgucaguuaaacgacuccuucagcaccuugagagaaacaaagucuuugg guucgggggggaguauggucgcaagucugaaacuuaaaggaauugacggaagggc accaccaggcguggagccugcggcuuaauuugacucaacacgggaaaccucaccag guccagacauagagaggauugacagauugauagcucuuucuugaugaauu | |
| 62 | gggcgaauugggguaccggggccccccccucgaggucgacgguaucgauaagcuugau aucgaauuccugcagcccggggguauccaaccugguugauccugccaguagucaua ugcuugucuuaaagauuaagccaugcaugucuaaguacaaacuuuuuacggugaa acugcgaauggcucauuacaacaguuauaguuucuuuggguauucguuuuccaugg auaaccgugcuaauuguagggcuaauacaaguucgaggccuuuggcggcguuua uuaguucuaaaaccaucccuuuugguuuucgguugauucauaauaaacuugcgaau cgcaauuuuugcgauggaccauucaaguuucugacccaucagcuugacgguagg guauuggccuaccgaggcagcaacgggguaacggggaauuaggguucgauuccgga gagggagccugagaaacggcuaccacaucccaaggaaggcagcaggcgcgcaaauua cccaauccugacacagggagguagugacaagaaauaacaauacagggcaauugucu uguaauuggaaugaugguggaccuaaaccccucaccagaguaacaauuggaggggcaa gucuggugccagcagccgcgguaauuccagcuccaauagcguauauuaaacuugu ugcaguuaaaaagcucguaguugaauuuuugcguggguguaauauuugacuaaug ucgagauugcacuucgcuuuugggauuuaucccuuuuacuuugagaaaauuaga guguuucaagcagacuuuugucuugaauacuucagcauggaauaauagaguagga cuuuggguucuauuuuguuguuugugaaccuuaguaauugguuaauaggaacggu uggggggcauucguauuuaacugucagagggugaaauucuuagauuuguuaaagacg aacuacugcgaaagcauuugccaaggacguuuucauuaaucaagaacgaaaguuag gggaucgaagacgaucagauaccgucguaguccuaaccauaaacuaugccgacuag gauuggaggucgucauuuuccgacuccuucagcaccuugagagaaaucaaagu cuuuggguucggggggaguauggucgcaaggcugaaacuuaaaggaauugacg gaagggcaccaccaggcguggagccugcggcuuaauuugacucaacacggggaaac ucaccagguccagacaauguuaggauugacagauugauagcucuuucuugauucu uugggguggugcggcc | B. divergens IVT Sequence |
| 63 | gggcgaauugggguaccggggccccccccucgaggucgacguugauccugccaguagu cauaugcuugucuuaaagauuaagccaugcaugucuaaguauaaacuuuuuauaug gugaaacugcgaauggcucauuacaacaguuauaguuuauuugaagucguuuuu acauggauaaccgugcuaauuguagggcuaauacaugcugcgaggccuuggcucccu gucuuggcugcguuuauuagacucgaaaccuucccgcuugcgguacucggugauu cauaauaaauuugcgaaucgcauggcuuuugccggcgaugguucauucaaguuuc ugaccuaucagcuuuugacgguagggguauuggccuaccggggcagcgacggguaa cggggaauuaggguucgauuccgagagggagccugagaaacggcuaccacaucu aaggaaggcagcaggcgcgcaaauuacccaauacggacaccgugagguagugacaa gaaauaacaauacagggcuuaaagcuuuguaauuggaaugaugggaauccaaaccc cuuccagaguaucaauuggagggcaagucuggugccagcagccgcgguaauuccag cgcuccaauagcguauauuaaacuugguugcaguuaaaaagcucguaguugaacuuc ugccgcuuggccuuucgucccuuggguuucgucgccugguggcuuaccuc uggcgguguucuccauuugccaguuuuacuuugagaaauuagaguguuucaa gcagguuuugccuugaauacuucagcauggaauaauaaaguaggacuuugguc uauuuuguggguuucaggaccaaaguaauggguuaaauaggaacaguuggggcau ucguauuuaacgucagagggugaaauucuuagauuuguuaaagacgaacuacugc gaaagcauuugccaaggaugguuucauuaaucaagaacgaaaguuaggggcucga agacgaucagauaccgucguaguccuaaccauaaacuaugccgacuagagauugga ggucgucauuuaaacgacuccuucagcaccuugagagaaaucaaagucuuuggg uucgggggauauggucgcaaggcugaaacuuaaaggaauugacggaagggca ccaccaggcguggagccugcggcuuaauuugacucaacacggggaaccucaccagg uccagacauaguuaggauugacagauugauagcucgaauu | B. duncani IVT Sequence |
| 64 | gggcgaauuggguaccguagaaacugcgaacggcucauuaaaacaguuauagucu acuugacauuuuauuauaaggauaacuacgaaaagcuguagcuaauacuugcu uuauuauccuuugauuuuuaucuuuggauaaguauuuguuaggccuuauaagaa aaaaguuauuaacuuaaggaauuauaacaaagaaguaacacguaauaaauuuauuu uauuuaguguguaucaaucgaguuucugaccuaucagcuuuugauguuaggguua uuggccuaacauggcuaugacggguaacggggaauuagaguucgauuccggagag ggagccugagaaauagcuaccacacuuaaggaaggcagcaggcgcgcaaauuaccc aauucaaaaagagagguagugacaagaaauaacaauacaaggccaauuuuuggu uuguaauuggaaugaugguggaauuuaaaccuucccagaguaacaauuggagggc aagucuggugccagcagccgcgguaauuccagcuccaauagcguauauuaaaauu guugcaguuaaaacgcucguaguugaauuucaaagaaucgauauuuauuguaac uauucuagggggaacuauuuuagguuuucgcuuuaauacgcuuccucuauauuauu | P. falciparum IVT Sequence |

| SEQ ID NO. | Sequence (5' to 3') | Comments |
|---|---|---|
| | guucuuuaaauaacaaagauucuuuuuaaaaucccacuuuugcuuuuuggggaauuuguuacuuugaauaaauuagaggugucaaagcaaacaguuaaagcauuuacuguguuugaauacuauagcauggaauaacaaaauugaacaagcuaaaauuuuugucuuuuucuuauuuugcuuaguuacgauuaauaggaguagcuuggggacauucguauucagaugucagaggugaaauucuuagauuuucuggagacgaacaacugcgaaagcauuugucuaaaauacuuccauuaaucaagaacgaaaguuaagggagugaagacgaucagauaccgucguaaucuuaaccauaaacuaugccgacuaggguguuggaugaaaguguuaaaaauaaaagucaucuuucuaggugacuuuuagauugcuuccuucaguaccuuaugagaaaucaaagucuuugguucuggggcgaguauucgcgcaagcgagaaaguuaaaagaauugacggaagggcaccaccaggcguggagcuugcggcuuaauuugacucaacacggggaaacucacuaguuuaagacaagaguaggauugacagauuaauagcucuuucuugauuucuuggaugugaugcauggccguuuuuaguucgugaauaugauuugucugguuaauuccgauaacgaacgagaucggauccacuaguucuagagcggcc | |
| 65 | ugaaguaggacuuugguucuauuuguuggguuauugagccagaguaauggguuaauaggagcaguuggggg | |
| 66 | ttcacctctgacagttaaatacgaatgcccccaa | Contains SEQ ID NOs: 56 and 57, which the target hybridising sequence can contain |
| 67 | tactncagcatggaataatgaagtaggactttgg | Contains SEQ ID NOs: 45 & 69, wherein "n" means a or g or c or t/u, or unknown, or other (WIPO Standard ST.25 (1998), Appendix 2, Table 1) |
| 68 | cttgaatactncagcatggaataatga | Contains SEQ ID NOs: 53, 54 or 55, which the target hybridising sequence can contain, wherein "n" means a or g or c or t/u, or unknown, or other (WIPO Standard ST.25 (1998), Appendix 2, Table 1) |
| 69 | atggaataatg | Contained in SEQ ID NO: 67 |
| 70 | actttgagaaaaytagagtgtttcaaa | Contains SEQ ID NOs: 46, 47, 48, 49, 50, and 51, wherein "y" means c or t/u (WIPO Standard ST.25 (1998), Appendix 2, Table 1) |
| 71 | aacctggttgatcctgccagtagtcatatgcttgtcttaaagattaagccatgcatgtcttagtataagcttttatacagcgaaactgcgaatggctcattaaaacagttatagtttgatgttcgttttacatggataaccgtggtaattctagggctaatacatgctcgaggcgcgtttcgcgtggcgttattagactttaaccaaccctcgggtaatcggtgattcataataaattagcgaatcgcatggcttgccggcgatgtatcattcaagtttctgacctatcagctttggacggtagggtattggcctaccggggcgacgacgggtgacggggaattgggggttcgattccggagagggagcctgagaaacggctaccacatctaaggaaggcagcaggcgcgcaaattacccaatcctgacacgggaggtagtgacaagaaataacaatacagggcttaaagtcttgtaattggaatgatgggaatctaaacccttcccagagtatcaattggagggcaagtctggtgccagcagccgcggtaattccagctccaatagcgtatattaaagttgttgcagttaagaagctcgtagttgaatttctgccttgtcattaatctcgcttccgagcgttttttttattgacttggcatcttctggatttggtgccttcgggtactattttccaggatttactttgagaaaactagagtgtttcaaacaggcattcgccttgaatactacagcatggaataatgaagtaggactttggttctatttgttggttattgagccagagtaatggttaataggagcagttgggggcattcgtatttaactgtcagaggtgaaattcttagatttgttaaagacgaactactgcgaaagcatttgccaaggatgttttcattaatcaagaacgaaagttaggggatcgaagacga | GenBank Accession No: AY693840.1 Babesia microti isolate Gray 18S ribosomal RNA gene, partial sequence |

-continued

| SEQ ID NO. | Sequence (5' to 3') | Comments |
|---|---|---|
| | tcagataccgtcgtagtcctaaccataaactatgccgactagagattggaggtcgtcagttta<br>aacgactccttcagcaccttgagagaaatcaaagtcttttgggttctgggggggagtatggtcg<br>caagtctgaaacttaaaggaattgacggaagggcaccaccaggcgtggagcctgcggctt<br>aatttgactcaacacgggaaacctcaccaggtccagacatagagaggattgacagattgata<br>gctctttcttgattctatgggtggtggtgcatggccgttcttagttggtggagtgatttgtctggtt<br>aattccgttaacgaacgagaccttaacctgctaaattaggatctgggacaagctttgctgttcc<br>agtatcgcttcttagagggactttgcgttcataaaacgcaaggaagtgtaaggcaataacag<br>gtctgtgatgcccttagatgtcctgggctgcacgcgcgctacactgatgcattcaacgagtttt<br>tccttggccgtcgggtccgggtaatcttacagtatgcatcgtgatggggatagattattgcaat<br>tattaatcttgaacgaggaatgcctagtaggcgcgagtcatcagctcgtgccgactacgtcc<br>ctgccctttgtacacaccgcccgtcgctcctaccgatcgagtgatccggtgaattattcggac<br>caagaaacgtggattcgtccttcgttttttggaaagttttgtgaaccttatcacttaaaggaagg<br>agaagtcgtaacaaggttttccgtaggtgaacctgcggaaggatcattc | |
| 72 | aacctggttgatcctgccagtagtcatatgcttgtcttaaagattaagccatgcatgtctaagta<br>caaacttttttacggtgaaactgcgaatggctcattacaacagttatagtttctttggtattcgtttt<br>ccatggataaccgtgctaattgtagggctaatacaagttcgaggcctttttggcggcgttttatta<br>gttctaaaaccatcccttttggttttcggtgattcataataaacttgcgaatcgcaattttttgcgat<br>ggaccattcaagttttctgacccatcagcttgacggtagggtattggcctaccgaggcagcaa<br>cgggtaacggggaattagggttcgattccggagagggagcctgagaaacggctaccacat<br>ccaaggaaggcagcaggcgcgcaaattacccaatcctgacacagggaggtagtgacaag<br>aaataacaatacagggcaattgtcttgtaattggaatgatggtgacctaaaccctcaccagag<br>taacaattggagggcaagtctggtgccagcagccgcggtaattccagctccaatagcgtata<br>ttaaacttgttgcagttaaaaagctcgtagttgaatttttgcgtggtgttaatattgactaatgtcg<br>agattgcacttcgcttttgggatttatccctttttactttgagaaaattagagtgtttcaagcagac<br>ttttgtcttgaatacttcagcatggaataatagagtaggactttggttctattttgttggtttgtgaa<br>cctagtaatggttaataggaacggdgggggcattcgtatttaactgtcagaggtgaaattctt<br>agatttgttaaagacgaactactgcgaaagcatttgccaaggacgttttcattaatcaagaacg<br>aaagttaggggatcgaagacgatcagataccgtcgtagtcctaaccataaactatgccgact<br>agggattggaggtcgtcattttttccgactccttcagcaccttgagagaaatcaaagtctttggg<br>ttctgggggagtatggtcgcaaggctgaaacttaaaggaattgacggaagggcaccacc<br>aggcgtggagcctgcggcttaatttgactcaacacgggaaactcaccaggtccagacaat<br>gttaggattgacagattgatagctctttcttgattctttgggtggtggtgcatggccgttcttagtt<br>ggtggagtgatttgtctggttaattccgttaacgaacgagaccttaacctgctaactagtgtcc<br>gtaaaaaggttcgtccgttacggtttgcttcttagagggactttgcggtctaagccgcaagg<br>aagtttaaggcaataacaggtctgtgatgcccttagatgtccctgggctgcacgcgcgctaca<br>ctgatgcattcatcgagttttatcccttcccgaaagggctgggtaatcttagtatgcatcgtga<br>cggggattgattttttgcaattctaaatcatgaacgaggaatgcctagtatgcgcaagtcatcag<br>cttgtgcagattacgtccctgcccttgtacacaccgcccgtcgctcctaccgatcgagtgatc<br>cggtgaattattcggaccgtggccttttccgattcgtcggcttggcctagggaagtcttgtgaa<br>ccttatcacttaaaggaaggagaagtcgtaacaaggttttccgtaggtgaacctgcggaagg<br>atcattc | GenBank Accession No: AY789076.1 Babesia divergens 18S ribosomal RNA gene, partial sequence |
| 73 | ccttggttgatcctgccagtagtcatatgcttgtcttaaggattaagccatgcatgtctaagtata<br>aacttttatatggtgaaactgcgaatggctcattacaacagttatagtttatttgaaagtcgttttt<br>acatggataaccgtgctaattgtagggctaatacatgctcgaggccttggcttctgtcttggct<br>gcgtttattagactcgaaaccttcccgcttgcggtactcggtgattcataataaatttgcgaatc<br>gcatggcttttgccggcgatggttcattcaagttttctgacctatcagctttgcacggtagggtat<br>tggcctaccggggcagcgacgggtaacggggaattagggttcgattccggagagggagc<br>ctgagaaacggctaccacatctaaggaaggcagcaggcgcgcaaattacccaatacggac<br>accgtgaggtagtgacaagaaataacaatacagggctttaagctttgtaattggaatgatggg<br>aatccaaaccccttccagagtatcaattggagggcaagtctggtgccagcagccgcggtaa<br>ttccagctccaatagcgtatattaaacttgagcagttaaaaagctcgtagttgaacttctgccg<br>cttggccttttcgttcccccttgggtttgcttcgcctggtggcttacctctggcggtggttctccat<br>tgccagttttactttgagaaaattagagtgtttcaagcaggcttttgccttgaatacttcagcat<br>ggaataataaagtaggactttggttctattttgttggtttcaggaccaaagtaatggttaatagg<br>aacagttgggggcattcgtatttaactgtcagaggtgaaattcttagatttgttaaagacgaact<br>actgcgaaagcatttgccaaggatgttttcattaatcaagaacgaaagttaggggctcgaag<br>acgatcagataccgtcgtagtcctaactataaactatgccgactagagattggaggtcgtcat<br>tttaaacgactccttcagcaccttgagagaaatcaaagtctttgggttctggggggagtatggt<br>cgcaaggctgaaacttaaaggaattgacggaagggcaccaccaggcgtggagcctgcgg<br>cttaatttgactcaacacgggaaacctcaccaggtccagacatagttaggattgacagattga<br>tagctctttcttgattctatgggtagtggtgcatggccgttcttagttggtggagtgatttgtctgg<br>ttaattccgttaacgaacgagaccttaacctgctaaatagcagctgagaataatctcttgtttca<br>gttttgcttcttagagggactttgcggtcataaatcgcaaggaagtttaaggcaataacaggtc<br>tgtgatgcccttagatgtcctgggctgcacgcgcgctacactgatgcattcatcgagttttatc<br>cttgcccgaaagggtttggtaatcttagtatgcatcgtgatggggattgattattgcaattatta<br>atcatgaacgaggaatgcctagtaggcgcgagtcatcagctcgtgccgactacgtccctgc<br>cctttgtacacaccgcccgtcgctcctaccgatcgagtgatccggtgaattattcggaccgtg<br>acgcttctaattcgttagaaatgtctagggaagttttgtgaaccttatcacttaaaggaaggag<br>aagtcgtaacaaggtaccg | GenBank Accession No: AY027815.1 Babesia sp. WA1 isolate CA5 18S ribosomal RNA gene, partial sequence |
| 74 | tcaaagattaagccatgcaagtgaaagtatatatatatttttatatgtagaaactgcgaacggctc<br>attaaaacagttatagtctacttgacatttttattataaggataactacggaaaagctgtagctaa<br>tacttgctttattatcctttgatttttatctttggataagtatttgttaggccttataagaaaaaagtta<br>ttaacttaaggaattataacaaagaagtaacacgtaataaatttattttatttagtgtgtatcaatc | GenBank Accession No: JQ627151.1 Plasmodium falciparum isolate |

| SEQ ID NO. | Sequence (5' to 3') | Comments |
|---|---|---|
| | gagtttctgacctatcagcttttgatgttagggtattggcctaacatggctatgacgggtaacg<br>gggaattagagttcgattccggagagggagcctgagaaatagctaccacatctaaggaag<br>gcagcaggcgcgtaaattacccaattctaaaaaagagaggtagtgacaagaaataacaatg<br>caaggccaattttttggttttgtaattggaatggtgggaatttaaaaccttcccagagtaacaatt<br>ggagggcaagtctggtgccagcagccgcggtaattccagctccaatagcgtatattaaaatt<br>gttgcagttaaaacgctcgtagttgaatttcaaagaatcgatattttattgtaactattctagggg<br>aactattttaggttttcgctttaatacgcttcctctattattatgttctttaaataacaaagattcttttt<br>aaaatccccacttttgcttttgctttttgggaatttgttactttgaataaattagaggtgtcaaag<br>caaacagttaaagcatttactgtgtttgaatactatagcatggaataacaaaattgaacaagct<br>aaaatttttgtcttttttcttattttggcttagttacgattaataggagtagcttggggacattcgt<br>attcagatgtcagaggtgaaattcttagattttctggagacgaacaactgcgaaagcatttgt<br>taaaatacttccattaatcaagaacgaaagttaagggagtgaagacgatcagataccgtcgta<br>atcttaaccataaactatgccgactaggtgttggatgaaagtgttaaaaataaaagtcatctttc<br>taggtgacttttagattgcttccttcagtacctatgagaaatcaaagtctttgggttctggggcg<br>agtattcgcgcaagcgagaaagttaaaagaattgacggaagggcaccaccaggcgtgga<br>gcttgcggcttaatttgactcaacacggggaaactcactagtttaagcaagagtaggattga<br>cagattaatagctattcttgatttcttggatggtgatgcatggccgttttagttcgtgaatatgat<br>ttgtctggttaattccgataacgaacgagatcttaacctgctaattagcggcgagtacactatat<br>tcttatttgaaattgaacataggtaactatacatttattcagtaatcaaattaggatatuttattaaa<br>atatccttttccctgttctactaataatttgttttttactctatttctctcttcttttaagaatgtacttgct<br>tgattgaaaagcttcttagaggaacattgtgtgtctaacacaaggaagtttaaggcaacaaca<br>ggtctgtgatgtccttagatgaactaggctgcacgcgtgctacactgatatatataacgagttt<br>taaaaat | SF3 18S ribosomal RNA gene, partial sequence |
| 75 | gaagtaggactttggttctatttt | Non-T7 primer |
| 76 | atgaagtaggactttggttct | Non-T7 primer |
| 77 | aacctggttgatcctgccagtagtcatatgcttgtcttaaagattaagccatgcatgtctaagta<br>caaacttttttacggtgaaactgcgaatggctcattacaacagttatagtttctttggtattcgtttt<br>ccatggataaccgtgctaattgtagggctaatacaagttcgaggccttttggcggcgtttatta<br>gttctataaccaccctttggttttcggtgattcataaaactcgcgaatcgcaattcatttattgcat<br>ggaccattcaagtttctgacccatcagcttgacggtagggtattggcctaccgaggcagcaa<br>cgggtaacggggaattagggttcgattccggagagggagcctgagaaacggctaccacat<br>ccaaggaaggcagcaggcgcgcaaattacccaatcctgacacagggaggtagtgacaag<br>aaataacaataacagggcaattgtcttgtaattggaatgatggtgacctaaaccctccaccagag<br>taacaattggagggcaagtctggtgccagcagccgcggtaattccagctccaatagcgtata<br>ttaaacttgttgcagttaaaaagctcgtagttgaatttctgcgttatcgagttattgactcttgtctt<br>taatcgatttcgcttttgggatttatcccttttttactttgagaaaattagagtgtttcaagcagacttt<br>tgtcttgaatacttcagcatggaataatagagtaggactttggttttgttggttttttgaacct<br>tagtaatggttaataggaacggttgggggcattcgtatttaactgtcagaggtgaaattcttag<br>atttgttaaagacgaactactgcgaaagcatttgccaaggacgtttccattaatcaagaacga<br>aagttaggggatcgaagacgatcagataccgtcgtagtcctaaccataaactatgccgacta<br>gggattggaggtcgcatttttccgactccttcagcaccttgagagaaatcaaagtctttgggtt<br>ctgggggagtatggtcgcaaggctgaaacttaaaggaattgacggaagggcaccacca<br>ggcgtggagcctgcggcttaatttgactcaacacggggaaactcaccaggtccagacaatg<br>ttaggattgacagattgatagctctttgattctttgggtggtggtgcatggccgttcttagttg<br>gtggagtgatttgtctggttaattccgttaacgaacgagaccttaacctgctaactagtacccg<br>taaaaaggttcgtccgttacggttttgcttcttagagggactttgcggctctaagccgcaagga<br>agtttaaggcaataacaggtctgtgatgcccttagatgtcctgggctgcacgcgcgctacact<br>gatgcattcatcgagtttaatcctgtcccgaaagggctgggtaatcttagtatgcatcgtgac<br>ggggattgattttttgcaattctaaatcatgaacgaggaatgcctagtatgcgcaagtcatcagc<br>ttgtgcagattacgtccctgccctttgtacacaccgcccgtcgctcctaccgatcgagtgatcc<br>ggtgaattattcggaccgtggcttttccgattcgtcggttttgcctagggaagtctcgtgaacct<br>tatcacttaaaggaaggagaagtcgtaacaaggtttccgtaggtgaacctgcagaaggatca<br>agc | GenBank Accession No: AY046575.1 Babesia sp. EU1 clone BAB20 18S ribosomal RNA gene, complete sequence |
| 78 | gyygccycggtaggccaauacccuaccguccaaagcugaur | |
| 79 | gyygccycggtaggccaatacccctaccgtccaaagctgatr | |
| 80 | aatttaatacgactcactatagggagaggcaaatgctttcgcagtagttngtctttaaca | T7 promoter primer, wherein "n" means a or g or c or t/u, or unknown, or other (WIPO Standard ST.25 (1998), Appendix 2, Table 1) |
| 81 | ggcaaatgctttcgcagtagttngtctttaaca | SEQ ID NO: 80 without promoter sequence, wherein "n" means a or g or c or t/u, or unknown, or other |

-continued

| SEQ ID NO. | Sequence (5' to 3') | Comments |
|---|---|---|
| | | (WIPO Standard ST.25 (1998), Appendix 2, Table 1) |
| 82 | aatttaatacgactcactatagggagaggcaaatgctttcgcagtagttigtctttaaca | T7 promoter primer. "i" means inosine. |
| 83 | ggcaaatgctttcgcagtagttigtctttaaca | SEQ ID NO: 82 without promoter sequence. "i" means inosine. |
| 84 | gcggtaattccagctccaatag | Non-T7 primer |
| 85 | cttgaatactncagca | Non-T7 primer, wherein "n" means a or g or c or t/u, or unknown, or other (WIPO Standard ST.25 (1998), Appendix 2, Table 1) |
| 86 | cttgaatacticagca | Non-T7 primer. "i" means inosine. |
| 87 | aaagacuuugauuucucucaagguuuaaaaaaaaaaaaaaaaaaaaaaaaaaaa | Target capture |
| 88 | aaagacuuugauuucucucaagg | SEQ ID NO: 87 without capture tail sequence |
| 89 | caagaaagagcuaucaaucugucaauccuuuaaaaaaaaaaaaaaaaaaaaaaaaaaaa | Target capture |
| 90 | caagaaagagcuaucaaucugucaaucc | SEQ ID NO: 89 without capture tail sequence |
| 91 | aguaggacuuugguuct | Probe |
| 92 | aguaggacuuugguuc | Probe |
| 93 | aguaggacuauugguuc | Probe |
| 94 | aguaggacxuugguuc | Probe, wherein "x" means (i) u; or (ii) ua |
| 95 | actttgagaaaaytagagtgtttcaaacaggccatttgccttgaatactncagcatggaataat gaagtaggactttggttctattttgttggtt | "n" means a or g or c or t/u, or unknown, or other (WIPO Standard ST.25 (1998), Appendix 2, Table 1) |
| 96 | ggcaaatgctttcgcagtagttngtctttaacaaatctaagaatttcacctctgacagttaaata cgaatgcccccaa | "n" means a or g or c or t/u, or unknown, or other (WIPO Standard ST.25 (1998), Appendix 2, Table 1) |
| 97 | ggcaaatgctttcgcagtagttngtctttaacaaatc | "n" means a or g or c or t/u, or unknown, or other (WIPO Standard ST.25 (1998), Appendix 2, Table 1) |
| 98 | aguaggacuauugguucu | Probe |

| SEQ ID NO. | Sequence (5' to 3') | Comments |
|---|---|---|
| 99 | aguaggacxuugguucu | Probe, wherein "x" means (i) u; or (ii) ua |
| 100 | GGGCGAAUUGGGUACCGGGCCCCCCCUCGAGGUCGAC GGUAUCGAUAAGCUUGAUAUCGAAUUCCUGCAGCCCG GGGGAUCCAACCUGGUUGAUCCUGCCAGUAGUCAUAU GCUUGUCUUAAAGAUUAAGCCAUGCAUGUCUAAGUAC AAACUUUUUACGGUGAAACUGCGAAUGGCUCAUUACA ACAGUUAUAGUUUCUUUGGUAUUCGUUUUCCAUGGA UAACCGUGCUAAUUGUAGGGCUAAUACAAGUUCGAG GCCUUUUGGCGGCGUUUAUUAGUUCUAUAACCACCCU UUUGGUUUUCGGUGAUUCAUAAUAAACUCGCGAAUC GCAAUUUAUUGCGAUGGACCAUUCAAGUUUCUGACCC AUCAGCUUGACGGUAGGGUAUUGGCCUACCGAGGCAG CAACGGGUAACGGGGAAUUAGGGUUCGAUUCCGGAG AGGGAGCCUGAGAAACGGCUACCACAUCCAAGGAAGG CAGCAGGCGCGCAAAUUACCCAAUCCUGACACAGGGA GGUAGUGACAAGAAAUAACAAUACAGGGCAAUUGUC UUGUAAUUGGAAUGAUGGUGACCUAAACCCUCACCAG AGUAACAAUUGGAGGGCAAGUCUGGUGCCAGCAGCCG CGGUAAUUCCAGCUCCAAUAGCGUAUAUUAAACUUGU UGCAGUUAAAAAGCUCGUAGUUGAAUUUCUGCGUUA UCGAGUUAUUGACUCUUGUCUUUAAUCGAUUUCGCUU UUGGGAUUUAUCCCUUUUUACUUUGAGAAAAUUAGA GUGUUUCAAGCAGACUUUUGUCUUGAAUACUUCAGCA UGGAAUAAUAGAGUAGGACUUUGGUUCUAUUUUGUU GGUUUUUGAACCUUAGUAAUGGUUAAUAGGAACGGU UGGGGGCAUUCGUAUUUAACUGUCAGAGGUGAAAUU CUUAGAUUUGUUAAAGACGAACUACUGCGAAAGCAU UUGCCAAGGACGUUUCCAUUAAUCAAGAACGAAAGUU AGGGGAUCGAAGACGAUCAGAUACCGUCGUAGUCCUA ACCAUAAACUAUGCCGACUAGGGAUUGGAGGUCGUCA UUUUUCCGACUCCUUCAGCACCUUGAGAGAAAUCAAA GUCUUUGGGUUCUGGGGGGAGUAUGGUCGCAAGGCU GAAACUUAAAGGAAUUGACGGAAGGGCACCACCAGGC GUGGAGCCUGCGGCUUAAUUUGACUCAACACGGGGAA ACUCACCAGGUCCAGACAAUGUUAGGAUUGACAGAUU GAUAGCUCUUUCUUGAUUCUUUGGGUGGUGCGGCC | *B. venatorum* IVT |
| 101 | ctttcgcagtagttng

```
SEQ ID NO: 3              moltype = DNA   length = 51
FEATURE                   Location/Qualifiers
misc_feature              1..51
                          note = Synthetic Oligonucleotide
regulatory                1..27
                          regulatory_class = promoter
source                    1..51
                          mol_type = other DNA
                          organism = synthetic construct
SEQUENCE: 3
aatttaatac gactcactat agggagaaca gttaaatacg aatgccccca a        51

SEQ ID NO: 4              moltype = DNA   length = 24
FEATURE                   Location/Qualifiers
misc_feature              1..24
                          note = Synthetic Oligonucleotide
source                    1..24
                          mol_type = other DNA
                          organism = synthetic construct
SEQUENCE: 4
acagttaaat acgaatgccc ccaa                                      24

SEQ ID NO: 5              moltype = DNA   length = 49
FEATURE                   Location/Qualifiers
misc_feature              1..49
                          note = Synthetic Oligonucleotide
regulatory                1..27
                          regulatory_class = promoter
source                    1..49
                          mol_type = other DNA
                          organism = synthetic construct
SEQUENCE: 5
aatttaatac gactcactat agggagattc acctctgaca gttaaatac           49

SEQ ID NO: 6              moltype = DNA   length = 22
FEATURE                   Location/Qualifiers
misc_feature              1..22
                          note = Synthetic Oligonucleotide
source                    1..22
                          mol_type = other DNA
                          organism = synthetic construct
SEQUENCE: 6
ttcacctctg acagttaaat ac                                        22

SEQ ID NO: 7              moltype = DNA   length = 57
FEATURE                   Location/Qualifiers
misc_feature              1..57
                          note = Synthetic Oligonucleotide
regulatory                1..27
                          regulatory_class = promoter
source                    1..57
                          mol_type = other DNA
                          organism = synthetic construct
SEQUENCE: 7
aatttaatac gactcactat agggagagct ttcgcagtag ttcgtcttta acaaatc  57

SEQ ID NO: 8              moltype = DNA   length = 30
FEATURE                   Location/Qualifiers
misc_feature              1..30
                          note = Synthetic Oligonucleotide
source                    1..30
                          mol_type = other DNA
                          organism = synthetic construct
SEQUENCE: 8
gctttcgcag tagttcgtct ttaacaaatc                                30

SEQ ID NO: 9              moltype = DNA   length = 51
FEATURE                   Location/Qualifiers
misc_feature              1..51
                          note = Synthetic Oligonucleotide
source                    1..51
                          mol_type = other DNA
                          organism = synthetic construct
SEQUENCE: 9
aatttaatac gactcactat agggagactt tcgcagtagt tcgtctttaa c        51

SEQ ID NO: 10             moltype = DNA   length = 24
FEATURE                   Location/Qualifiers
```

```
misc_feature      1..24
                  note = Synthetic Oligonucleotide
source            1..24
                  mol_type = other DNA
                  organism = synthetic construct
SEQUENCE: 10
ctttcgcagt agttcgtctt taac                                              24

SEQ ID NO: 11     moltype = DNA   length = 20
FEATURE           Location/Qualifiers
misc_feature      1..20
                  note = Synthetic Oligonucleotide
source            1..20
                  mol_type = other DNA
                  organism = synthetic construct
SEQUENCE: 11
cttgaatact acagcatgga                                                   20

SEQ ID NO: 12     moltype = DNA   length = 20
FEATURE           Location/Qualifiers
misc_feature      1..20
                  note = Synthetic Oligonucleotide
source            1..20
                  mol_type = other DNA
                  organism = synthetic construct
SEQUENCE: 12
actacagcat ggaataatga                                                   20

SEQ ID NO: 13     moltype = DNA   length = 24
FEATURE           Location/Qualifiers
misc_feature      1..24
                  note = Synthetic Oligonucleotide
source            1..24
                  mol_type = other DNA
                  organism = synthetic construct
SEQUENCE: 13
cttgaatact acagcatgga ataa                                              24

SEQ ID NO: 14     moltype = DNA   length = 20
FEATURE           Location/Qualifiers
misc_feature      1..20
                  note = Synthetic Oligonucleotide
source            1..20
                  mol_type = other DNA
                  organism = synthetic construct
SEQUENCE: 14
acttcagcat ggaataatga                                                   20

SEQ ID NO: 15     moltype = DNA   length = 20
FEATURE           Location/Qualifiers
misc_feature      1..20
                  note = Synthetic Oligonucleotide
source            1..20
                  mol_type = other DNA
                  organism = synthetic construct
SEQUENCE: 15
cttgaatact tcagcatgga                                                   20

SEQ ID NO: 16     moltype = DNA   length = 20
FEATURE           Location/Qualifiers
misc_feature      1..20
                  note = Synthetic Oligonucleotide
variation         4
                  note = "n" means a or g or c or t/u, or unknown, or other
                   (WIPO StandardST.25 (1998), Appendix 2, Table 1)
misc_difference   4
                  note = n is a, c, g, or t
source            1..20
                  mol_type = other DNA
                  organism = synthetic construct
SEQUENCE: 16
actncagcat ggaataatga                                                   20

SEQ ID NO: 17     moltype = DNA   length = 20
FEATURE           Location/Qualifiers
misc_feature      1..20
                  note = Synthetic Oligonucleotide
source            1..20
                  mol_type = other DNA
```

```
                       organism = synthetic construct
SEQUENCE: 17
actwcagcat ggaataatga                                                    20

SEQ ID NO: 18          moltype = DNA  length = 20
FEATURE                Location/Qualifiers
misc_feature           1..20
                       note = Synthetic Oligonucleotide
variation              11
                       note = "n" means a or g or c or t/u, or unknown, or other
                        (WIPO StandardST.25 (1998), Appendix 2, Table 1)
misc_feature           11
                       note = n is a, c, g, or t
source                 1..20
                       mol_type = other DNA
                       organism = synthetic construct
SEQUENCE: 18
cttgaatact ncagcatgga                                                    20

SEQ ID NO: 19          moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 19
cttgaatact wcagcatgga                                                    20

SEQ ID NO: 20          moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 20
actttgagaa aactagagtg                                                    20

SEQ ID NO: 21          moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 21
agaaaactag agtgtttcaa                                                    20

SEQ ID NO: 22          moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 22
ataatgaagt aggactttgg                                                    20

SEQ ID NO: 23          moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 23
aggactttgg ttctatttttg                                                   20

SEQ ID NO: 24          moltype = DNA  length = 18
FEATURE                Location/Qualifiers
misc_feature           1..18
                       note = Synthetic Oligonucleotide
source                 1..18
                       mol_type = other DNA
                       organism = synthetic construct
SEQUENCE: 24
ggttctattt tgttggtt                                                      18
```

```
SEQ ID NO: 25          moltype = DNA   length = 17
FEATURE                Location/Qualifiers
misc_feature           1..17
                       note = Synthetic Oligonucleotide
source                 1..17
                       mol_type = other DNA
                       organism = synthetic construct
SEQUENCE: 25
tggttctatt ttgttgg                                                    17

SEQ ID NO: 26          moltype = DNA   length = 21
FEATURE                Location/Qualifiers
misc_feature           1..21
                       note = Synthetic Oligonucleotide
source                 1..21
                       mol_type = other DNA
                       organism = synthetic construct
SEQUENCE: 26
ggaataatga agtaggactt t                                               21

SEQ ID NO: 27          moltype = DNA   length = 20
FEATURE                Location/Qualifiers
misc_feature           1..20
                       note = Synthetic Oligonucleotide
source                 1..20
                       mol_type = other DNA
                       organism = synthetic construct
SEQUENCE: 27
atggaataat gaagtaggac                                                 20

SEQ ID NO: 28          moltype = DNA   length = 18
FEATURE                Location/Qualifiers
misc_feature           1..18
                       note = Synthetic Oligonucleotide
source                 1..18
                       mol_type = other DNA
                       organism = synthetic construct
SEQUENCE: 28
atggaataat gaagtagg                                                   18

SEQ ID NO: 29          moltype = DNA   length = 19
FEATURE                Location/Qualifiers
misc_feature           1..19
                       note = Synthetic Oligonucleotide
source                 1..19
                       mol_type = other DNA
                       organism = synthetic construct
SEQUENCE: 29
gcatggaata atgaagtag                                                  19

SEQ ID NO: 30          moltype = DNA   length = 20
FEATURE                Location/Qualifiers
misc_feature           1..20
                       note = Synthetic Oligonucleotide
source                 1..20
                       mol_type = other DNA
                       organism = synthetic construct
SEQUENCE: 30
tacagcatgg aataatgaag                                                 20

SEQ ID NO: 31          moltype = DNA   length = 20
FEATURE                Location/Qualifiers
misc_feature           1..20
                       note = Synthetic Oligonucleotide
source                 1..20
                       mol_type = other DNA
                       organism = synthetic construct
SEQUENCE: 31
tactacagca tggaataatg                                                 20

SEQ ID NO: 32          moltype = DNA   length = 19
FEATURE                Location/Qualifiers
misc_feature           1..19
                       note = Synthetic Oligonucleotide
source                 1..19
                       mol_type = other DNA
                       organism = synthetic construct
SEQUENCE: 32
agaaaactag agtgtttca                                                  19
```

```
SEQ ID NO: 33           moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 33
agaaaattag agtgtttcaa                                               20

SEQ ID NO: 34           moltype = DNA  length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 34
gagaaaacta gagtgtttca a                                             21

SEQ ID NO: 35           moltype = DNA  length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 35
gagaaaatta gagtgtttca a                                             21

SEQ ID NO: 36           moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 36
tgagaaaact agagtgtttc                                               20

SEQ ID NO: 37           moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 37
tgaagtagga ctttggttct                                               20

SEQ ID NO: 38           moltype = DNA  length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 38
taatggttaa taggagcagt tg                                            22

SEQ ID NO: 39           moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 39
agtaatggtt aataggagca                                               20

SEQ ID NO: 40           moltype = DNA  length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 40
```

```
ggactttggt tctattttgt tgg                                         23

SEQ ID NO: 41          moltype = DNA   length = 25
FEATURE                Location/Qualifiers
misc_feature           1..25
                       note = Synthetic Oligonucleotide
source                 1..25
                       mol_type = other DNA
                       organism = synthetic construct
SEQUENCE: 41
aatggttaat aggagcagtt ggggg                                       25

SEQ ID NO: 42          moltype = DNA   length = 17
FEATURE                Location/Qualifiers
misc_feature           1..17
                       note = Synthetic Oligonucleotide
source                 1..17
                       mol_type = other DNA
                       organism = synthetic construct
SEQUENCE: 42
agtaggactt tggttct                                                17

SEQ ID NO: 43          moltype = DNA   length = 54
FEATURE                Location/Qualifiers
misc_feature           1..54
                       note = Synthetic Oligonucleotide
misc_feature           22..54
                       note = capture sequence
source                 1..54
                       mol_type = other DNA
                       organism = synthetic construct
SEQUENCE: 43
taggccaata ccctaccgtc ctttaaaaaa aaaaaaaaaa aaaaaaaaaa aaaa        54

SEQ ID NO: 44          moltype = DNA   length = 21
FEATURE                Location/Qualifiers
misc_feature           1..21
                       note = Synthetic Oligonucleotide
source                 1..21
                       mol_type = other DNA
                       organism = synthetic construct
SEQUENCE: 44
taggccaata ccctaccgtc c                                           21

SEQ ID NO: 45          moltype = DNA   length = 17
FEATURE                Location/Qualifiers
misc_feature           1..17
                       note = Synthetic Oligonucleotide
source                 1..17
                       mol_type = other DNA
                       organism = synthetic construct
SEQUENCE: 45
atggaataat gaagtag                                                17

SEQ ID NO: 46          moltype = DNA   length = 14
FEATURE                Location/Qualifiers
misc_feature           1..14
                       note = Synthetic Oligonucleotide
source                 1..14
                       mol_type = other DNA
                       organism = synthetic construct
SEQUENCE: 46
agaaaactag agtg                                                   14

SEQ ID NO: 47          moltype = DNA   length = 14
FEATURE                Location/Qualifiers
misc_feature           1..14
                       note = Synthetic Oligonucleotide
source                 1..14
                       mol_type = other DNA
                       organism = synthetic construct
SEQUENCE: 47
agaaaattag agtg                                                   14

SEQ ID NO: 48          moltype = DNA   length = 14
FEATURE                Location/Qualifiers
misc_feature           1..14
                       note = Synthetic Oligonucleotide
source                 1..14
```

```
                    mol_type = other DNA
                    organism = synthetic construct
SEQUENCE: 48
agaaaaytag agtg                                                         14

SEQ ID NO: 49       moltype = DNA   length = 18
FEATURE             Location/Qualifiers
misc_feature        1..18
                    note = Synthetic Oligonucleotide
source              1..18
                    mol_type = other DNA
                    organism = synthetic construct
SEQUENCE: 49
agaaaactag agtgtttc                                                     18

SEQ ID NO: 50       moltype = DNA   length = 18
FEATURE             Location/Qualifiers
misc_feature        1..18
                    note = Synthetic Oligonucleotide
source              1..18
                    mol_type = other DNA
                    organism = synthetic construct
SEQUENCE: 50
agaaaattag agtgtttc                                                     18

SEQ ID NO: 51       moltype = DNA   length = 18
FEATURE             Location/Qualifiers
misc_feature        1..18
                    note = Synthetic Oligonucleotide
source              1..18
                    mol_type = other DNA
                    organism = synthetic construct
SEQUENCE: 51
agaaaaytag agtgtttc                                                     18

SEQ ID NO: 52       moltype = DNA   length = 18
FEATURE             Location/Qualifiers
misc_feature        1..18
                    note = Synthetic Oligonucleotide
source              1..18
                    mol_type = other DNA
                    organism = synthetic construct
SEQUENCE: 52
tactacagca tggaataa                                                     18

SEQ ID NO: 53       moltype = DNA   length = 13
FEATURE             Location/Qualifiers
misc_feature        1..13
                    note = Synthetic Oligonucleotide
variation           4
                    note = "n" means a or g or c or t/u, or unknown, or other
                    (WIPO StandardST.25 (1998), Appendix 2, Table 1)
misc_difference     4
                    note = n is a, c, g, or t
source              1..13
                    mol_type = other DNA
                    organism = synthetic construct
SEQUENCE: 53
actncagcat gga                                                          13

SEQ ID NO: 54       moltype = DNA   length = 13
FEATURE             Location/Qualifiers
misc_feature        1..13
                    note = Synthetic Oligonucleotide
source              1..13
                    mol_type = other DNA
                    organism = synthetic construct
SEQUENCE: 54
actwcagcat gga                                                          13

SEQ ID NO: 55       moltype = DNA   length = 13
FEATURE             Location/Qualifiers
misc_feature        1..13
                    note = Synthetic Oligonucleotide
source              1..13
                    mol_type = other DNA
                    organism = synthetic construct
SEQUENCE: 55
actacagcat gga                                                          13
```

```
SEQ ID NO: 56           moltype = DNA  length = 12
FEATURE                 Location/Qualifiers
misc_feature            1..12
                        note = Synthetic Oligonucleotide
source                  1..12
                        mol_type = other DNA
                        organism = synthetic construct
SEQUENCE: 56
gtatttaact gt                                                       12

SEQ ID NO: 57           moltype = DNA  length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 57
gtatttaact gtcagaggtg aa                                            22

SEQ ID NO: 58           moltype = DNA  length = 27
FEATURE                 Location/Qualifiers
misc_feature            1..27
                        note = Synthetic Oligonucleotide
source                  1..27
                        mol_type = other DNA
                        organism = synthetic construct
SEQUENCE: 58
aatttaatac gactcactat agggaga                                       27

SEQ ID NO: 59           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 59
agtaggactt tggttct                                                  17

SEQ ID NO: 60           moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 60
taatggttaa taggagca                                                 18

SEQ ID NO: 61           moltype = DNA  length = 1206
FEATURE                 Location/Qualifiers
misc_feature            1..1206
                        note = B. microti In Vitro Transcript
source                  1..1206
                        mol_type = other DNA
                        organism = synthetic construct
SEQUENCE: 61
gggcgaattg ggtaccgggc ccccccctcga ggtcgacgct tagtataagc ttttatacag  60
cgaaactgcg aatggctcat taaaacagtt atagtttatt tgatgttcgt tttacatgga  120
taaccgtggt aattctaggg ctaatacatg ctcgaggcgc gttttcgcgt ggcgtttatt  180
agactttaac caacccttcg ggtaatcggt gattcataat aaattagcga atcgcatggc  240
tttgccggcg atgtatcatt caagtttctg acctatcagc tttggacggt agggtattgg  300
cctaccgggg cgacgacggg tgacggggaa ttggggttcg attccggaga gggagcctga  360
gaaacggcta ccacatctaa ggaaggcagc aggcgcgcaa attacccaat cctgacacag  420
ggaggtagtg acaagaaata acaatacagg gcttaaagtc ttgtaattgg aatgatggga  480
atctaaaccc ttcccagagt atcaattgga gggcaagtct ggtgccagca gccgcggtaa  540
ttccagctcc aatagcgtat attaaagttg ttgcagttaa gaagctcgta gttgaatttc  600
tgccttgtca ttaatctcgc ttccgagcgt ttttttattg acttggcatc ttctggattt  660
ggtgccttcg ggtactattt tccaggattt actttgagaa aactagagtg tttcaaacag  720
gcattcgcct tgaatactac agcatggaat aatgaagtag gactttggtt ctattttgtt  780
ggttattgag ccagagtaat ggttaatagg agcagttggg ggcattcgta tttaactgtc  840
agaggtgaaa ttcttagatt tgttaaagac gaactactgc gaaagcattt gccaaggatg  900
ttttcattaa tcaagaacga aagttagggg atcgaagacg atcagatacc gtcgtagtcc  960
taaccataaa ctatgccgac tagagattgg aggtcgtcag tttaaacgac tccttcagca  1020
ccttgagaga aatcaaagtc tttgggttct gggggagta tggtcgcaag tctgaaactt  1080
aaaggaattg acggaagggc accaccaggc gtggagcctg cggcttaatt tgactcaaca  1140
cgggaaacct caccaggtcc agacatagag aggattgaca gattgatagc tctttcttga  1200

```
tgaatt                                                                  1206

SEQ ID NO: 62           moltype = DNA  length = 1282
FEATURE                 Location/Qualifiers
misc_feature            1..1282
                        note = B. divergens In Vitro Transcript
source                  1..1282
                        mol_type = other DNA
                        organism = synthetic construct
SEQUENCE: 62
gggcgaattg ggtaccgggc cccccctcga ggtcgacggt atcgataagc ttgatatcga        60
attcctgcag cccggggat  ccaacctggt tgatcctgcc agtagtcata tgcttgtctt       120
aaagattaag ccatgcatgt ctaagtacaa acttttacg  gtgaaactgc gaatggctca       180
ttacaacagt tatagtttct tggtattcg  ttttccatgg ataaccgtgc taattgtagg       240
gctaatacaa gttcgaggcc ttttggcggc gtttattagt tctaaaacca tccccttttgg     300
ttttcggtga ttcataataa acttgcgaat cgcaattttt tgcgatggac cattcaagtt      360
tctgacccat cagcttgacg gtagggtatt ggcctaccga ggcagcaacg ggtaacgggg      420
aatttagggtt cgattccgga gagggagcct gagaaacggc taccacatcc aaggaaggca     480
gcaggcgcgc aaattcccca atcctgacac agggaggtag tgacaagaaa taacaataca     540
gggcaattgt cttgtaattg gaatgatggt gacctaaacc ctcaccagag taacaattgg      600
agggcaagtc tggtgccagc agccgcgta  attccagctc caatagcgta tattaaactt      660
gttgcagtta aaaagctcgt agttgaattt ttgcgtggtg ttaatattga ctaatgtcga      720
gattgcactt cgcttttggg atttatccct ttttactttg agaaaattag agtgtttcaa      780
gcagactttt gtcttgaata cttcagcatg gaataataga gtaggacttt ggttctattt     840
tgttggtttg tgaaccttag taatggttaa taggaacggt tgggggcatt cgtatttaac     900
tgtcagaggt gaaattctta gatttgttaa agacgaacta ctgcgaaagc atttgccaag     960
gacgttttca ttaatcaaga acgaaagtta ggggatcgaa gacgatcaga taccgtcgta    1020
gtcctaacca taaactatgc cgactaggga ttggaggtcg tcattttcc  gactccttca    1080
gcaccttgag agaaatcaaa gtctttggt  tctgggggga gtatggtcgc aaggctgaaa    1140
cttaaaggaa ttgacggaag gcaccacca  ggcgtgagc  ctgcggctta atttgactca    1200
acacggggaa actcaccagg tccagacaat gttaggatt  acagattgat agctctttct    1260
tgattctttg ggtggtgcgg cc                                              1282

SEQ ID NO: 63           moltype = DNA  length = 1251
FEATURE                 Location/Qualifiers
misc_feature            1..1251
                        note = B. duncani In Vitro Transcript
source                  1..1251
                        mol_type = other DNA
                        organism = synthetic construct
SEQUENCE: 63
gggcgaattg ggtaccgggc cccccctcga ggtcgacgtt gatcctgcca gtagtcatat        60
gcttgtctta aagattaagc catgcatgtc taagtataaa cttttatatg gtgaaactgc       120
gaatggctca ttacaacagt tatagtttat ttgaaagtcg tttttacatg gataaccgtg      180
ctaattgtag ggctaataca tgctcgaggc cttggctcct gtcttggctg cgttattag       240
actcgaaacc ttcccgcttg cggtactcgg tgattcataa taaatttgcg aatcgcatgg     300
cttttgccgg cgatggttca ttcaagtttc tgacctatgc cctttggacg gtagggtatt     360
ggcctaccgg ggcagcgacg ggtaacgggg aattagggtt cgattccgga gagggagcct    420
gagaaacggc taccacatct aaggaaggca gcaggcgcgc aaattcccca atacggacac    480
cgtgaggtag tgacaagaaa taacaataca gggcttaaag ctttgtaatt ggaatgatgg    540
gaatccaaac cccttccaga gtatcaattg gagggccag  ctggtgccag cagccgcggt    600
aattccagct ccaatagcgt atattaaact tgttgcagtt aaaaagctcg tagttgaact     660
tctgccgctt ggccttttcgt tcccccttgg gttttcgttcg cctggtgggct tacctctggc    720
ggtggttctc catttgccag ttttactttg agaaaattag agtgtttcaa gcaggctttt      780
gccttgaata cttcagcatg gaataataaa gtaggactt  ggttctattt tgttggtttc      840
aggaccaaag taatggttaa taggaacagt tgggggcatt cgtatttaac tgtcagaggt     900
gaaattctta gatttgttaa agacgaacta ctgcgaaagc atttgccaag gatgttttca     960
ttaatcaaga acgaaagtta ggggctcgaa gacgatcaga taccgtcgta gtcctaacta    1020
taaactatgc cgactagaga ttggaggtcg tcattttaaa cgactccttc agcaccttga    1080
gagaaatcaa agtctttggg ttctgggggg agtatggtcg caaggctgaa acttaaagga    1140
attgacggaa gggcaccacc aggcgtggag cctgcggctt aatttgactc aacacgggga    1200
acctcaccag gtccagacat agttaggatt gacagattga tagctcgaat t              1251

SEQ ID NO: 64           moltype = DNA  length = 1387
FEATURE                 Location/Qualifiers
misc_feature            1..1387
                        note = P. falciparum In Vitro Transcript
source                  1..1387
                        mol_type = other DNA
                        organism = synthetic construct
SEQUENCE: 64
gggcgaattg ggtaccgtag aaactgcgaa cggctcatta aaacagttat agtctacttg        60
acattttttat tataaggata actacggaaa agctgtagct aatacttgct ttattatcct     120
ttgattttta tctttggata agtattttgtt aggccttata agaaaaaagt tattaactta    180
aggaattata acaaagaagt aacacgtaat aaatttattt tatttagtgt gtatcaatcg      240
agtttctgac ctatcagctt ttgatgttag ggtattggcc taacatggct atgacgggta    300
acggggaatt agagttcgat tccgagagg  gagcctgaga aatagctacc acatctaagg    360
aaggcagcag gcgcgtaaat tacccaattc taaaaaagag aggtagtgac aagaaataac    420
aatgcaaggc caattttttgg ttttgtaatt ggaatggtgg gaatttaaaa ccttcccaga    480
```

```
gtaacaattg gagggcaagt ctggtgccag cagccgcggt aattccagct ccaatagcgt   540
atattaaaat tgttgcagtt aaaacgctcg tagttgaatt tcaaagaatc gatattttat   600
tgtaactatt ctaggggaac tatttttaggt tttcgcttta atacgcttcc tctattatta   660
tgttctttaa ataacaaaga ttcttttaa atccccact tttgctttt tggggaatt     720
gttactttga ataaattaga ggtgtcaaag caaacagtta aagcatttac tgtgtttgaa   780
tactatagca tggaataaca aaattgaaca agctaaaatt ttttgttctt ttttcttatt   840
ttggcttagt tacgattaat aggagtagct tggggacatt cgtattcaga tgtcagaggt   900
gaaattctta gattttctgg agacgaacaa ctgcgaaagc atttgtctaa aatacttcca   960
ttaatcaaga acgaaagtta agggagtgaa gacgatcaga taccgtcgta atcttaacca  1020
taaactatgc cgactaggtg ttggatgaaa gtgttaaaaa taaaagtcat ctttctaggt  1080
gactttttaga ttgcttcctt cagtaccttta tgagaaatca aagtctttgg gttctggggc  1140
gagtattcgc gcaagcgaga aagttaaaag aattgacgga agggcaccac caggcgtgga  1200
gcttgcggct taatttgact caacacgggg aaactcacta gttaagaca agagtaggat  1260
tgacagatta atagctcttt cttgatttct tggatggtga tgcatggccg tttttagttc  1320
gtgaatatga tttgtctggt taattccgat aacgaacgag atcggatcca ctagtctag   1380
agcggcc                                                           1387

SEQ ID NO: 65            moltype = DNA  length = 70
FEATURE                  Location/Qualifiers
misc_feature             1..70
                         note = Synthetic Oligonucleotide
source                   1..70
                         mol_type = other DNA
                         organism = synthetic construct
SEQUENCE: 65
tgaagtagga ctttggttct attttgttgg ttattgagcc agagtaatgg ttaataggag   60
cagttggggg                                                         70

SEQ ID NO: 66            moltype = DNA  length = 34
FEATURE                  Location/Qualifiers
misc_feature             1..34
                         note = Synthetic Oligonucleotide
source                   1..34
                         mol_type = other DNA
                         organism = synthetic construct
SEQUENCE: 66
ttcacctctg acagttaaat acgaatgccc ccaa                               34

SEQ ID NO: 67            moltype = DNA  length = 34
FEATURE                  Location/Qualifiers
misc_feature             1..34
                         note = Synthetic Oligonucleotide
variation                5
                         note = "n" means a or g or c or t/u, or unknown, or other
                           (WIPO StandardST.25 (1998), Appendix 2, Table 1)
misc_difference          5
                         note = n is a, c, g, or t
source                   1..34
                         mol_type = other DNA
                         organism = synthetic construct
SEQUENCE: 67
tactncagca tggaataatg aagtaggact tgg                                34

SEQ ID NO: 68            moltype = DNA  length = 27
FEATURE                  Location/Qualifiers
misc_feature             1..27
                         note = Synthetic Oligonucleotide
variation                11
                         note = "n" means a or g or c or t/u, or unknown, or other
                           (WIPO StandardST.25 (1998), Appendix 2, Table 1)
misc_feature             11
                         note = n is a, c, g, or t
source                   1..27
                         mol_type = other DNA
                         organism = synthetic construct
SEQUENCE: 68
cttgaatact ncagcatgga ataatga                                       27

SEQ ID NO: 69            moltype = DNA  length = 11
FEATURE                  Location/Qualifiers
misc_feature             1..11
                         note = Synthetic Oligonucleotide
source                   1..11
                         mol_type = other DNA
                         organism = synthetic construct
SEQUENCE: 69
atggaataat g                                                        11

SEQ ID NO: 70            moltype = DNA  length = 27
```

| FEATURE | Location/Qualifiers |
|---|---|
| misc_feature | 1..27 |
| | note = Synthetic Oligonucleotide |
| source | 1..27 |
| | mol_type = other DNA |
| | organism = synthetic construct |

SEQUENCE: 70

```
actttgagaa aaytagagtg tttcaaa                                         27
```

| SEQ ID NO: 71 | moltype = DNA  length = 1767 |
|---|---|
| FEATURE | Location/Qualifiers |
| source | 1..1767 |
| | mol_type = genomic DNA |
| | organism = Babesia microti |

SEQUENCE: 71

```
aacctggttg atcctgccag tagtcatatg cttgtcttaa agattaagcc atgcatgtct     60
tagtataagc ttttatacag cgaaactgcg aatggctcat taaaacagtt atagtttatt    120
tgatgttcgt tttacatgga taaccgtggt aattctaggg ctaatacatg ctcgaggcgc    180
gttttcgcgt ggcgtttatt agactttaac caacccttcg ggtaatcggt gattcataat    240
aaattagcga atcgcatggc tttgccggcg atgtatcatt caagtttctg acctatcagc    300
tttggacggt agggtattgg cctaccgggg cgacgacggg tgacgggaa ttggggttcg     360
attccggaga gggagcctga gaaacggcta ccacatccaa ggcgcgcgaa aggcgcgcaa    420
attacccaat cctgacacag ggaggtagtg acaagaaata acaatacagg cttaaagtc     480
ttgtaattgg aatgatggga atctaaaccc ttcccagagt atcaattgga gggcaagtct    540
ggtgccagca gccgcggtaa ttccagctcc aatagcgtat attaaagttg ttgcagttaa    600
gaagctcgta gttgaatttc tgccttgtca ttaatctcgc ttccgagcgt tttttattg    660
acttggcatc ttctggattt ggtgccttcg ggtactattt ccaggattt acttgagaa     720
aactagagtg tttcaaacag gcattcgcct tgaatactac agcatggaat aatgaagtag    780
gactttggtt ctattttgtt ggttattgag ccagagtaat ggttaatagg agcagttggg    840
ggcattcgta tttaactgtc agaggtgaaa ttccttagatt tgttaaagac gaactactgc   900
gaaagcattt gccaaggatg ttttcattaa tcaagaacga agttagggg atcgaagacg     960
atcagatacc gtcgtagtcc taaccataaa ctatgccgac tagagattgg aggtcgtcag   1020
tttaaacgac tccttcagca ccttgagaga atcaaagtc tttggggtct ggggggagta    1080
tggtcgcaag tctgaaactt aaaggaattg acggaagggc accaccaggc gtggagcctg   1140
cggcttaatt tgactcaaca cgggaaacct caccaggtcc agacatagag aggattgaca   1200
gattgatagc tctttcttga ttctatgggt ggtggtgcat ggccgttctt agttggtgga   1260
gtgatttgtc tggttaattc cgttaacgaa cgagacctta acctgctaaa ttaggatctg   1320
ggacaagctt tgctgttcca gtatcgcttc ttagagggac tttgcgttca taaaacgcaa   1380
ggaagtgtaa ggcaataaca ggtctgtgat gcccttagat gtcctgggct gcacgcgcaa   1440
tacactgatg cattcaacga gtttttcctt ggccgtcggg tccgggtaat cttacagtat   1500
gcatcgtgat gggatagat tattgcaatt attaatcttg aacgaggaat gcctagtagg    1560
cgcgagtcat cagctcgtgc cgactacgtc cctgcccttt gtacacaccg cccgtcgctc   1620
ctaccgatcg agtgatccgg tgaattattc ggaccaagaa acgtgcgttc gtccttcgtt   1680
ttttggaaag ttttgtgaac cttatcactt aaaggaagga gaagtcgtaa caaggtttcc   1740
gtaggtgaac ctgcggaagg atcattc                                       1767
```

| SEQ ID NO: 72 | moltype = DNA  length = 1728 |
|---|---|
| FEATURE | Location/Qualifiers |
| source | 1..1728 |
| | mol_type = genomic DNA |
| | organism = Babesia divergens |

SEQUENCE: 72

```
aacctggttg atcctgccag tagtcatatg cttgtcttaa agattaagcc atgcatgtct     60
aagtacaaac ttttttacggt gaaactgcga atggctcatt acaacagtta tagttctctt   120
ggtattcgtt ttcatggat aaccgtgcta atttgtaggg taatacaagt tcgaggcctt    180
ttggcggcgt ttattagttc taaaaccatc cctttggtt ttcggtgatt cataataaac    240
ttgcgaatcg caattttttg cgatggacca ttcaagtttc tgaccatca gcttgacggt     300
agggtattgg cctaccgagg cagcaacggg taacggggaa ttagggttcg attccggaga    360
gggagcctga gaaacggcta ccacatccaa ggaaggcagc aggcgcgcaa attacccaat    420
cctgacacag ggaggtagtg acaagaaata acaatacagg gcaattgtct tgtaattgaa    480
atgatggtga cctaaaccct caccagagta acaattggag gcaagtctg gtgccagcag    540
ccgcggtaat tccagctcca atagcgtata ttaaacttgt tgcagttaaa aagctcgtag    600
ttgaattttt gcgtggtgtt aatattgact aatgtcgaga ttgcacttcg cttttgggat    660
ttatcccttt ttactttgag aaaattagag tgtttcagaa agactttttgt cttgaatact    720
tcagcatgga ataatagagt aggacttgg ttctattttg tggtttgtg aaccttagta     780
atggttaata ggaacggttg ggggcattcg tatttaactg tcagaggtga aattcttaga    840
tttgttaaag acgaactact gcgaaagcat tgccaagga cgttttcatt aatcaagaac    900
gaaagttagg ggatcgaaga cgatcagata ccgtcgtagt cctaaccata aactatgccg    960
actagggatt ggaggtcgtc atttttccga ctccttcaga acctggatgag aaatcaaagt   1020
ctttgggttc tggggggagt atggtcgcaa ggctgaaact taaaggaatt gacggaaggg   1080
caccaccagg cgtgggagcct gcggcttaat ttgactcaac acgggaaac tcaccaggtc   1140
cagacaatgt taggattgac agattgatag ctctttcttg attctttggg tggtggtgca   1200
tggccgttct tagttggtgg agtgatttgt ctggttaatt ccgttaacga acgagacctt   1260
aacctgctaa ctagtgtccg taaaaaggtt cgtccgttac ggtttgcttc ttagagggac   1320
tttgcggctc taagccgcaa ggaagtttaa ggcaataaca ggtctgtgat gcccttagat   1380
gtcctgggct gcacgcgcgc tacactgatg cattcatcga gttttatccc ttcccgaaag   1440
ggctgggtaa tcttttagtat gcatcgtgac ggggattgat ttttgcaatt ctaaatcatg   1500
aacgaggaat gcctagtatg cgcaagtcat cagcttgtgc agattacgtc cctgcccttt   1560
gtacacaccg cccgtcgctc ctaccgatcg agtgatccgg tgaattattc ggaccgtggc   1620
```

```
ctttccgatt cgtcggcttg gcctagggaa gtcttgtgaa ccttatcact taaaggaagg   1680
agaagtcgta acaaggtttc cgtaggtgaa cctgcggaag gatcattc                1728

SEQ ID NO: 73           moltype = DNA   length = 1742
FEATURE                 Location/Qualifiers
source                  1..1742
                        mol_type = genomic DNA
                        organism = Babesia sp.
                        strain = WA1
SEQUENCE: 73
ccttggttga tcctgccagt agtcatatgc ttgtcttaag gattaagcca tgcatgtcta    60
agtataaact tttatatggt gaaactgcga atggctcatt acaacagtta tagtttattt   120
gaaagtcgtt tttacatgga taaccgtgct aattgtaggg ctaatacatg ctcgaggcct   180
tggcttctgt cttggctgcg tttattagac tcgaaacctt cccgcttgcg gtactcggtg   240
attcataata aatttgcgaa tcgcatggct tttgccggcg atggttcatt caagtttctg   300
acctatcagc tttggacggt agggtattgg cctaccgggg cagcgacggg taacggggaa   360
ttagggttcg attccggaga gggagcctga gaaacggcta ccacatctaa ggaaggcagc   420
aggcgcgcaa attacccaat acggacaccg tgaggtagtg acaagaaata acaatacagg   480
gctttaagct ttgtaattgg aatgatggga atccaaaccc cttccagagt atcaattgga   540
gggcaagtct ggtgccagca gccgcggtaa ttccagctcc aatagcgtat attaaacttg   600
ttgcagttaa aaagctcgta gttgaacttc tgccgcttgg cctttcgttc cccttggggt   660
ttcgttcgcc tggtggctta cctctggcgg tggttctcca ttactttgag                720
aaaattagag tgtttcaagc aggctttgc cttgaatact tcagcatgga ataataaagt   780
aggactttgg ttctattttg ttggtttcag gaccaaagta atggttaata ggaacagttg   840
ggggcattcg tatttaactg tcagaggtga aattcttaga tttgttaaag acgaactact   900
gcgaaaagcat ttgccaagga tgttttcatt aatcaagaac gaaagttagg ggctcgaaga   960
cgatcagata ccgtcgtagt cctaactata aactatgccg actagagatt ggaggtcgtc  1020
attttaaacg actccttcag cacctggaga gaaatcaaag tctttgggtt ctgggggag   1080
tatggtcgca aggctgaaac ttaaaggaat tgacggaagg gcaccaccag gcgtggagcc  1140
tgcggcttaa tttgactcaa cacggggaac ctcaccagat ccagacatag ttaggattga  1200
cagattgata gctctttctt gattctatgg gtagtggtgc atggccgttc ttagttggtg  1260
gagtgatttg tctggttaat tccgttaacg aacgagaccct taacctgcta aatagcagct  1320
gagaataatc tcttgtttca gttttgcttc ttagagggac tttgcggtca taaatcgcaa  1380
ggaagtttaa ggcaataaca ggtctgtgat gcccttagat gtcctgggct gcacgcgcgc  1440
tacactgatg cattcatcga gttttatcct tgcccgaaag ggtttggtaa tctttagtat  1500
gcatcgtgat gggggattgat tattgcaatt attaatcatg aacgaggaat gcctagtagg  1560
cgcgagtcat cagctcgtgc cgactacgtc cctgcccttt gtacacaccg cccgtcgctc  1620
ctaccgatcg agtgatccgg tgaattattc ggaccgtgac gcttctaatt cgttagaaat  1680
gtctagggaa gttttgtgaa ccttatcact taaaggaagg agaagtcgta acaaggtttc  1740
cg                                                                 1742

SEQ ID NO: 74           moltype = DNA   length = 1708
FEATURE                 Location/Qualifiers
source                  1..1708
                        mol_type = genomic DNA
                        organism = Plasmodium falciparum
SEQUENCE: 74
tcaaagatta agccatgcaa gtgaaagtat atatatattt tatatgtaga aactgcgaac    60
ggctcattaa aacagttata gtctacttga cattttttatt ataaggataa ctacggaaaa   120
gctgtagcta atacttgctt tattatcctt tgattttttat ctttggataa gtatttgtta   180
ggccttataa gaaaaaagtt attaacttaa ggaattataa caaagaagta acacgtaata   240
aatttatttt atttagtgtg tatcaatcga gtttctgacc tatcagcttt tgatgttagg   300
gtattggcct aacatggcta tgacgggtaa cggggaatta gagttcgatt ccggagaggg   360
agcctgagaa atagctacca catctaagga aggcagcagg cgcgtaaatt acccaattct   420
aaaaaagaga ggtagtgaca agaaataaca atgcaaggcc aattttttggt tttgtaattg   480
gaatggtggg aatttaaaac cttcccagag taacaattgg agggcaagtc tggtgccagc   540
agccgcggta attccagctc caatagcgta tattaaaatt gttgcagtta aaacgctcgt   600
agttgaattt caaagaatcg atattttatt gtaactattc taggggaact attttaggtt   660
ttcgctttaa tacgcttcct ctattattat gttctttaaa taacaaagat tcttttttaaa   720
atccccactt ttgctttttgc ttttttgggg aatttgttac tttgaataaa ttagaggtgt   780
caaagcaaac agttaaagca tttactgtgt ttgaatacta tagcatgaa taacaaaatt    840
gaacaagcta aaatttttttg ttctttttttc ttattttggc ttagttacga ttaataggag   900
tagcttgggg acattcgtat tcagatgtca gaggtgaaat tcttagattt tctggagacg   960
aacaactgcg aaagcatttg tctaaaatac ttccattaat caagaacgaa agttaaggga  1020
gtgaagacga tcagataccg tcgtaatctt aaccataaac tatgccgact aggtgttgga  1080
tgaaagtgtt aaaaataaaa gtcatctttc taggtgactt ttagattgct tccttcagta  1140
ccttatgaga aatcaaagtc tttgggttct ggggcgagta ttcgcgcaag cgagaaagtt  1200
aaaagaattg acgaaagggc accaccaggc gtggagcttg cggcttaatt tgactcaaca  1260
cggggaaact cactagttta agacaagagt aggattgaca gattaatagc tctttcttga  1320
tttcttggat ggtgatgcat ggccgttttt agttcgtgaa tatgatttgt ctggttaatt  1380
ccgataacga acgagatctt aacctgctaa ttagcggcga gtacactata ttcttatttg  1440
aaattgaaca taggtaacta tacatttatt cagtaatcaa attaggatat ttttattaaa  1500
atatccttttt ccctgttcta ctaataattt gttttttact ctatttctct cttcttttaa  1560
gaatgtactt gcttgattga aaagcttctt agaggaacta tgtgtgtcta acacaaggaa  1620
gtttaaggca acaacaggtc tgtgatgtcc ttagatgaac taggctgcac gcgtgctaca  1680
ctgatatata taacgagttt ttaaaaat                                      1708

SEQ ID NO: 75           moltype = DNA   length = 23
FEATURE                 Location/Qualifiers
```

```
misc_feature          1..23
                      note = Synthetic Oligonucleotide
source                1..23
                      mol_type = other DNA
                      organism = synthetic construct
SEQUENCE: 75
gaagtaggac tttggttcta ttt                                              23

SEQ ID NO: 76         moltype = DNA  length = 21
FEATURE               Location/Qualifiers
misc_feature          1..21
                      note = Synthetic Oligonucleotide
source                1..21
                      mol_type = other DNA
                      organism = synthetic construct
SEQUENCE: 76
atgaagtagg actttggttc t                                                21

SEQ ID NO: 77         moltype = DNA  length = 1727
FEATURE               Location/Qualifiers
source                1..1727
                      mol_type = genomic DNA
                      note = Babesia sp. EU1
                      organism = Babesia venatorum
SEQUENCE: 77
aacctggttg atcctgccag tagtcatatg cttgtcttaa agattaagcc atgcatgtct       60
aagtacaaac ttttttacggt gaaactgcga atggctcatt acaacagtta tagtttctttt   120
ggtattcgtt ttccatggat aaccgtgcta attgtagggc taatacaagt tcgaggcctt     180
ttggcggcgt ttattagttc tataaccacc cttttggttt tcggtgattc ataataaact     240
cgcgaatcgc aatttattgc gatggaccat tcaagtttct gacccatcag cttgacggtca   300
gggtattggc ctaccgaggc agcaacgggt aacggggaat tagggttcga ttccggagag     360
ggagcctgag aaacggctac cacatccaag gaaggcagca ggcgcgcaaa ttacccaatc     420
ctgacacagg gaggtagtga caagaaataa caatacaggg caattgtctt gtaattgaa      480
tgatggtgac ctaaaccctc accagagtaa caattgtgagg gcaagtctgg tgccagcagc     540
cgcggtaatt ccagctccaa tagcgtatat taaacttgtt gcagttaaaa agctcgtagt     600
tgaatttctg cgttatcgag ttattgactc ttgtctttaa tcgatttcgc tttttgggatt    660
tatcccttt tactttgaga aaattagagt gtttcaagca acttttgtc ttgaatactt       720
cagcatggaa taatagagta ggactttggt tctattttgt tggttttga accttagtaa     780
tggttaatag gaacggttgg gggcattcgt atttaactgt cagaggtgaa attcttagat     840
ttgttaaaga cgaactactg cgaaagcatt tgccaaggac gttttccatta atcaagaacg    900
aaagttaggg gatcgaagac gatcagatac cgtcgtagtc ctaaccataa actatgccga    960
ctagggattg gaggtcgtca ttttttccgac tccttcagca ccttgagaga aatcaaagtc   1020
tttgggttct ggggggagta tggtcgcaag gctgaaactt aaaggaattg acggaagggc    1080
accaccaggc gtggagcctg cggcttaatt tgactcaaca cggggaaact caccaggtcc    1140
agacaatgtt aggattgaca gattgatagc tctttcttga ttctttgggt ggtggtgcat    1200
ggccgttctt agttggtgga gtgatttgtc tggttaattc cgttaacgaa cgagacctta    1260
acctgctaac tagtacccgt aaaaaggttc gtccgttacg gtttgcttct tagagggact    1320
ttgcggctct aagccgcaag gaagtttaag gcaataacag gtctgtgatg ccctttagtg    1380
tcctgggctg cacgcgcgct acactgatgc attcatcgag tttaatcctg tcccgaaagg    1440
gctgggtaat ctttagtatg catcgtgacg gggattgatt tttgcaattc taatcatga    1500
acgaggaatg cctagtatgc gcaagtcatc agcttgtgca gattacgtcc ctgccctttg    1560
tacacaccgc ccgtcgctcc taccgatcga gtgatccggt gaattattcg gaccgtggct    1620
tttccgattc gtcggttttg cctagggaag tctcgtgaac cttatcactt aaaggaagga    1680
gaagtcgtaa caaggtttcc gtaggtgaac ctgcagaagg atcaagc                  1727

SEQ ID NO: 78         moltype = DNA  length = 41
FEATURE               Location/Qualifiers
misc_feature          1..41
                      note = Synthetic Oligonucleotide
source                1..41
                      mol_type = other DNA
                      organism = synthetic construct
SEQUENCE: 78
gyygccycgg taggccaata ccctaccgtc caaagctgat r                          41

SEQ ID NO: 79         moltype = DNA  length = 41
FEATURE               Location/Qualifiers
misc_feature          1..41
                      note = Synthetic Oligonucleotide
source                1..41
                      mol_type = other DNA
                      organism = synthetic construct
SEQUENCE: 79
gyygccycgg taggccaata ccctaccgtc caaagctgat r                          41

SEQ ID NO: 80         moltype = DNA  length = 60
FEATURE               Location/Qualifiers
misc_feature          1..60
                      note = Synthetic Oligonucleotide
```

```
regulatory              1..27
                        regulatory_class = promoter
variation               50
                        note = "n" means a or g or c or t/u, or unknown, or other
                         (WIPO StandardST.25 (1998), Appendix 2, Table 1)
misc_difference         50
                        note = n is a, c, g, or t
source                  1..60
                        mol_type = other DNA
                        organism = synthetic construct
SEQUENCE: 80
aatttaatac gactcactat agggagaggc aaatgctttc gcagtagttn gtctttaaca    60

SEQ ID NO: 81           moltype = DNA  length = 33
FEATURE                 Location/Qualifiers
misc_feature            1..33
                        note = Synthetic oligonucleotide
variation               23
                        note = "n" means a or g or c or t/u, or unknown, or other
                         (WIPO StandardST.25 (1998), Appendix 2, Table 1)
misc_difference         23
                        note = n is a, c, g, or t
source                  1..33
                        mol_type = other DNA
                        organism = synthetic construct
SEQUENCE: 81
ggcaaatgct ttcgcagtag ttngtcttta aca                                  33

SEQ ID NO: 82           moltype = DNA  length = 60
FEATURE                 Location/Qualifiers
misc_feature            1..60
                        note = Synthetic Oligonucleotide
regulatory              1..27
                        regulatory_class = promoter
modified_base           50
                        mod_base = i
source                  1..60
                        mol_type = other DNA
                        organism = synthetic construct
SEQUENCE: 82
aatttaatac gactcactat agggagaggc aaatgctttc gcagtagttn gtctttaaca    60

SEQ ID NO: 83           moltype = DNA  length = 33
FEATURE                 Location/Qualifiers
misc_feature            1..33
                        note = Synthetic Oligonucleotide
modified_base           23
                        mod_base = i
source                  1..33
                        mol_type = other DNA
                        organism = synthetic construct
SEQUENCE: 83
ggcaaatgct ttcgcagtag ttngtcttta aca                                  33

SEQ ID NO: 84           moltype = DNA  length = 22
FEATURE                 Location/Qualifiers
misc_feature            1..22
                        note = Synthetic oligonucleotide
source                  1..22
                        mol_type = other DNA
                        organism = synthetic construct
SEQUENCE: 84
gcggtaattc cagctccaat ag                                              22

SEQ ID NO: 85           moltype = DNA  length = 16
FEATURE                 Location/Qualifiers
misc_feature            1..16
                        note = Synthetic oligonucleotide
variation               11
                        note = "n" means a or g or c or t/u, or unknown, or other
                         (WIPO StandardST.25 (1998), Appendix 2, Table 1)
source                  1..16
                        mol_type = other DNA
                        organism = synthetic construct
misc_difference         11
                        note = n is a, c, g, or t
SEQUENCE: 85
cttgaatact ncagca                                                     16
```

```
SEQ ID NO: 86              moltype = DNA  length = 16
FEATURE                    Location/Qualifiers
misc_feature               1..16
                           note = Synthetic Oligonucleotide
modified_base              11
                           mod_base = i
source                     1..16
                           mol_type = other DNA
                           organism = synthetic construct
SEQUENCE: 86
cttgaatact ncagca                                                   16

SEQ ID NO: 87              moltype = DNA  length = 56
FEATURE                    Location/Qualifiers
misc_feature               1..56
                           note = Synthetic oligonucleotide
misc_feature               24..56
                           note = capture tail
source                     1..56
                           mol_type = other DNA
                           organism = synthetic construct
SEQUENCE: 87
aaagactttg atttctctca aggttaaaa aaaaaaaaaa aaaaaaaaaa aaaaaa        56

SEQ ID NO: 88              moltype = DNA  length = 23
FEATURE                    Location/Qualifiers
misc_feature               1..23
                           note = Synthetic oligonucleotide
source                     1..23
                           mol_type = other DNA
                           organism = synthetic construct
SEQUENCE: 88
aaagactttg atttctctca agg                                           23

SEQ ID NO: 89              moltype = DNA  length = 61
FEATURE                    Location/Qualifiers
misc_feature               1..61
                           note = Synthetic oligonucleotide
misc_feature               29..61
                           note = capture tail
source                     1..61
                           mol_type = other DNA
                           organism = synthetic construct
SEQUENCE: 89
caagaaagag ctatcaatct gtcaatcctt taaaaaaaaa aaaaaaaaaa aaaaaaaaaa   60
a                                                                   61

SEQ ID NO: 90              moltype = DNA  length = 28
FEATURE                    Location/Qualifiers
misc_feature               1..28
                           note = Synthetic oligonucleotide
source                     1..28
                           mol_type = other DNA
                           organism = synthetic construct
SEQUENCE: 90
caagaaagag ctatcaatct gtcaatcc                                      28

SEQ ID NO: 91              moltype = DNA  length = 17
FEATURE                    Location/Qualifiers
misc_feature               1..17
                           note = Synthetic oligonucleotide
source                     1..17
                           mol_type = other DNA
                           organism = synthetic construct
SEQUENCE: 91
agtaggactt tggttct                                                  17

SEQ ID NO: 92              moltype = DNA  length = 16
FEATURE                    Location/Qualifiers
misc_feature               1..16
                           note = Synthetic oligonucleotide
source                     1..16
                           mol_type = other DNA
                           organism = synthetic construct
SEQUENCE: 92
agtaggactt tggttc                                                   16

SEQ ID NO: 93              moltype = DNA  length = 17
FEATURE                    Location/Qualifiers
```

```
misc_feature            1..17
                        note = Synthetic oligonucleotide
source                  1..17
                        mol_type = other DNA
                        organism = synthetic construct
SEQUENCE: 93
agtaggacta ttggttc                                                    17

SEQ ID NO: 94           moltype = DNA  length = 16
FEATURE                 Location/Qualifiers
misc_feature            1..16
                        note = Synthetic Oligonucleotide
misc_difference         9
                        note = n is u or ua
source                  1..16
                        mol_type = other DNA
                        organism = synthetic construct
SEQUENCE: 94
agtaggacnt tggttc                                                     16

SEQ ID NO: 95           moltype = DNA  length = 95
FEATURE                 Location/Qualifiers
misc_feature            1..95
                        note = Synthetic oligonucleotide
variation               50
                        note = "n" means a or g or c or t/u, or unknown, or other
                        (WIPO StandardST.25 (1998), Appendix 2, Table 1)
misc_difference         50
                        note = n is a, c, g, t, or u
source                  1..95
                        mol_type = other DNA
                        organism = synthetic construct
SEQUENCE: 95
actttgagaa aaytagagtg tttcaaacag gccatttgcc ttgaatactn cagcatggaa     60
taatgaagta ggactttggt tctatttgt tggtt                                 95

SEQ ID NO: 96           moltype = DNA  length = 78
FEATURE                 Location/Qualifiers
misc_feature            1..78
                        note = Synthetic oligonucleotide
variation               23
                        note = "n" means a or g or c or t/u, or unknown, or other
                        (WIPO StandardST.25 (1998), Appendix 2, Table 1)
misc_difference         23
                        note = n is a, c, g, t, or u
source                  1..78
                        mol_type = other DNA
                        organism = synthetic construct
SEQUENCE: 96
ggcaaatgct ttcgcagtag ttngtcttta acaaatctaa gaatttcacc tctgacagtt     60
aaatacgaat gccccaa                                                    78

SEQ ID NO: 97           moltype = DNA  length = 37
FEATURE                 Location/Qualifiers
misc_feature            1..37
                        note = Synthetic oligonucleotide
variation               23
                        note = "n" means a or g or c or t/u, or unknown, or other
                        (WIPO StandardST.25 (1998), Appendix 2, Table 1)
misc_difference         23
                        note = n is a, c, g, t, or u
source                  1..37
                        mol_type = other DNA
                        organism = synthetic construct
SEQUENCE: 97
ggcaaatgct ttcgcagtag ttngtcttta acaaatc                              37

SEQ ID NO: 98           moltype = DNA  length = 18
FEATURE                 Location/Qualifiers
misc_feature            1..18
                        note = Synthetic oligonucleotide
source                  1..18
                        mol_type = other DNA
                        organism = synthetic construct
SEQUENCE: 98
agtaggacta ttggttct                                                   18

SEQ ID NO: 99           moltype = DNA  length = 17
FEATURE                 Location/Qualifiers
```

```
misc_feature           1..17
                       note = Synthetic Oligonucleotide
misc_difference        9
                       note = n is u or ua
source                 1..17
                       mol_type = other DNA
                       organism = synthetic construct
SEQUENCE: 99
agtaggacnt tggttct                                                          17

SEQ ID NO: 100         moltype = RNA  length = 1281
FEATURE                Location/Qualifiers
misc_feature           1..1281
                       note = B. venatorum In Vitro Transcript
source                 1..1281
                       mol_type = izing sequence consisting of the sequence selected from the group consisting of: SEQ ID NO:37, SEQ ID NO:42, SEQ ID NO:91, SEQ ID NO: 92, SEQ ID NO:93, and combinations thereof.

8. The combination of claim 7, wherein the detection probe comprises a fluorescent label and a quencher.

9. The combination of claim 1, wherein the at least two amplification oligomers further comprise:
  (a) a third amplification oligomer comprising a third target-hybridizing sequence that consists of SEQ ID NO:83;
  (b) a fourth amplification oligomer comprising a fourth target-hybridizing sequence that consists of SEQ ID NO:84; and,
  (c) a fifth amplification oligomer comprising a fifth target-hybridizing sequence that consists of SEQ ID NO:86.

10. The combination of claim 9, further comprising at least one capture probe oligomer, wherein the at least one capture probe oligomer comprises a target-hybridizing sequence covalently attached to a sequence or moiety that binds to an immobilized probe, wherein said target-hybridizing sequence consists of SEQ ID NO:44, SEQ ID NO:88, or SEQ ID NO:90.

11. The combination of claim 1, further comprising a detection probe oligomer, wherein the detection probe oligomer comprises a detection probe target-hybridizing sequence consisting of a sequence selected from the group consisting of SEQ ID NO: 91, SEQ ID NO:92, and SEQ ID NO:93.

12. A combination of at least two oligomers for determining the presence or absence of *Babesia* in a sample, said oligomer combination comprising first and second amplification oligomers for amplifying a target region of *Babesia* target nucleic acid, wherein
  (a) the first amplification oligomer comprises a first target-hybridizing sequence that consists of SEQ ID NO:8, wherein the first amplification oligomer is a promoter primer or promoter provider further comprising a promoter sequence located 5' to the first target-hybridizing sequence;
  (b) the second amplification oligomer comprises a second target-hybridizing sequence that consists of SEQ ID NO:34; and
  (c) a detection probe oligomer configured to specifically hybridize to a *Babesia* amplification product amplifiable by the first and second amplification oligomers, wherein the detection probe oligomer comprises a 2' methoxy modification on at least one nucleotide residue member of the nucleotide sequence.

13. A combination of at least two oligomers for determining the presence or absence of *Babesia* in a sample, said oligomer combination comprising first and second amplification oligomers for amplifying a target region of *Babesia* target nucleic acid, wherein
  (a) the first amplification oligomer comprises a first target-hybridizing sequence that consists of SEQ ID NO:8, wherein the first amplification oligomer is a promoter primer or promoter provider further comprising a promoter sequence located 5' to the first target-hybridizing sequence;
  (b) the second amplification oligomer comprises a second target-hybridizing sequence that consists of SEQ ID NO:34; and
  (c) a detection probe oligomer configured to specifically hybridize to a *Babesia* amplification product amplifiable by the first and second amplification oligomers, wherein the detection probe comprises a chemiluminescent label or a fluorescent label.

* * * * *